(12) United States Patent
Lin et al.

(10) Patent No.: US 8,298,535 B2
(45) Date of Patent: Oct. 30, 2012

(54) ANTI-IL-7 RECEPTOR ANTIBODIES

(75) Inventors: Chia-Yang Lin, Palo Alto, CA (US);
Li-Fen Lee, Palo Alto, CA (US);
Wenwu Zhai, Redwood City, CA (US)

(73) Assignee: Rinat Neuroscience Corp., South San Francisco, CA (US)

( * ) Notice: Subject to any disclaimer, the term of this patent is extended or adjusted under 35 U.S.C. 154(b) by 0 days.

(21) Appl. No.: 13/033,491

(22) Filed: Feb. 23, 2011

(65) Prior Publication Data

US 2011/0206698 A1 Aug. 25, 2011

Related U.S. Application Data

(60) Provisional application No. 61/307,670, filed on Feb. 24, 2010, provisional application No. 61/438,205, filed on Jan. 31, 2011.

(51) Int. Cl.
*A61K 39/395* (2006.01)
*C07K 16/28* (2006.01)
*C12N 5/12* (2006.01)

(52) U.S. Cl. ............. 424/143.1; 424/141.1; 530/388.22; 435/326

(58) Field of Classification Search .................. None
See application file for complete search history.

(56) References Cited

U.S. PATENT DOCUMENTS

| | | | |
|---|---|---|---|
| 5,264,416 | A | 11/1993 | Park et al. |
| 5,543,320 | A | 8/1996 | Park et al. |
| 6,713,053 | B1 | 3/2004 | Bach et al. |
| 2006/0198822 | A1 | 9/2006 | Booth et al. |
| 2010/0040616 | A1 | 2/2010 | Leung et al. |

FOREIGN PATENT DOCUMENTS

| | | |
|---|---|---|
| WO | WO 2006/052660 A2 | 5/2006 |
| WO | WO 2010/017468 A1 | 2/2010 |
| WO | WO 2010/085643 A1 | 7/2010 |

OTHER PUBLICATIONS

Fry, et al., "The many faces of IL-7: from lymphopoiesis to peripheral T cell maintenance," *J Immunol.*, 2005, 6571-6, vol. 174, No. 11.
Jiang, et al., "Cell biology of IL-7, a key lymphotrophin," *Cytokine Growth Factor Rev.*, 2005, 513-33, vol. 16, No. 4-5.
Liu, et al., "Crucial role of interleukin-7 in T helper type 17 survival and expansion in autoimmune disease," *Nat Med.*, 2010, 191-7, vol. 16, No. 2.
Mazzucchelli, et al., "Interleukin-7 receptor expression: intelligent design," *Nat Rev Immunol.*, 2007, 144-54, vol. 7, No. 2.
Reche, et al., "Human thymic stromal lymphopoietin preferentially stimulates myeloid cells," *J Immunol.*, 2001, 336-43, vol. 167, No. 1.
Yamazaki, et al., "Mucosal T Cells Expressing High Levels of IL-7 Receptor Are Potential Targets for Treatment of Chronic Colitis," *J Immunol.*, 2003, 1556-1563, vol. 171, No. 3.
Chung, et al., "Prevention of graft-versus-host disease by anti-IL-7Rα antibody," *Blood*, 2007, 2803-2810, vol. 110, No. 8.
International Search Report mailed Jul. 21, 2011 for PCT/IB2011/050792.
Written Opinion of the International Searching Authority issued Jul. 21, 2011 for PCT/IB2011/050792.
Written Opinion of the International Searching Authority issued Jan. 9, 2012 for PCT/IB2011/050792.
International Preliminary Report on Patentability mailed Mar. 30, 2012 for PCT/IB2011/050792.

*Primary Examiner* — Prema Mertz
(74) *Attorney, Agent, or Firm* — Susan L. Wang; Deborah A. Martin

(57) ABSTRACT

The present invention provides antagonizing antibodies that bind to interleukin-7 receptor (IL-7R). The invention further provides a method of obtaining such antibodies and antibody-encoding nucleic acids. The invention further relates to therapeutic methods for use of these antibodies and antigen-binding portions thereof for the treatment and/or prevention of type 2 diabetes and immunological disorders, including type 1 diabetes, multiple sclerosis, rheumatoid arthritis, graft-versus-host disease, and lupus.

10 Claims, 15 Drawing Sheets

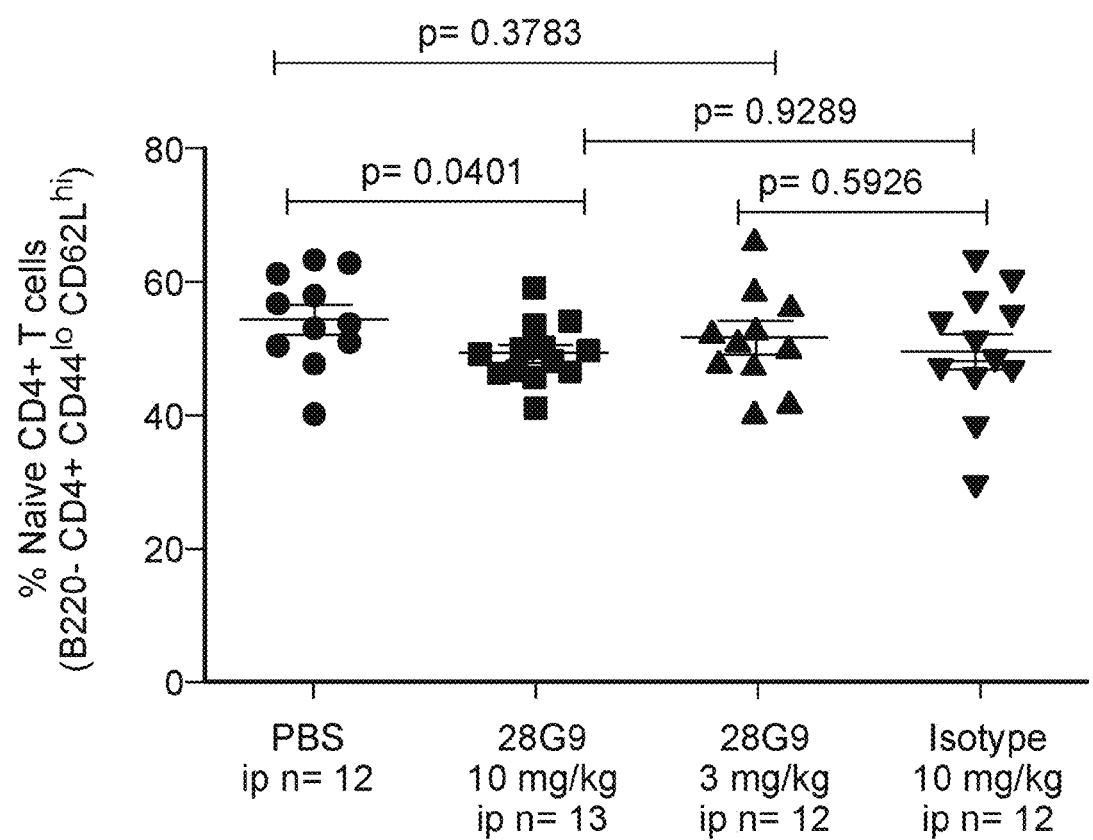

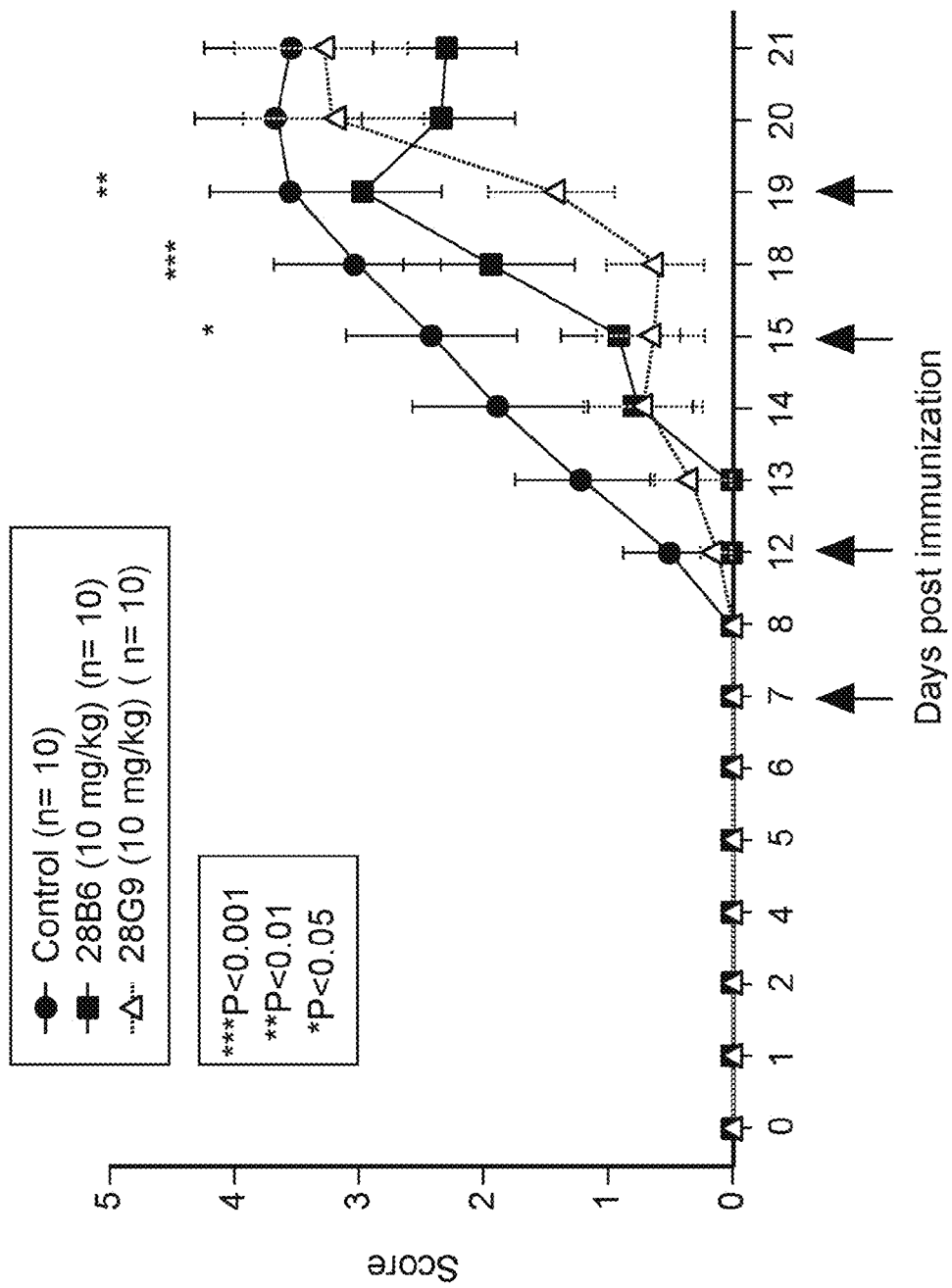

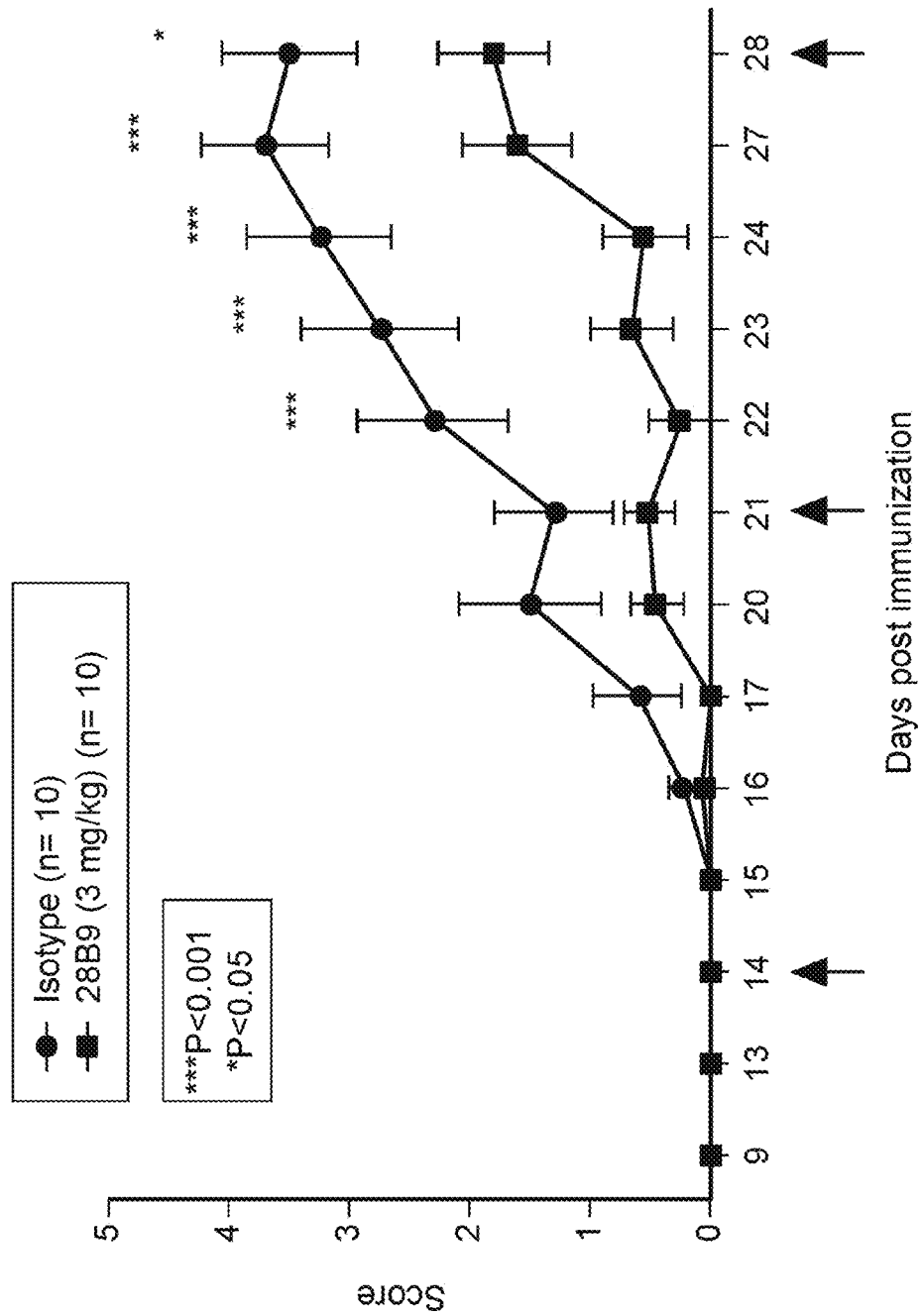

SEQUENCE LISTING

<160> NUMBER OF SEQ ID NOS: 61

<210> SEQ ID NO 1
<211> LENGTH: 111
<212> TYPE: PRT
<213> ORGANISM: Homo sapiens

<400> SEQUENCE: 1

Asn Phe Met Leu Thr Gln Pro His Ser Val Ser Gly Ser Pro Gly Lys
1               5                   10                  15

Thr Val Thr Ile Ser Cys Thr Arg Ser Ser Gly Ser Ile Asp Ser Ser
            20                  25                  30

Tyr Val Gln Trp Tyr Gln Gln Arg Pro Gly Asn Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Val Thr Glu Asp Glu Ala Asp Tyr Tyr Cys Gln Ser Tyr Asp Ser
                85                  90                  95

Ser His Leu Val Phe Gly Gly Gly Thr Lys Leu Thr Val Leu Cys
            100                 105                 110

<210> SEQ ID NO 2
<211> LENGTH: 117
<212> TYPE: PRT
<213> ORGANISM: Homo sapiens

<400> SEQUENCE: 2

Gln Val Asn Leu Arg Glu Ser Gly Gly Gly Leu Val Lys Pro Gly Gly
1               5                   10                  15

Ser Leu Arg Leu Ser Cys Ala Ala Ser Gly Phe Thr Phe Asp Asp Ser
            20                  25                  30

Val Met His Trp Val Arg Gln Ala Pro Gly Lys Gly Leu Glu Trp Leu
        35                  40                  45

Ser Leu Val Gly Trp Asp Gly Ser Ala Thr Tyr Tyr Ala Asp Ser Val
    50                  55                  60

Lys Gly Arg Phe Thr Ile Ser Arg Asp Asn Lys Asn Leu Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Asp Tyr Val Phe Asp Tyr Trp Gly Gln Gly Thr Leu
            100                 105                 110

Val Thr Val Ser Ser
        115

<210> SEQ ID NO 3
<211> LENGTH: 112
<212> TYPE: PRT
<213> ORGANISM: Homo sapiens

<400> SEQUENCE: 3

Asn Phe Met Leu Thr Gln Pro His Ser Val Ser Glu Ser Pro Gly Lys
1               5                   10                  15

Thr Val Thr Ile Ser Cys Thr Gly Ser Ser Gly Arg Ile Ala Ser Ser
            20                  25                  30

Tyr Val Gln Trp Tyr Gln Gln Arg Pro Gly Ser Ala Pro Thr Thr Val

```
                35                  40                  45
Ile Tyr Glu Asp Asn Gln Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Ala Ser
                 85                  90                  95

Ser Ser Leu Trp Val Phe Gly Gly Gly Thr Gln Leu Thr Val Leu Ser
                100                 105                 110

<210> SEQ ID NO 4
<211> LENGTH: 118
<212> TYPE: PRT
<213> ORGANISM: Homo sapiens

<400> SEQUENCE: 4

Gln Val Thr Leu Lys Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Asp Glu Asp Thr Ala Val Tyr Tyr Cys
                85                  90                  95

Ala Arg Asp Ile Ser Gly Gly Met Asp Val Trp Gly Gln Gly Thr
                100                 105                 110

Thr Val Thr Val Ser Ser
        115

<210> SEQ ID NO 5
<211> LENGTH: 111
<212> TYPE: PRT
<213> ORGANISM: Homo sapiens

<400> SEQUENCE: 5

Asn Phe Met Leu Thr Gln Pro His Ser Val Ser Gly Ser Pro Gly Lys
 1               5                  10                  15

Thr Val Thr Ile Ser Cys Thr Arg Ser Ser Gly Ser Ile Asp Ser Ser
                20                  25                  30

Tyr Val Gln Trp Tyr Gln Gln Arg Pro Gly Asn Ser Pro Thr Thr Val
                35                  40                  45

Ile Tyr Glu Asp Asp Gln Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Val Thr Glu Asp Glu Ala Asp Tyr Tyr Cys Met Gln Tyr Asp Ser
                85                  90                  95

Ser His Leu Val Phe Gly Gly Gly Thr Lys Leu Thr Val Leu Cys
                100                 105                 110

<210> SEQ ID NO 6
<211> LENGTH: 117
<212> TYPE: PRT
<213> ORGANISM: Homo sapiens
```

<400> SEQUENCE: 6

Gln Val Asn Leu Arg Glu Ser Gly Gly Gly Leu Val Lys Pro Gly Gly
1               5                   10                  15

Ser Leu Arg Leu Ser Cys Ala Ala Ser Gly Phe Thr Phe Asp Asp Ser
            20                  25                  30

Val Met His Trp Val Arg Gln Ala Pro Gly Lys Gly Leu Glu Trp Leu
        35                  40                  45

Ser Leu Val Gly Trp Asp Gly Phe Phe Thr Tyr Tyr Ala Asp Ser Val
    50                  55                  60

Lys Gly Arg Phe Thr Ile Ser Arg Asp Asn Thr Lys Asn Leu Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Asp Tyr Val Phe Asn Asn Trp Gly Gln Gly Thr Leu
            100                 105                 110

Val Thr Val Ser Ser
            115

<210> SEQ ID NO 7
<211> LENGTH: 111
<212> TYPE: PRT
<213> ORGANISM: Homo sapiens

<400> SEQUENCE: 7

Asn Phe Met Leu Thr Gln Pro His Ser Val Ser Gly Ser Pro Gly Lys
1               5                   10                  15

Thr Val Thr Ile Ser Cys Thr Arg Ser Ser Gly Ser Ile Asp Ser Ser
            20                  25                  30

Tyr Val Gln Trp Tyr Gln Gln Arg Pro Gly Asn Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Val Thr Glu Asp Glu Ala Asp Tyr Tyr Cys Gln Ser Tyr Asp Phe
                85                  90                  95

His His Leu Val Phe Gly Gly Gly Thr Lys Leu Thr Val Leu Cys
            100                 105                 110

<210> SEQ ID NO 8
<211> LENGTH: 117
<212> TYPE: PRT
<213> ORGANISM: Homo sapiens

<400> SEQUENCE: 8

Gln Val Asn Leu Arg Glu Ser Gly Gly Gly Leu Val Lys Pro Gly Gly
1               5                   10                  15

Ser Leu Arg Leu Ser Cys Ala Ala Ser Gly Phe Thr Phe Asp Asp Ser
            20                  25                  30

Val Met His Trp Val Arg Gln Ala Pro Gly Lys Gly Leu Glu Trp Leu
        35                  40                  45

Ser Leu Val Gly Trp Asp Gly Phe Phe Thr Tyr Tyr Ala Asp Ser Val
    50                  55                  60

Lys Gly Arg Phe Thr Ile Ser Arg Asp Asn Thr Lys Asn Leu Leu Tyr
65                  70                  75                  80

Leu Gln Met Asn Ser Leu Arg Ala Glu Asp Thr Ala Val Tyr Tyr Cys

```
                    85                  90                  95
Ala Arg Gln Gly Asp Tyr Met Gly Asp Tyr Trp Gly Gln Gly Thr Leu
                100                 105                 110

Val Thr Val Ser Ser
        115

<210> SEQ ID NO 9
<211> LENGTH: 111
<212> TYPE: PRT
<213> ORGANISM: Homo sapiens

<400> SEQUENCE: 9

Asn Phe Met Leu Thr Gln Pro His Ser Val Ser Gly Ser Pro Gly Lys
1               5                   10                  15

Thr Val Thr Ile Ser Cys Thr Arg Ser Ser Gly Ser Ile Asp Ser Ser
            20                  25                  30

Tyr Val Gln Trp Tyr Gln Gln Arg Pro Gly Asn Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Val Thr Glu Asp Glu Ala Asp Tyr Tyr Cys Gln Ser Tyr Asp Phe
                85                  90                  95

His His Leu Val Phe Gly Gly Gly Thr Lys Leu Thr Val Leu Cys
                100                 105                 110

<210> SEQ ID NO 10
<211> LENGTH: 117
<212> TYPE: PRT
<213> ORGANISM: Homo sapiens

<400> SEQUENCE: 10

Gln Val Asn Leu Arg Glu Ser Gly Gly Gly Leu Val Lys Pro Gly Gly
1               5                   10                  15

Ser Leu Arg Leu Ser Cys Ala Ala Ser Gly Phe Thr Phe Asp Asp Ser
            20                  25                  30

Val Met His Trp Val Arg Gln Ala Pro Gly Lys Gly Leu Glu Trp Leu
        35                  40                  45

Ser Leu Val Gly Trp Asp Gly Phe Phe Thr Tyr Tyr Ala Asp Ser Val
    50                  55                  60

Lys Gly Arg Phe Thr Ile Ser Arg Asp Asn Thr Lys Asn Leu Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Asp Tyr Met Gly Asn Asn Trp Gly Gln Gly Thr Leu
                100                 105                 110

Val Thr Val Ser Ser
        115

<210> SEQ ID NO 11
<211> LENGTH: 111
<212> TYPE: PRT
<213> ORGANISM: Homo sapiens

<400> SEQUENCE: 11

Asn Phe Met Leu Thr Gln Pro His Ser Val Ser Gly Ser Pro Gly Lys
1               5                   10                  15
```

```
Thr Val Thr Ile Ser Cys Thr Arg Ser Ser Gly Ser Ile Asp Ser Ser
            20                  25                  30

Tyr Val Gln Trp Tyr Gln Gln Arg Pro Gly Asn Ser Pro Thr Thr Val
        35                  40                  45

Ile Tyr Glu Asp Asp Gln Arg Pro Ser Gly Val Pro Asp Arg Phe Ser
50                  55                  60

Gly Ser Ile Asp Ser Ser Asn Ser Ala Ser Leu Thr Ile Ser Gly
65                  70                  75                  80

Leu Val Thr Glu Asp Glu Ala Asp Tyr Tyr Cys Met Gln Tyr Asp Phe
                85                  90                  95

His His Leu Val Phe Gly Gly Gly Thr Lys Leu Thr Val Leu Cys
            100                 105                 110

<210> SEQ ID NO 12
<211> LENGTH: 117
<212> TYPE: PRT
<213> ORGANISM: Homo sapiens

<400> SEQUENCE: 12

Gln Val Asn Leu Arg Glu Ser Gly Gly Gly Leu Val Lys Pro Gly Gly
1               5                   10                  15

Ser Leu Arg Leu Ser Cys Ala Ala Ser Gly Phe Thr Phe Asp Asp Ser
            20                  25                  30

Val Met His Trp Val Arg Gln Ala Pro Gly Lys Gly Leu Glu Trp Leu
        35                  40                  45

Ser Leu Val Gly Trp Asp Gly Phe Phe Thr Tyr Tyr Ala Asp Ser Val
50                  55                  60

Lys Gly Arg Phe Thr Ile Ser Arg Asp Asn Thr Lys Asn Leu Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Asp Tyr Met Gly Asn Asn Trp Gly Gln Gly Thr Leu
            100                 105                 110

Val Thr Val Ser Ser
        115

<210> SEQ ID NO 13
<211> LENGTH: 15
<212> TYPE: PRT
<213> ORGANISM: Artificial Sequence
<220> FEATURE:
<223> OTHER INFORMATION: Linking peptide

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 351
<212> TYPE: DNA
<213> ORGANISM: Homo sapiens

<400> SEQUENCE: 14
caggtcaact taagggagtc tgggggaggc ctggtcaagc cggggggtc cctgagactc      60 tcctgtgcag cctctggatt cacctttgat gattctgtca tgcactgggt ccgtcaagct    120
ccggggaagg gtctggagtg gctctctctt gttggttggg atggtttttt tacatactat    180
gcagactcag tgaagggccg attcaccatc tccagagaca acaccaagaa cttactgtat    240
ctgcaaatga acagcctgag agccgaggac acggctgtgt attactgtgc gagacaaggg    300
```

```
gattacatgg ggaacaactg gggccaggga accctggtca ccgtctcctc a        351
```

<210> SEQ ID NO 15
<211> LENGTH: 333
<212> TYPE: DNA
<213> ORGANISM: Homo sapiens

<400> SEQUENCE: 15

```
aattttatgc tgactcagcc ccactctgtg tcggggtctc cgggaaagac ggtgaccatc   60
tcctgcaccc gcagcagtgg cagcattgac agttcctatg tgcagtggta ccagcagcgc  120
ccgggcaatt cccccaccac tgtgatctat gaggatgacc aaagaccctc tggggtccct  180
gatcggttct ctggctccat cgacagctcc tccaactctg cctccctcac catctctgga  240
ctggtgactg aggacgaggc tgactactac tgtcagtctt atgattttca tcatctggtg  300
ttcggcggag ggaccaagct gaccgtccta tgt                              333
```

<210> SEQ ID NO 16
<211> LENGTH: 15
<212> TYPE: PRT
<213> ORGANISM: Artificial Sequence
<220> FEATURE:
<223> OTHER INFORMATION: linker peptide

<400> SEQUENCE: 16

Gly Gly Gly Gly Ser Gly Gly Gly Ser Gly Gly Gly Gly Ser
1               5                   10                  15

<210> SEQ ID NO 17
<211> LENGTH: 431
<212> TYPE: PRT
<213> ORGANISM: Homo sapiens

<400> SEQUENCE: 17

Gln Val Asn Leu Arg Glu Ser Gly Gly Gly Leu Val Lys Pro Gly Gly
1               5                   10                  15

Ser Leu Arg Leu Ser Cys Ala Ala Ser Gly Phe Thr Phe Asp Asp Ser
            20                  25                  30

Val Met His Trp Val Arg Gln Ala Pro Gly Lys Gly Leu Glu Trp Leu
        35                  40                  45

Ser Leu Val Gly Trp Asp Gly Phe Phe Thr Tyr Tyr Ala Asp Ser Val
    50                  55                  60

Lys Gly Arg Phe Thr Ile Ser Arg Asp Asn Thr Lys Asn Leu Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Asp Tyr Met Gly Asn Asn Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

```
Phe Gly Thr Gln Thr Tyr Thr Cys Asn Val Asp His Lys Pro Ser Asn
            195                 200                 205
Thr Lys Val Asp Lys Thr Val Ala Pro Pro Val Ala Gly Pro Ser Val
210                 215                 220
Phe Leu Phe Pro Pro Lys Pro Lys Asp Thr Leu Met Ile Ser Arg Thr
225                 230                 235                 240
Pro Glu Val Thr Cys Val Val Val Asp Val Ser His Glu Asp Pro Glu
                245                 250                 255
Val Gln Phe Asn Trp Tyr Val Asp Gly Val Glu Val His Asn Ala Lys
            260                 265                 270
Thr Lys Pro Arg Glu Glu Gln Phe Asn Ser Thr Phe Arg Val Val Ser
        275                 280                 285
Val Leu Thr Val Val His Gln Asp Trp Leu Asn Gly Lys Glu Tyr Lys
    290                 295                 300
Cys Lys Val Ser Asn Lys Gly Leu Pro Ser Ser Ile Glu Lys Thr Ile
305                 310                 315                 320
Ser Lys Thr Lys Gly Gln Pro Arg Glu Pro Gln Val Tyr Thr Leu Pro
                325                 330                 335
Pro Ser Arg Glu Glu Met Thr Lys Asn Gln Val Ser Leu Thr Cys Leu
            340                 345                 350
Val Lys Gly Phe Tyr Pro Ser Asp Ile Ala Val Glu Trp Glu Ser Asn
        355                 360                 365
Gly Gln Pro Glu Asn Asn Tyr Lys Thr Thr Pro Pro Met Leu Asp Ser
    370                 375                 380
Asp Gly Ser Phe Phe Leu Tyr Ser Lys Leu Thr Val Asp Lys Ser Arg
385                 390                 395                 400
Trp Gln Gln Gly Asn Val Phe Ser Cys Ser Val Met His Glu Ala Leu
                405                 410                 415
His Asn His Tyr Thr Gln Lys Ser Leu Ser Leu Ser Pro Gly Lys
            420                 425                 430

<210> SEQ ID NO 18
<211> LENGTH: 216
<212> TYPE: PRT
<213> ORGANISM: Homo sapiens

<400> SEQUENCE: 18

Asn Phe Met Leu Thr Gln Pro His Ser Val Ser Gly Ser Pro Gly Lys
1               5                   10                  15
Thr Val Thr Ile Ser Cys Thr Arg Ser Ser Gly Ser Ile Asp Ser Ser
            20                  25                  30
Tyr Val Gln Trp Tyr Gln Gln Arg Pro Gly Asn Ser Pro Thr Thr Val
        35                  40                  45
Ile Tyr Glu Asp Asp Gln Arg Pro Ser Gly Val Pro Asp Arg Phe Ser
    50                  55                  60
Gly Ser Ile Asp Ser Ser Asn Ser Ala Ser Leu Thr Ile Ser Gly
65                  70                  75                  80
Leu Val Thr Glu Asp Glu Ala Asp Tyr Tyr Cys Gln Ser Tyr Asp Phe
                85                  90                  95
His His Leu Val Phe Gly Gly Gly Thr Lys Leu Thr Val Leu Thr Val
            100                 105                 110
Ala Ala Pro Ser Val Phe Ile Phe Pro Pro Ser Asp Glu Gln Leu Lys
        115                 120                 125
Ser Gly Thr Ala Ser Val Val Cys Leu Leu Asn Asn Phe Tyr Pro Arg
    130                 135                 140
```

```
Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 19
<211> LENGTH: 5
<212> TYPE: PRT
<213> ORGANISM: Homo sapiens

<400> SEQUENCE: 19

```
Asp Ser Val Met His
1               5
```

<210> SEQ ID NO 20
<211> LENGTH: 5
<212> TYPE: PRT
<213> ORGANISM: Homo sapiens

<400> SEQUENCE: 20

```
Asn Tyr Gly Met His
1               5
```

<210> SEQ ID NO 21
<211> LENGTH: 17
<212> TYPE: PRT
<213> ORGANISM: Homo sapiens

<400> SEQUENCE: 21

```
Leu Val Gly Trp Asp Gly Ser Ala Thr Tyr Tyr Ala Asp Ser Val Lys
1               5                   10                  15

Gly
```

<210> SEQ ID NO 22
<211> LENGTH: 17
<212> TYPE: PRT
<213> ORGANISM: Homo sapiens

<400> SEQUENCE: 22

```
Ala Ile Ser Gly Ser Gly Gly Ser Thr Tyr Tyr Ala Asp Ser Val Lys
1               5                   10                  15

Gly
```

<210> SEQ ID NO 23
<211> LENGTH: 17
<212> TYPE: PRT
<213> ORGANISM: Homo sapiens

<400> SEQUENCE: 23

```
Leu Val Gly Trp Asp Gly Phe Phe Thr Tyr Tyr Ala Asp Ser Val Lys
1               5                   10                  15

Gly
```

<210> SEQ ID NO 24
<211> LENGTH: 8
<212> TYPE: PRT

-continued

<213> ORGANISM: Homo sapiens

<400> SEQUENCE: 24

Gln Gly Asp Tyr Val Phe Asp Tyr
1               5

<210> SEQ ID NO 25
<211> LENGTH: 9
<212> TYPE: PRT
<213> ORGANISM: Homo sapiens

<400> SEQUENCE: 25

Asp Ile Ser Gly Gly Gly Met Asp Val
1               5

<210> SEQ ID NO 26
<211> LENGTH: 8
<212> TYPE: PRT
<213> ORGANISM: Homo sapiens

<400> SEQUENCE: 26

Gln Gly Asp Tyr Val Phe Asn Asn
1               5

<210> SEQ ID NO 27
<211> LENGTH: 8
<212> TYPE: PRT
<213> ORGANISM: Homo sapiens

<400> SEQUENCE: 27

Gln Gly Asp Tyr Met Gly Asp Tyr
1               5

<210> SEQ ID NO 28
<211> LENGTH: 8
<212> TYPE: PRT
<213> ORGANISM: Homo sapiens

<400> SEQUENCE: 28

Gln Gly Asp Tyr Met Gly Asn Asn
1               5

<210> SEQ ID NO 29
<211> LENGTH: 13
<212> TYPE: PRT
<213> ORGANISM: Homo sapiens

<400> SEQUENCE: 29

Thr Arg Ser Ser Gly Ser Ile Asp Ser Ser Tyr Val Gln
1               5                   10

<210> SEQ ID NO 30
<211> LENGTH: 13
<212> TYPE: PRT
<213> ORGANISM: Homo sapiens

<400> SEQUENCE: 30

Thr Gly Ser Ser Gly Arg Ile Ala Ser Ser Tyr Val Gln
1               5                   10

<210> SEQ ID NO 31
<211> LENGTH: 7
<212> TYPE: PRT
<213> ORGANISM: Homo sapiens

<400> SEQUENCE: 31

```
<210> SEQ ID NO 32
<211> LENGTH: 7
<212> TYPE: PRT
<213> ORGANISM: Homo sapiens

<400> SEQUENCE: 32

Glu Asp Asn Gln Arg Pro Ser
1               5

<210> SEQ ID NO 33
<211> LENGTH: 9
<212> TYPE: PRT
<213> ORGANISM: Homo sapiens

<400> SEQUENCE: 33

Gln Ser Tyr Asp Ser Ser His Leu Val
1               5

<210> SEQ ID NO 34
<211> LENGTH: 10
<212> TYPE: PRT
<213> ORGANISM: Homo sapiens

<400> SEQUENCE: 34

Gln Ser Tyr Ala Ser Ser Ser Leu Trp Val
1               5                   10

<210> SEQ ID NO 35
<211> LENGTH: 9
<212> TYPE: PRT
<213> ORGANISM: Homo sapiens

<400> SEQUENCE: 35

Met Gln Tyr Asp Ser Ser His Leu Val
1               5

<210> SEQ ID NO 36
<211> LENGTH: 9
<212> TYPE: PRT
<213> ORGANISM: Homo sapiens

<400> SEQUENCE: 36

Gln Ser Tyr Asp Phe His His Leu Val
1               5

<210> SEQ ID NO 37
<211> LENGTH: 9
<212> TYPE: PRT
<213> ORGANISM: Homo sapiens

<400> SEQUENCE: 37

Met Gln Tyr Asp Phe His His Leu Val
1               5

<210> SEQ ID NO 38
<211> LENGTH: 351
<212> TYPE: DNA
<213> ORGANISM: Homo sapiens

<400> SEQUENCE: 38
```

Preceding sequence start (SEQ ID NO 31 continued):

Glu Asp Asp Gln Arg Pro Ser
1               5

```
gaggtccagt tagtggagtc tgggggaggc ctggtcaagc cggggggggtc cctgagactc    60
```

```
tcctgtgcag cctctggatt cacctttgat gattctgtca tgcactgggt ccgtcaagct    120
ccggggaagg gtctggagtg ggtttctctt gttggttggg atggttttt tacatactat    180 gcagactcag tgaagggccg attcaccatc tccagagaca acgcgaagaa ctctctgtat    240
ctgcaaatga acagcctgag agccgaggac acggctgtgt attactgtgc agacaaggg    300 gattacatgg ggaacaactg gggccaggga accctggtca ccgtctcctc a             351
```

<210> SEQ ID NO 39
<211> LENGTH: 330
<212> TYPE: DNA
<213> ORGANISM: Homo sapiens

<400> SEQUENCE: 39

```
aatttttatgc tgactcagcc ccactctgtg tcggaatctc cgggaaagac ggtgaccatc    60
tcctgcaccc gcagcagtgg cagcattgac agttcctatg tgcagtggta ccagcagcgc   120
ccgggcagct cccccaccac tgtgatctat gaggatgacc aaagaccctc tggggtccct   180
gatcggttct ctggctccat cgacagctcc tccaactctg cctccctcac catctctgga   240
ctgaaaactg aggacgaggc tgactactac tgtcagtctt atgattttca tcatctggtg   300
ttcggcggag ggaccaagct gaccgtccta                                      330
```

<210> SEQ ID NO 40
<211> LENGTH: 117
<212> TYPE: PRT
<213> ORGANISM: Homo sapiens

<400> SEQUENCE: 40

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Asp Asp Ser
            20                  25                  30

Val Met His Trp Val Arg Gln Ala Pro Gly Lys Gly Leu Glu Trp Val
        35                  40                  45

Ser Leu Val Gly Trp Asp Gly Phe Phe Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Asp Tyr Met Gly Asn Asn Trp Gly Gln Gly Thr Leu
            100                 105                 110

Val Thr Val Ser Ser
        115
```

<210> SEQ ID NO 41
<211> LENGTH: 110
<212> TYPE: PRT
<213> ORGANISM: Homo sapiens

<400> SEQUENCE: 41

```
Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Asp Ser Ser
            20                  25                  30

Tyr Val Gln Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
```

```
                    50                  55                  60
Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp
                     85                  90                  95

His His Leu Val Phe Gly Gly Gly Thr Lys Leu Thr Val Leu
                100                 105                 110

<210> SEQ ID NO 42
<211> LENGTH: 432
<212> TYPE: PRT
<213> ORGANISM: Homo sapiens

<400> SEQUENCE: 42

Glu Val Gln Leu Val Glu Ser Gly Gly Gly Leu Val Lys Pro Gly
  1               5                  10                  15

Gly Ser Leu Arg Leu Ser Cys Ala Ala Ser Gly Phe Thr Phe Asp Asp Ser
                 20                  25                  30

Val Met His Trp Val Arg Gln Ala Pro Gly Lys Gly Leu Glu Trp Val
                 35                  40                  45

Ser Leu Val Gly Trp Asp Gly Phe Phe Thr Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Gly Asp Tyr Met Gly Asn Asn Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
                130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Ala Pro Glu Leu Leu Gly Gly Pro Ser
210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
                260                 265                 270

Lys Thr Lys Pro Arg Glu Glu Gln Tyr Asn Ser Thr Tyr Arg Val Val
                275                 280                 285

Ser Val Leu Thr Val Leu His Gln Asp Trp Leu Asn Gly Lys Glu Tyr
                290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
```

```
                    325                 330                 335
Pro Pro Ser Arg Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
            355                 360                 365

Asn Gly Gln Pro Glu Asn Asn Tyr Lys Thr Thr Pro Pro Val Leu Asp
            370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

<210> SEQ ID NO 43
<211> LENGTH: 215
<212> TYPE: PRT
<213> ORGANISM: Homo sapiens

<400> SEQUENCE: 43

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Asp Ser Ser
            20                  25                  30

Tyr Val Gln Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Phe
                85                  90                  95

His His Leu Val Phe Gly Gly Gly Thr Lys Leu Thr Val Leu Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 44
<211> LENGTH: 110
<212> TYPE: PRT
<213> ORGANISM: Homo sapiens

<400> SEQUENCE: 44

Asn Phe Met Leu Thr Gln Pro His Ser Val Ser Glu Ser Pro Gly Lys
1               5                   10                  15
```

```
Thr Val Thr Ile Ser Cys Thr Arg Ser Ser Gly Ser Ile Asp Ser Ser
            20                  25                  30

Tyr Val Gln Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
50                      55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Met Gln Tyr Asp Phe
                85                  90                  95

His His Leu Val Phe Gly Gly Gly Thr Lys Leu Thr Val Leu
            100                 105                 110

<210> SEQ ID NO 45
<211> LENGTH: 431
<212> TYPE: PRT
<213> ORGANISM: Homo sapiens

<400> SEQUENCE: 45

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asp Asp Ser
            20                  25                  30

Val Met His Trp Val Arg Gln Ala Pro Gly Lys Gly Leu Glu Trp Val
        35                  40                  45

Ser Leu Val Gly Trp Asp Gly Phe Phe Thr Tyr Tyr Ala Asp Ser Val
50                      55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Asp Tyr Met Gly Asn Asn Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                     135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Ala Pro Pro Val Ala Gly Pro Ser Val
210                     215                 220

Phe Leu Phe Pro Pro Lys Pro Lys Asp Thr Leu Met Ile Ser Arg Thr
225                 230                 235                 240

Pro Glu Val Thr Cys Val Val Val Asp Val Ser His Glu Asp Pro Glu
                245                 250                 255

Val Gln Phe Asn Trp Tyr Val Asp Gly Val Glu Val His Asn Ala Lys
            260                 265                 270

Thr Lys Pro Arg Glu Glu Gln Phe Asn Ser Thr Phe Arg Val Val Ser
        275                 280                 285
```

Val Leu Thr Val Val His Gln Asp Trp Leu Asn Gly Lys Glu Tyr Lys
        290                 295                 300

Cys Lys Val Ser Asn Lys Gly Leu Pro Ser Ser Ile Glu Lys Thr Ile
305                 310                 315                 320

Ser Lys Thr Lys Gly Gln Pro Arg Glu Pro Gln Val Tyr Thr Leu Pro
                325                 330                 335

Pro Ser Arg Glu Glu Met Thr Lys Asn Gln Val Ser Leu Thr Cys Leu
                340                 345                 350

Val Lys Gly Phe Tyr Pro Ser Asp Ile Ala Val Glu Trp Glu Ser Asn
                355                 360                 365

Gly Gln Pro Glu Asn Asn Tyr Lys Thr Thr Pro Pro Met Leu Asp Ser
        370                 375                 380

Asp Gly Ser Phe Phe Leu Tyr Ser Lys Leu Thr Val Asp Lys Ser Arg
385                 390                 395                 400

Trp Gln Gln Gly Asn Val Phe Ser Cys Ser Val Met His Glu Ala Leu
                405                 410                 415

His Asn His Tyr Thr Gln Lys Ser Leu Ser Leu Ser Pro Gly Lys
                420                 425                 430

<210> SEQ ID NO 46
<211> LENGTH: 7
<212> TYPE: PRT
<213> ORGANISM: Homo sapiens

<400> SEQUENCE: 46

Gly Phe Thr Phe Asp Asp Ser
1               5

<210> SEQ ID NO 47
<211> LENGTH: 10
<212> TYPE: PRT
<213> ORGANISM: Homo sapiens

<400> SEQUENCE: 47

Gly Phe Thr Phe Asp Asp Ser Val Met His
1               5                   10

<210> SEQ ID NO 48
<211> LENGTH: 6
<212> TYPE: PRT
<213> ORGANISM: Homo sapiens

<400> SEQUENCE: 48

Gly Trp Asp Gly Phe Phe
1               5

<210> SEQ ID NO 49
<211> LENGTH: 8
<212> TYPE: PRT
<213> ORGANISM: Homo sapiens

<400> SEQUENCE: 49

Gln Gly Asp Tyr Met Gly Asn Asn
1               5

<210> SEQ ID NO 50
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)

```
<223> OTHER INFORMATION: Xaa can be Asp or Asn
<220> FEATURE:
<221> NAME/KEY: MISC_FEATURE
<222> LOCATION: (2)..(2)
<223> OTHER INFORMATION: Xaa can be Ser or Tyr

<400> SEQUENCE: 50

Xaa Xaa Val Met His
1               5

<210> SEQ ID NO 51
<211> LENGTH: 17
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa can be Leu or Ala
<220> FEATURE:
<221> NAME/KEY: MISC_FEATURE
<222> LOCATION: (2)..(2)
<223> OTHER INFORMATION: Xaa can be Val or Ile
<220> FEATURE:
<221> NAME/KEY: MISC_FEATURE
<222> LOCATION: (3)..(3)
<223> OTHER INFORMATION: Xaa can be Gly or Ser
<220> FEATURE:
<221> NAME/KEY: MISC_FEATURE
<222> LOCATION: (4)..(4)
<223> OTHER INFORMATION: Xaa can be Trp or Gly
<220> FEATURE:
<221> NAME/KEY: MISC_FEATURE
<222> LOCATION: (5)..(5)
<223> OTHER INFORMATION: Xaa can be Asp or Ser
<220> FEATURE:
<221> NAME/KEY: MISC_FEATURE
<222> LOCATION: (7)..(7)
<223> OTHER INFORMATION: Xaa can be Phe, Gly or Ser
<220> FEATURE:
<221> NAME/KEY: MISC_FEATURE
<222> LOCATION: (8)..(8)
<223> OTHER INFORMATION: Xaa can be Phe, Ala or Ser

<400> SEQUENCE: 51

Xaa Xaa Xaa Xaa Xaa Gly Xaa Xaa Thr Tyr Tyr Ala Asp Ser Val Lys
1               5                   10                  15

Gly

<210> SEQ ID NO 52
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa can be Gln or Asp
<220> FEATURE:
<221> NAME/KEY: MISC_FEATURE
<222> LOCATION: (2)..(2)
<223> OTHER INFORMATION: Xaa can be Gly or Ile
<220> FEATURE:
<221> NAME/KEY: MISC_FEATURE
<222> LOCATION: (3)..(3)
<223> OTHER INFORMATION: Xaa can be Asp or Ser
<220> FEATURE:
<221> NAME/KEY: MISC_FEATURE
<222> LOCATION: (4)..(4)
<223> OTHER INFORMATION: Xaa can be Tyr or Gly
<220> FEATURE:
<221> NAME/KEY: MISC_FEATURE
<222> LOCATION: (5)..(5)
<223> OTHER INFORMATION: Xaa can be Met, Val or Gly
<220> FEATURE:
<221> NAME/KEY: MISC_FEATURE
<222> LOCATION: (6)..(6)
```

```
<223> OTHER INFORMATION: Xaa can be Gly or Phe
<220> FEATURE:
<221> NAME/KEY: MISC_FEATURE
<222> LOCATION: (7)..(7)
<223> OTHER INFORMATION: Xaa can be Asn, Asp or Met
<220> FEATURE:
<221> NAME/KEY: MISC_FEATURE
<222> LOCATION: (8)..(8)
<223> OTHER INFORMATION: Xaa can be Asn, Tyr or Asp

<400> SEQUENCE: 52

Xaa Xaa Xaa Xaa Xaa Xaa Xaa Xaa
1               5

<210> SEQ ID NO 53
<211> LENGTH: 13
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa can be Arg or Gly
<220> FEATURE:
<221> NAME/KEY: MISC_FEATURE
<222> LOCATION: (6)..(6)
<223> OTHER INFORMATION: Xaa can be Ser or Arg
<220> FEATURE:
<221> NAME/KEY: MISC_FEATURE
<222> LOCATION: (8)..(8)
<223> OTHER INFORMATION: Xaa can be Asp or Ala

<400> SEQUENCE: 53

Thr Xaa Ser Ser Gly Xaa Ile Xaa Ser Ser Tyr Val Gln
1               5                   10

<210> SEQ ID NO 54
<211> LENGTH: 7
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa can be Asp or Asn

<400> SEQUENCE: 54

Glu Asp Xaa Gln Arg Pro Ser
1               5

<210> SEQ ID NO 55
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa can be Gln or Met
<220> FEATURE:
<221> NAME/KEY: MISC_FEATURE
<222> LOCATION: (2)..(2)
<223> OTHER INFORMATION: Xaa can be Ser or Gln
<220> FEATURE:
<221> NAME/KEY: MISC_FEATURE
<222> LOCATION: (4)..(4)
<223> OTHER INFORMATION: Xaa can be Asp or Ala
<220> FEATURE:
<221> NAME/KEY: MISC_FEATURE
<222> LOCATION: (5)..(5)
<223> OTHER INFORMATION: Xaa can be Phe or Ser
<220> FEATURE:
<221> NAME/KEY: MISC_FEATURE
<222> LOCATION: (6)..(6)
<223> OTHER INFORMATION: Xaa can be His or Ser
<220> FEATURE:
<221> NAME/KEY: MISC_FEATURE
```

```
<222> LOCATION: (7)..(7)
<223> OTHER INFORMATION: Xaa can be His or Ser
<220> FEATURE:
<221> NAME/KEY: MISC_FEATURE
<222> LOCATION: (9)..(9)
<223> OTHER INFORMATION: Xaa can be Val or Trp

<400> SEQUENCE: 55

Xaa Xaa Tyr Xaa Xaa Xaa Xaa Leu Xaa
1               5

<210> SEQ ID NO 56
<211> LENGTH: 8
<212> TYPE: PRT
<213> ORGANISM: Homo sapiens

<400> SEQUENCE: 56

Phe Thr Phe Asp Asp Ser Val Met
1               5

<210> SEQ ID NO 57
<211> LENGTH: 6
<212> TYPE: PRT
<213> ORGANISM: Homo sapiens

<400> SEQUENCE: 57

Gly Trp Asp Gly Phe Phe
1               5

<210> SEQ ID NO 58
<211> LENGTH: 6
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid

<400> SEQUENCE: 58

Ala Arg Xaa Xaa Xaa Xaa
1               5

<210> SEQ ID NO 59
<211> LENGTH: 8
<212> TYPE: PRT
<213> ORGANISM: Homo sapiens

<400> SEQUENCE: 59

Ser Gly Ser Ile Asp Ser Ser Tyr
1               5

<210> SEQ ID NO 60
<211> LENGTH: 9
<212> TYPE: PRT
<213> ORGANISM: Homo sapiens

<400> SEQUENCE: 60
```

```
Glu Asp Asp Gln Arg Pro Ser Gly Val
1               5

<210> SEQ ID NO 61
<211> LENGTH: 4
<212> TYPE: PRT
<213> ORGANISM: Homo sapiens

<400> SEQUENCE: 61

Phe His His Leu
1
```

US 8,298,535 B2

ANTI-IL-7 RECEPTOR ANTIBODIES

This application claims priority, under 35 USC §119(e), to U.S. Provisional Application Ser. No. 61/307,670, filed Feb. 24, 2010, and U.S. Provisional Application Ser. No. 61/438,205, filed Jan. 31, 2011, hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "SequenceListingPC33990A.txt" created on Feb. 3, 2011 and having a size of 41 KB. The sequence listing contained in this .txt file is part of the specification and is herein incorporated by reference in its entirety.

FIELD

The present invention relates to antibodies, e.g., full length antibodies or antigen-binding portions thereof, that antagonize the activity of interleukin-7 receptor (IL-7R), including its interaction with IL-7. The invention further relates to compositions comprising an IL-7R antagonist, such as an antagonist IL-7R antibody, and methods of using the IL-7R antagonist as a medicament. The IL-7R antagonist can be used in the prevention and/or treatment of type 2 diabetes, graft-versus-host disease (GVHD), and autoimmune disorders, including type 1 diabetes, multiple sclerosis, rheumatoid arthritis, and lupus.

BACKGROUND

The IL-7R complex is a heterodimeric receptor made up of the IL-7R alpha chain (IL-7Rα) and the common gamma chain (γc) (Mazzucchelli et al., Nat Rev Immunol., 2007, 7:144-54). IL-7R is bound by interleukin-7 (IL-7), a cytokine essential to the development and homeostatic maintenance of T and B lymphocytes (Fry et al., J. Immunol., 2005, 174: 6571-6). Binding of IL-7 to IL-7R activates multiple pathways that regulate lymphocyte survival, glucose uptake, proliferation and differentiation.

IL-7R is expressed on both dendritic cells and monocytes and appears to act in multiple hematopoietic lineages (Reche P A, et al., J. Immunol., 2001, 167:336-43). In dendritic cells, IL-7R plays an immunomodulatory role, whereas lymphocytes require IL-7R signaling for survival, proliferation and differentiation. Both the Jak-Stat and PI3K-Akt pathways are activated by the binding of IL-7 to IL-7R (Jian et al., Cytokine Growth Factor Rev., 2005, 16:513-533). These pathways involve signaling crosstalk, shared interaction domains, feedback loops, integrated gene regulation, mulitimerization and ligand competition. Some targets of IL-7 signaling, including Bcl2 and Pyk2, contribute to cellular survival. Other targets, such as PI3 kinase, src family kinases (lck and fyn) and STAT5, contribute to cellular proliferation. The transcription factor STAT5 contributes to activation of multiple different downstream genes in B and T cells and may contribute to VDJ recombination through alteration of chromatin structure. The cell survival and cell proliferation signals induced by IL-7 combine to induce normal T cell development. Details of the complex IL-7 signaling network and its interaction with other signaling cascades in cells of the immune system have not yet been fully elucidated.

From the information available in the art, and prior to the present invention, it remained unclear whether the introduction of an antagonist IL-7R antibody into the blood circulation to selectively antagonize IL-7R would be effective to treat type 2 diabetes, type 1 diabetes, GVHD, lupus and rheumatoid arthritis, and, if so, what properties of an IL-7R antibody are needed for such in vivo effectiveness.

SUMMARY

Antagonist antibodies that selectively interact with and inhibit IL-7R function are provided. It is demonstrated for the first time that certain antagonist IL-7R antibodies are effective in vivo to treat type 1 diabetes, type 2 diabetes, rheumatoid arthritis, GVHD and lupus.

In some embodiments, antagonist antibodies that selectively interact with and inhibit IL-7R function are provided. In some embodiments, the antibody specifically binds to IL-7R and comprises an antigen binding region that competes with a monoclonal antibody selected from the group consisting of C1GM, C2M3, P3A9, P4B3, P2D2, P2E11, HAL403a and HAL403b, for binding to IL-7R. In some embodiments, the antibody comprises a polypeptide having the amino acid sequence shown in SEQ ID NO: 42 or SEQ ID NO: 43. In other embodiments, the antibody specifically binds to IL-7R and recognizes an epitope which overlaps an epitope of IL-7R that is recognized by a monoclonal antibody selected from the group consisting of C1GM, C2M3, P3A9, P4B3, P2D2, P2E11, HAL403a and HAL403b. In some embodiments, the antibody the antibody binds to an epitope comprising residues I82, K84, K100, T105, and Y192 of interleukin-7 receptor alpha (IL-7Rα). In some embodiments, the epitope further comprises one or more additional residues selected from the group consisting of residues D190, H191, and K194 of human IL-7Rα.

In some embodiments, the IL-7R is human IL-7Rα.

In some embodiments, the antibody specifically binds to interleukin-7 receptor alpha (IL-7Rα) and comprises a heavy chain variable region (VH) complementary determining region one (CDR1) having the amino acid sequence $X_1X_2$VMH, wherein $X_1$ is D or N; $X_2$ is S or Y (SEQ ID NO: 50), a VH CDR2 having the amino acid sequence $X_1X_2X_3X_4X_5GX_6X_7$TYYADSVKG, wherein $X_1$ is L or A; $X_2$ is V or I; $X_3$ is G or S; $X_4$ is W or G; $X_5$ is D or S; $X_6$ is F, G or S; $X_7$ is F, A or S (SEQ ID NO: 51), and a VH CDR3 having the amino acid sequence $X_1X_2X_3X_4X_5X_6X_7X_8$, wherein $X_1$ is Q or D; $X_2$ is G or I; $X_3$ is D or S; $X_4$ is Y or G; $X_5$ is M, V or G; $X_6$ is G or F; $X_7$ is N, D or M; $X_8$ is N, Y or D (SEQ ID NO: 52), a light chain variable region (VL) CDR1 having the amino acid sequence $TX_1SSGX_2$$_1X_3$SSYVQ wherein $X_1$ is R or G; $X_2$ is S or R; $X_3$ is D or A (SEQ ID NO: 53), a VL CDR2 having the amino acid sequence $EDX_1$QRPS wherein $X_1$ is D or N (SEQ ID NO: 54), and a VL CDR3 having the amino acid sequence $X_1X_2YX_3X_4X_5X_6LX_7$ wherein $X_1$ is Q or M; $X_2$ is S or Q; $X_3$ is D or A; $X_4$ is F or S; $X_5$ is H or S; $X_6$ is H or S; $X_7$ is V or W (SEQ ID NO: 55), wherein the antibody blocks STAT5 phosphorylation in a STAT5 activation assay. In some embodiments, the framework region between VH CDR2 and VH CDR3 comprises the amino acid sequence alanine-arginine, wherein the arginine is adjacent to the first amino acid residue of VH CDR3. In some embodiments, the framework region between VH CDR2 and VH CDR3 comprises the amino acid sequence cysteine-alanine-arginine, wherein the arginine is adjacent to the first amino acid residue of VH CDR3.

In some embodiments, the antibody specifically binds to IL-7Rα and comprises a heavy chain variable region (VH) comprising the following complementarity determining regions (CDRs): a VH CDR1 that is a VH CDR1 in SEQ ID NO: 40; a VH CDR2 that is a VH CDR2 in SEQ ID NO: 40; and a VH CDR3 that is a VH CDR3 in SEQ ID NO: 40. In some embodiments, the antibody specifically binds to IL-7Rα and comprises a light chain variable region (VL) comprising the following CDRs: a VL CDR1 that is a VL CDR1 in SEQ ID NO: 41; a VL CDR2 that is a VL CDR2 in SEQ ID NO: 41; and a VL CDR3 that is a VL CDR3 in SEQ ID NO: 41. In some embodiments, the antibody specifically binds to IL-7Rα and comprises: a heavy chain variable region (VH) comprising the following complementarity determining regions (CDRs): a VH CDR1 that is a VH CDR1 in SEQ ID NO: 40; a VH CDR2 that is a VH CDR2 in SEQ ID NO: 40; and a VH CDR3 that is a VH CDR3 in SEQ ID NO: 40; and a light chain variable region (VL) comprising the following CDRs: a VL CDR1 that is a VL CDR1 in SEQ ID NO: 41; a VL CDR2 that is a VL CDR2 in SEQ ID NO: 41; and a VL CDR3 that is a VL CDR3 in SEQ ID NO: 41. In some embodiments, each CDR is defined in accordance with the Kabat definition, the Chothia definition, the combination of the Kabat definition and the Chothia definition, the AbM definition, or the contact definition of CDR.

In some embodiments, the antibody comprises a VH CDR1 having the amino acid sequence $X_1X_2$VMH, wherein $X_1$ is D or N; $X_2$ is S or Y (SEQ ID NO: 50), a VH CDR2 having the amino acid sequence GWDGFF (SEQ ID NO: 57), and a VH CDR3 having the amino acid sequence AR$X_1X_2X_3X_4$ (SEQ ID NO: 58), a VL CDR1 having the amino acid sequence SGSIDSSY (SEQ ID NO: 59), a VL CDR2 having the amino acid sequence EDDQRPSGV (SEQ ID NO: 60), and a VL CDR3 having the amino acid sequence FHHL (SEQ ID NO: 61), wherein the antibody blocks STAT5 phosphorylation in a STAT5 activation assay.

In some embodiments, the antibody specifically binds to IL-7Rα and comprises a heavy chain variable region (VH) complementary determining region one (CDR1) having the amino acid sequence DSVMH (SEQ ID NO: 19), GFTFDDS (SEQ ID NO: 46), or GFTFDDSVMH (SEQ ID NO: 47), a VH CDR2 having the amino acid sequence LVGWDGFFTYYADSVKG (SEQ ID NO: 23) or GWDGFF (SEQ ID NO: 48), and a VH CDR3 having the amino acid sequence QGDYMGNN (SEQ ID NO: 49), or a variant thereof having one or more conservative amino acid substitutions in CDR1, CDR2, and/or CDR3.

In some embodiments, the antibody comprises a light chain variable region (VL) CDR1 having the amino acid sequence TRSSGSIDSSYVQ (SEQ ID NO: 29), a VL CDR2 having the amino acid sequence EDDQRPS (SEQ ID NO: 31), and/or VL CDR3 having the amino acid sequence QSYDFHHLV (SEQ ID NO: 36), or a variant thereof having one or more conservative amino acid substitutions in CDR1, CDR2, and/or CDR3. In some embodiments, the antibody further comprises a VH CDR1 having the amino acid sequence shown in SEQ ID NO: 19, 46 or 47, a VH CDR2 having the amino acid sequence shown in SEQ ID NO: 23, or 48, and a VH CDR3 having the amino acid sequence shown in SEQ ID NO: 49, or a variant thereof having one or more conservative amino acid substitutions in CDR1, CDR2, and/or CDR3.

In some embodiments, the antibody specifically binds to IL-7Rα and comprises a heavy chain variable region (VH) complementary determining region one (CDR1) having the amino acid sequence shown in SEQ ID NO: 19, 46 or 47, a VH CDR2 having the amino acid sequence shown in SEQ ID NO: 23, or 48, and a VH CDR3 having the amino acid sequence shown in SEQ ID NO: 49, a light chain variable region (VL) CDR1 having the amino acid sequence shown in SEQ ID NO: 29, a VL CDR2 having the amino acid sequence shown in SEQ ID NO: 31, and a VL CDR3 having the amino acid sequence shown in SEQ ID NO: 36. In some embodiments, the VH region comprises the amino acid sequence EVQLVESGGGLVKPGGSLRLSCAASGFTFDDSVMHWVRQAPGKGLEWVSLVGWDG FFTYYADSVKGRFTISRDNAKNSLYLQMNSLRAEDTAVYYCARQGDYMGNNWGQGTL VTVSS (SEQ ID NO: 40) and the VL region comprises the amino acid sequence NFMLTQPHSVSESPGKTVTISCTRSSGSIDSSYVQWYQQRPGSSPTTVIYEDDQRPSG VPDRFSGSIDSSSNSASLTISGLKTEDEADYYCQSYDFHHLVFGGGTKLTVL (SEQ ID NO: 41). In some embodiments, the antibody comprises a light chain having the amino acid sequence NFMLTQPHSVSESPGKTVTISCTRSSGSIDSSYVQWYQQRPGSSPTTVIYEDDQRPSG VPDRFSGSIDSSSNSASLTISGLKTEDEADYYCQSYDFHHLVFGGGTKLTVLQPKAAPS VTLFPPSSEELQANKATLVCLISDFYPGAVTVAWKADSSPVKAGVETTTPSKQSNNKY AASSYLSLTPEQWKSHRSYSCQVTHEGSTVEKTVAPTECS (SEQ ID NO: 43) and a heavy chain having the amino acid sequence EVQLVESGGGLVKPGGSLRLSCAASGFTFDDSVMHWVRQAPGKGLEWVSLVGWDG FFTYYADSVKGRFTISRDNAKNSLYLQMNSLRAEDTAVYYCARQGDYMGNNWGQGTL VTVSSASTKGPSVFPLAPSSKSTSGGTAALGCLVKDYFPEPVTVSWNSGALTSGVHTF PAVLQSSGLYSLSSVVTVPSSSLGTQTYICNVNHKPSNTKVDKKVAPELLGGPSVFLFP PKPKDTLMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPPSREEMT KNQVSLTCLVKGFYPSDIAVEWESNGQPENNYKTTPPVLDSDGSFFLYSKLTVDKSRW QQGNVFSCSVMHEALHNHYTQKSLSLSPGK (SEQ ID NO: 42), with or without the C-terminal lysine of SEQ ID NO: 42.

In some embodiments, the antibody can be a human antibody, a humanized antibody, or a chimeric antibody. In some embodiments, the antibody is a monoclonal antibody.

In some embodiments, the antibody comprises a constant region. In some embodiments, the antibody is of the human IgG1 or IgG2Δa subclass. In some embodiments, the antibody comprises a glycosylated constant region. In some embodiments, the antibody comprises a constant region having increased binding affinity to a human Fc gamma receptor. In some embodiments, the antibody comprises an aglycosylated constant region.

In some embodiments, a pharmaceutical composition comprising an antibody that selectively interacts with and inhibits IL-7R function is provided.

In some embodiments, a cell line that recombinantly produces an antibody that selectively interacts with and inhibits IL-7R function is provided.

In some embodiments, a nucleic acid encoding an antibody that selectively interacts with and inhibits IL-7R function is provided.

In some embodiments, methods of lowering blood glucose levels in an individual are provided. In some embodiments, the method comprises administering a therapeutically effective amount of an antagonist IL-7R antibody to an individual in need of such treatment, thereby lowering blood glucose levels.

In some embodiments, methods of improving glucose tolerance in an individual are provided. In some embodiments, the method comprises administering a therapeutically effective amount of an antagonist IL-7R antibody to an individual in need of such treatment, thereby improving glucose tolerance.

In some embodiments, methods of preventing or treating type 1 diabetes in an individual are provided. In some embodiments, the method comprises administering a therapeutically effective amount of an antagonist IL-7R antibody to an individual in need of such treatment, thereby preventing or treating one or more symptoms of type 1 diabetes.

In some embodiments, methods of preventing or treating type 2 diabetes in an individual are provided. In some embodiments, the method comprises administering a therapeutically effective amount of an IL-7R antagonist to an individual in need of such treatment, thereby preventing or treating one or more symptoms of type 2 diabetes. In some embodiments, the IL-7R antagonist is an antagonist IL-7R antibody.

In some embodiments, methods of preventing or treating rheumatoid arthritis in an individual are provided. In some embodiments, the method comprises administering a therapeutically effective amount of an antagonist IL-7R antibody to an individual in need of such treatment, thereby preventing or treating one or more symptoms of rheumatoid arthritis.

In some embodiments, methods of preventing or treating graft-versus-host disease (GVHD) in an individual are provided. In some embodiments, the method comprises administering a therapeutically effective amount of an antagonist IL-7R antibody to an individual in need of such treatment, thereby preventing or treating one or more symptoms of GVHD.

In some embodiments, the GVHD is chronic GVHD or acute GVHD.

In some embodiments, methods of preventing or treating lupus in an individual are provided. In some embodiments, the method comprises administering a therapeutically effective amount of an antagonist IL-7R antibody to an individual in need of such treatment, thereby preventing or treating one or more symptoms of lupus.

In some embodiments, the lupus is cutaneous lupus erythematosus, systemic lupus erythematosus, drug-induced erythematosus or neonatal lupus.

In some embodiments, methods of preventing or treating multiple sclerosis in an individual are provided. In some embodiments, the method comprises administering a therapeutically effective amount of an antagonist IL-7R antibody to an individual in need of such treatment, thereby preventing or treating one or more symptoms of multiple sclerosis and reducing and/or depleting the naïve and/or activated T cell populations in the individual. In some embodiments, the reduced or depleted T cell populations in the individual comprise $T_H1$ and/or $T_H17$ cells. In some embodiments, administration of the antagonist IL-7R antibody does not result in expansion of $T_H17$ cell population in the individual.

In some embodiments, the antibody can be administered parenterally. In some embodiments, the individual is a human.

BRIEF DESCRIPTION OF THE
FIGURES/DRAWINGS

FIG. 5 depicts the effect of antagonist IL-7R monoclonal antibody 28G9 on naive CD4+ T cell population in NOD mice. For the x-axis, the total CD4+ T cell population was set as 100%.

FIG. 6 depicts the effect of antagonist IL-7R monoclonal antibodies 28B6 and 28G9 on clinical severity of EAE animals. Clinical severity of EAE was assessed daily with a 0 to 5 point scoring system: 0, normal; 1, flaccid tail; 2, partial hind-limb paralysis; 3, total hind-limb paralysis; 4, quadriplegia; 5, moribund state or dead.

FIG. 10 depicts the effect of antagonist IL-7R monoclonal antibody 28G9 at lower dose in animals with established EAE.

Figure 11A:
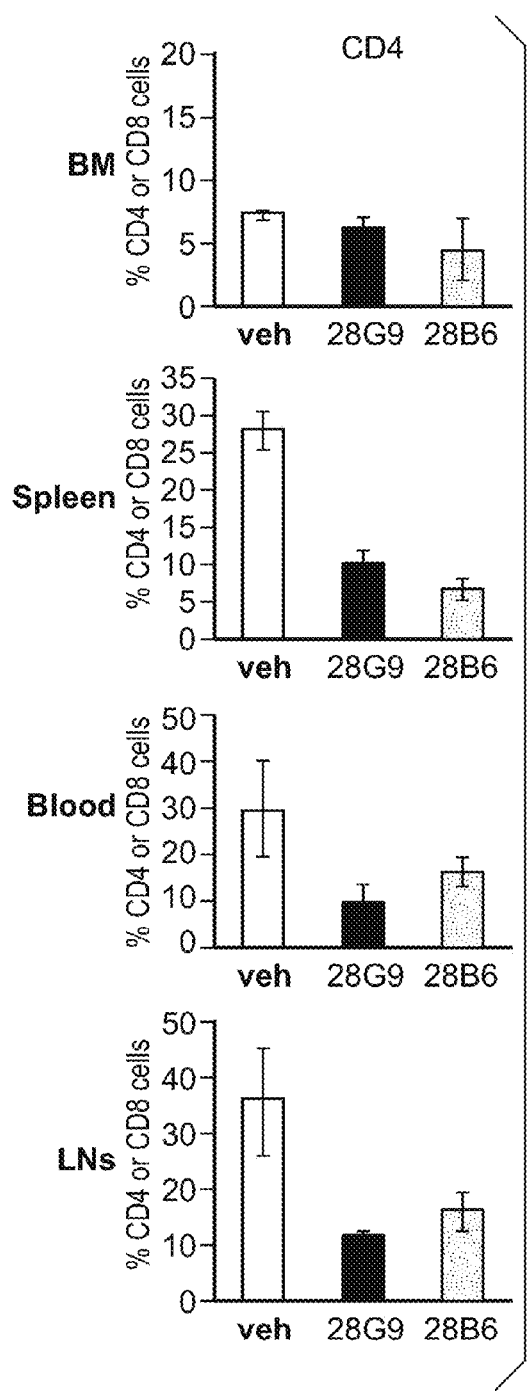
Figure 11B:
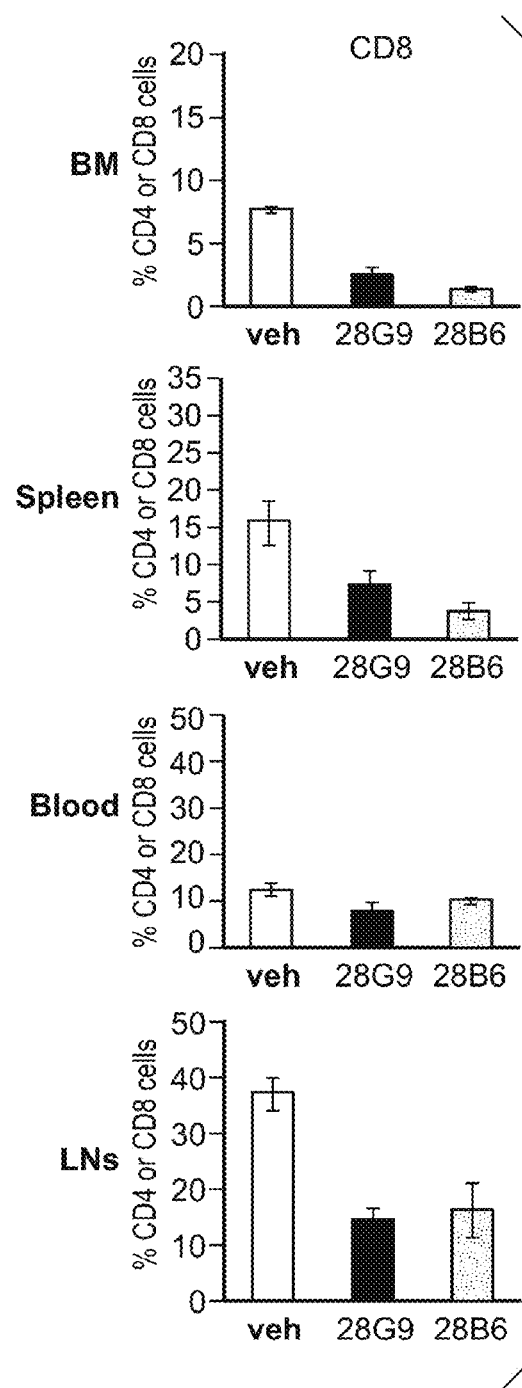

FIGS. 11A-B depict the effect of antagonist IL-7R monoclonal antibodies 28G9 and 28B6 on (A) CD4 T cell and (B) CD8 T cell populations from bone marrow (BM), spleen, blood and lymph nodes (LNs) of EAE animals. For the x-axis, the total lymphocyte population was set as 100%.

Figure 12A:
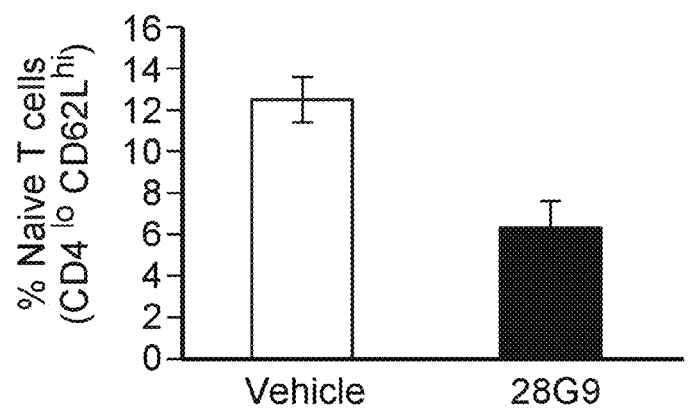
Figure 12B:
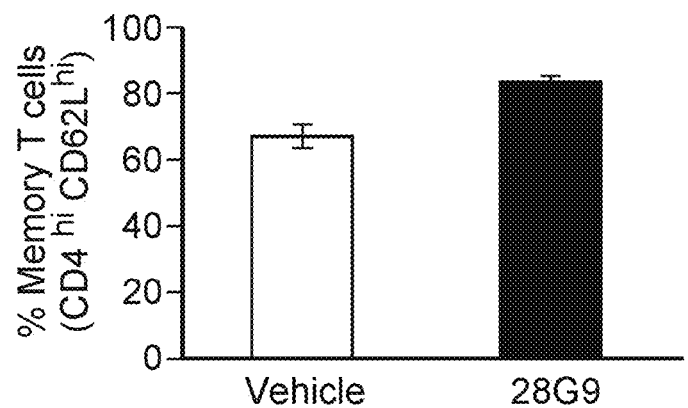
Figure 12C:
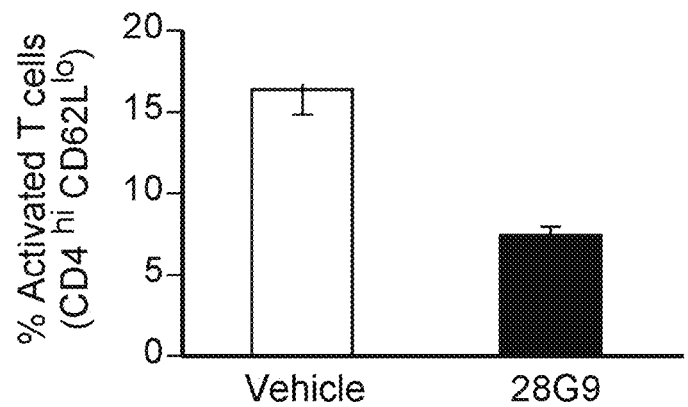

FIGS. 12A-C depict the effect of antagonist IL-7R monoclonal antibody 28G9 on (A) naive T cell, (B) memory T cell, and (C) activated T cell populations from bone marrow, spleen, blood and lymph nodes of EAE animals. For the x-axis, the CD8+ T cell population was set as 100%.

Figure 13:
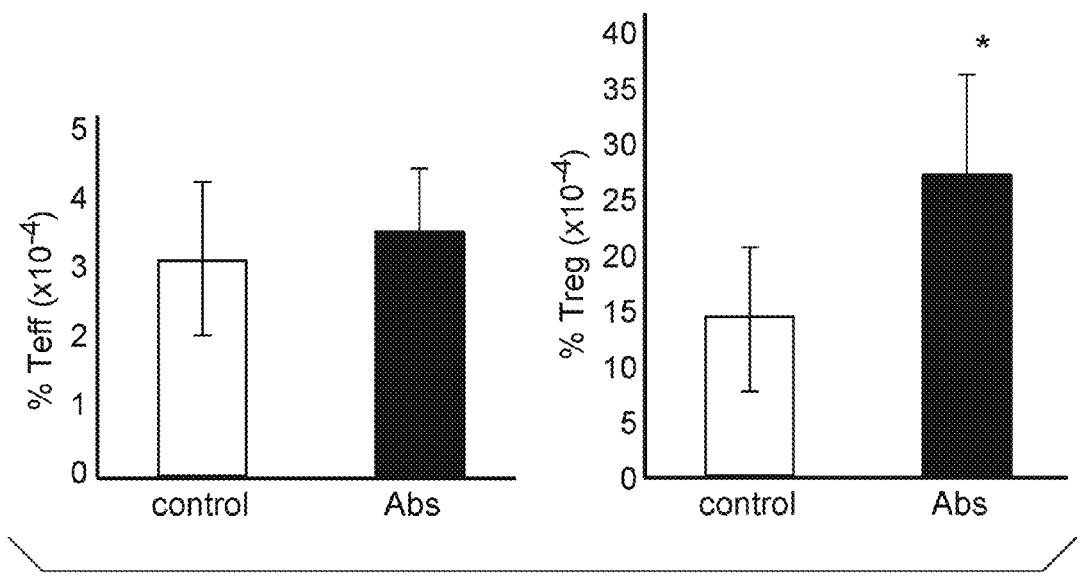

FIG. 13 depicts the effect of antagonist IL-7R monoclonal antibody 28G9 on $T_{eff}$ cell (left graph) and $T_{reg}$ cell (right graph) populations from bone marrow, spleen, blood and lymph nodes of EAE animals. For the x-axis, the CD4+ T cell population was set as 100%. "*" indicates P<0.05 as compared to control.

Figure 14:
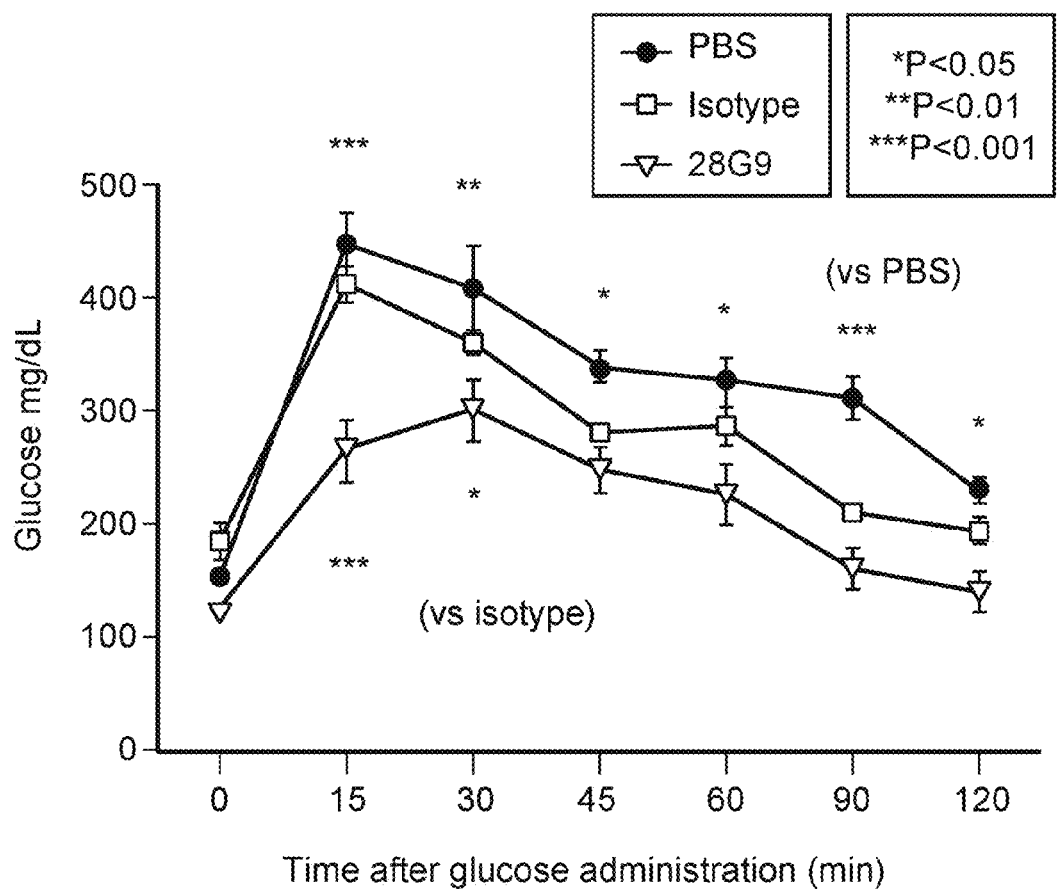

FIG. 14 depicts the effect of antagonist IL-7R monoclonal antibody 28G9 on blood glucose levels (mg/dL) in high fat diet-induced obesity (D10) mice.

Figure 15:
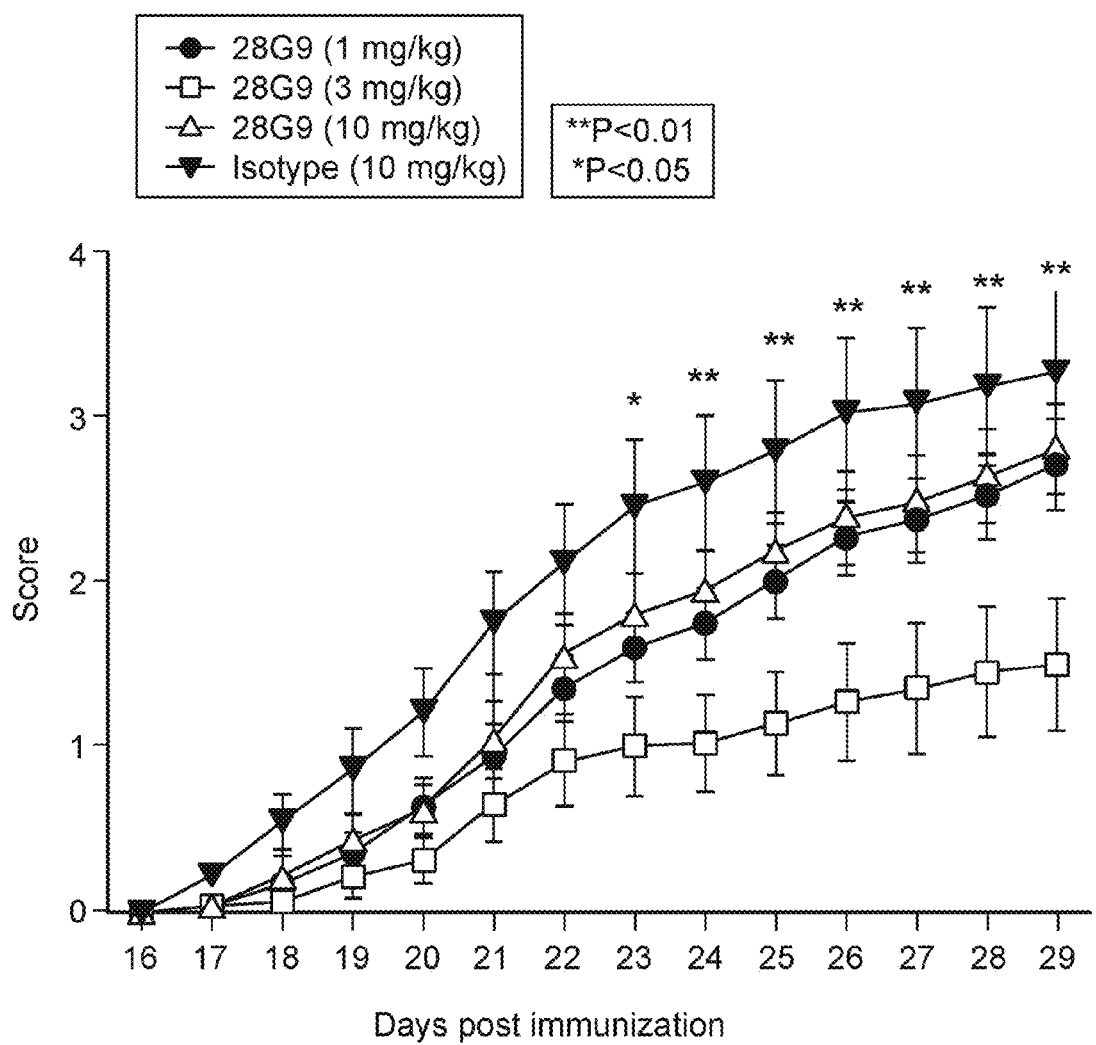

FIG. 15 depicts the effect of antagonist IL-7R monoclonal antibody 28G9 on glucose intolerance in high fat diet-induced obesity (D10) mice.

DETAILED DESCRIPTION

Disclosed herein are antibodies that antagonize the function of IL-7R, including its interaction with IL-7. Methods of making antagonist IL-7R antibodies, compositions comprising these antibodies, and methods of using these antibodies as a medicament are provided. IL-7R antagonists, e.g., antagonist IL-7R antibodies, can be used to in the prevention and/or treatment of type 2 diabetes, GVHD and autoimmune disorders, including multiple sclerosis (MS), rheumatoid arthritis, type 1 diabetes, and lupus.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

DEFINITIONS

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', $F(ab')_2$, Fv), single chain (ScFv) and domain antibodies (including, for example, shark and camelid antibodies), and fusion proteins comprising an antibody, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

As used herein, "humanized" antibody refers to forms of non-human (e.g. murine) antibodies that are chimeric immunoglobulins, immunoglobulin chains, or fragments thereof (such as Fv, Fab, Fab', $F(ab')_2$ or other antigen-binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, Proc. Natl. Acad. Sci. (USA) 95:6157-6162; Hoogenboom and Winter, 1991, J. Mol. Biol., 227:381; Marks et al., 1991, J. Mol. Biol., 222:581). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al. Monoclonal Antibodies and Cancer Therapy, Alan R. Liss, p. 77, 1985; Boerner et al., 1991, J. Immunol., 147 (1):86-95; and U.S. Pat. No. 5,750,373.

As used herein, the term "IL-7R" refers to any form of IL-7R and variants thereof that retain at least part of the activity of IL-7R. Unless indicated differently, such as by specific reference to human IL-7R, IL-7R includes all mammalian species of native sequence IL-7R, e.g., human, canine, feline, equine, and bovine.

As used herein, an "IL-7R antagonist" refers to an antibody or molecule that is able to inhibit IL-7R biological activity and/or downstream pathway(s) mediated by IL-7R signaling, including binding to IL-7, phosphorylation of STAT5, Src kinases, PI3 kinase and Pyk2, and upregulation of Bcl2 protein. Examples of IL-7R antagonists include, without limitation, antagonist IL-7R antibodies, IL-7R siRNA, IL-7R shRNA, and IL-7R antisense oligonucleotides.

Antagonist IL-7R antibodies encompass antibodies that block, antagonize, suppress or reduce (to any degree including significantly) IL-7R biological activity, including downstream pathways mediated by IL-7R signaling, such interaction with IL-7 and/or elicitation of a cellular response to IL-7. For purpose of the present invention, it will be explicitly understood that the term "antagonist IL-7R antibody" (interchangeably termed "IL-7R antagonist antibody," "antagonist anti-IL-7R antibody" or "anti-IL-7R antagonist antibody") encompasses all the previously identified terms, titles, and functional states and characteristics whereby the IL-7R itself, an IL-7R biological activity (including but not limited to interaction with IL-7, its ability to mediate any aspect of phosphorylation of STAT5, phosphatidylinositol-3-kinase (PI3K)-Akt pathway activation, $p27^{Kip1}$ downregulation, Bcl-2 upregulation, Rb hyperphosphorylation, and CXCR4 upregulation), or the consequences of the biological activity, are substantially nullified, decreased, or neutralized in any meaningful degree. In some embodiments, an antagonist IL-7R antibody binds IL-7R and prevents interaction with IL-7. Examples of antagonist IL-7R antibodies are provided herein.

As used herein a "full antagonist" is an antagonist which, at an effective concentration, essentially completely blocks a measurable effect of IL-7R. By a partial antagonist is meant an antagonist that is capable of partially blocking a measurable effect, but that, even at a highest concentration is not a full antagonist. By essentially completely is meant at least about 80%, preferably, at least about 90%, more preferably, at least about 95%, and most preferably, at least about 98% of the measurable effect is blocked.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

As known in the art a "constant region" of an antibody refers to the constant region of the antibody light chain or the constant region of the antibody heavy chain, either alone or in combination.

As used herein, an antibody "interacts with" IL-7R when the equilibrium dissociation constant is equal to or less than 20 nM, preferably less than about 6 nM, more preferably less than about 1 nM, most preferably less than about 0.2 nM, as measured by the methods disclosed herein in Example 2.

An epitope that "preferentially binds" or "specifically binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an IL-7R epitope is an antibody that binds this epitope with greater affinity, avidity, more readily, and/or with greater duration than it binds to other IL-7R epitopes or non-IL-7R epitopes. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant regions, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, "treatment" is an approach for obtaining beneficial or desired clinical results. For purposes of this invention, beneficial or desired clinical results include, but are not limited to, one or more of the following: enhancement of glucose clearance, lowering blood glucose levels, improving glucose tolerance, reducing incidence of high blood glucose levels resulting from type 1 or type 2 diabetes, reducing incidence or amelioration of one or more symptoms of rheumatoid arthritis, reducing incidence or amelioration of one or more symptoms of GVHD, reducing incidence or amelioration of one or more symptoms of lupus, and reducing incidence or amerlioration of one or more symptoms of multiple sclerosis.

"Reducing incidence" means any of reducing severity (which can include reducing need for and/or amount of (e.g., exposure to) other drugs and/or therapies generally used for this condition. As is understood by those skilled in the art, individuals may vary in terms of their response to treatment, and, as such, for example, a "method of reducing incidence" reflects administering the IL-7R antagonist based on a reasonable expectation that such administration may likely cause such a reduction in incidence in that particular individual.

"Ameliorating" means a lessening or improvement of one or more symptoms as compared to not administering an IL-7R antagonist. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing blood glucose levels, reducing incidence or amelioration of one or more symptoms of type 1 diabetes, type 2 diabetes, rheumatoid arthritis, GVHD, lupus or multiple sclerosis, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$k_{on}$", as used herein, refers to the rate constant for association of an antibody to an antigen. Specifically, the rate constants ($k_{on}$ and $k_{off}$) and equilibrium dissociation constants are measured using Fab antibody fragments (i.e. univalent) and 1 L-7R.

The term "$k_{off}$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the present invention. The materials, methods, and examples are illustrative only and not intended to be limiting.

Methods for Preventing or Treating Type 2 Diabetes, GVHD and Autoimmune Disorders In one aspect, the invention provides a method for treating or preventing type 2 diabetes in an individual comprising administering to the individual an effective amount of an IL-7R antagonist such as, for example, an antagonist IL-7R antibody. In another aspect, the invention provides a method for treating or preventing an autoimmune disease, such as type 1 diabetes, rheumatoid arthritis, lupus or multiple sclerosis, in an individual, the method comprising administering to the individual an effective amount of an IL-7R antagonist. In another aspect, the invention provides a method for treating or preventing GVHD in an individual comprising administering to the individual an effective amount of an IL-7R antagonist.

In some embodiments, therapeutic administration of the IL-7R antagonist advantageously results in lower blood glucose level and improved glucose tolerance. In other embodiments, therapeutic administration of the IL-7R antagonist advantageously maintains blood glucose at desirable levels.

In some embodiments, therapeutic administration of the IL-7R antagonist advantageously results in reduced incidence and/or amelioration of one or more symptoms of rheumatoid arthritis including, for example without limitation, joint stiffness, joint swelling, joint pain, and joint redness and warmth.

In some embodiments, therapeutic administration of the IL-7R antagonist advantageously results in reduced incidence and/or amelioration of one or more symptoms of lupus including, for example without limitation, fatigue, fever, weight loss, weight gain, joint pain, joint stiffness, joint swelling, malar rash, skin lesions, mouth sores, nose ulcers, hair loss, Raynaud's phenomenon, shortness of breath, chest pain, dry eyes, bruising, anxiety, depression and memory loss.

In some embodiments, therapeutic administration of the IL-7R antagonist advantageously results in reduced incidence and/or amelioration of one or more symptoms of multiple sclerosis including, for example without limitation, limb paralysis, tremors, difficulty walking, swallowing difficulties, blindness, blurring vision, and muscle weakness.

In some embodiments, therapeutic administration of the IL-7R antagonist advantageously results in reduced incidence and/or amelioration of one or more symptoms of GVHD including, for example without limitation, abdominal pain, abdominal cramps, fever, jaundice, skin rash, vomiting, weight loss, dry eyes, dry mouth, hair loss, hepatitis, lung disorders, and digestive tract disorders.

In some embodiments, therapeutic administration of the IL-7R antagonist advantageously results in reduced incidence and/or amelioration of one or more symptoms of acute GVHD including, for example without limitation, pneumonitis, intestinal inflammation, diarrhea, abdominal pain, abdominal cramps, fever, jaundice, nausea, vomiting, liver damage, skin rash, skin damage, damage to the mucosa, sloughing of the mucosal membrane, damage to the gastrointestinal tract, weight loss, maculopapular rash, elevated bilirubin levels, morbidity and mortality.

In some embodiments, therapeutic administration of the IL-7R antagonist advantageously results in reduced incidence and/or amelioration of one or more symptoms of chronic GVHD including, for example without limitation, dry eyes, dry mouth, hair loss, hepatitis, lung disorders, digestive tract disorders, skin rash, oral ulcer, oral atrophy, onchodystrophy, sicca syndrome, sclerosis, lichen-planus-like lesions, poikiloderma, esophageal webs, fasciitis and bronchiolitis obliterans, and damage to the liver, skin and mucosa, connective tissue, exocrine glands and/or the gastrointestinal tract.

A diabetic individual requiring lower blood glucose levels can be treated with an IL-7R antagonist such as, for example, an antagonist IL-7R antibody. An individual suitable for antibody therapy is selected using clinical criteria and prognostic indicators of diabetes that are well known in the art. An individual at risk of developing diabetes as assessed by known prognostic indicators such as family history, fasting blood glucose levels, or decreased glucose tolerance also warrants administration of an IL-7R antagonist. One skilled in the art would recognize or know how to diagnose an individual with diabetes or disregulated glucose uptake and, depending upon the degree or severity of the disease, can make the appropriate determination of when to administer the antibody and can also select the most desirable mode of administration.

An individual suffering from rheumatoid arthritis can be treated with an IL-7R antagonist such as, for example, an antagonist IL-7R antibody. An individual suitable for IL-7R antagonist therapy is selected using clinical criteria and prognostic indicators of rheumatoid arthritis that are well known in the art. Diagnosis or assessment of rheumatoid arthritis is well-established in the art. Assessment of severity may be performed based on measures known in the art, such as the rheumatoid arthritis severity scale (RASS). Bardwell et al., Rheumatology, 2002, 41:38-45. In some embodiments, ameliorating, controlling, reducing incidence of, or delaying the development or progression of rheumatoid arthritis and/or symptoms of rheumatoid arthritis is measured by RASS.

An individual suffering from lupus can be treated with an IL-7R antagonist such as, for example, an antagonist IL-7R antibody. An individual suitable for IL-7R antagonist therapy is selected using clinical criteria and prognostic indicators of lupus that are well known in the art. One skilled in the art would recognize or know how to diagnose an individual with lupus and, depending upon the degree or severity of the disease, can make the appropriate determination of when to administer the IL-7R antagonist and can also select the most desirable mode of administration.

An individual suffering from multiple sclerosis can be treated with an IL-7R antagonist such as, for example, an antagonist IL-7R antibody. An individual suitable for IL-7R antagonist therapy is selected using clinical criteria and prognostic indicators of multiple sclerosis that are well known in the art. An individual at risk of developing multiple sclerosis as assessed by known prognostic indicators such as family history or symptom history also warrants administration of an IL-7R antagonist. One skilled in the art would recognize or know how to diagnose an individual with multiple sclerosis and, depending upon the degree or severity of the disease, can make the appropriate determination of when to administer the IL-7R antagonist and can also select the most desirable mode of administration.

An individual suffering from GVHD can be treated with an IL-7R antagonist such as, for example, an antagonist IL-7R antibody. An individual suitable for IL-7R antagonist therapy is selected using clinical criteria and prognostic indicators of GVHD that are well known in the art. Diagnosis or assessment of GVHD is well-established in the art. Tests for GVHD usually depend on the symptoms, but may include gastrointesting endoscopy, with or without a biopsy, liver functions tests (AST, ALP, and bilirubin levels will be increased), livery biopsy, lung x-rays, and/or skin biopsy. Features sufficient to establish the diagnosis of chronic GVHD include, for example without limitation, sclerosis, lichen-planus-like lesions, poikiloderma, esophageal webs, fasciitis and bronchiolitis obliterans (see, e.g., Leet and Flowers, Hematology, January 2008; 2008:134-141). Acute liver GVHD may be measured by, for example, the bilirubin level in acute patients. Acute skin GVHD may result in a diffuse maculopapular rash. Assessment of GVHD severity may be performed based on measures known in the art. In some embodiments, ameliorating, controlling, reducing incidence of, or delaying the development or progression of GVHD and/or symptoms of GVHD is measured by overall grade (skin-liver-gut) with each organ staged individually from a low of 1 to a high of 4. In some embodiments, ameliorating, controlling, reducing incidence of, or delaying the development or progression of GVHD and/or symptoms of GVHD is measured by monitoring body weight.

With respect to all methods described herein, reference to IL-7R antagonists also includes compositions comprising one or more additional agents. These compositions may further comprise suitable excipients, such as pharmaceutically acceptable excipients including buffers, which are well known in the art. The present invention can be used alone or in combination with other conventional methods of treatment.

The IL-7R antagonist can be administered to an individual via any suitable route. It should be apparent to a person skilled in the art that the examples described herein are not intended to be limiting but to be illustrative of the techniques available. Accordingly, in some embodiments, the IL-7R antagonist is administered to an individual in accord with known methods, such as intravenous administration, e.g., as a bolus or by continuous infusion over a period of time, by intramuscular, intraperitoneal, intracerebrospinal, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, an IL-7R antagonist can be aerosolized using a fluorocarbon formulation and a metered dose inhaler, or inhaled as a lyophilized and milled powder.

In one embodiment, an IL-7R antagonist is administered via site-specific or targeted local delivery techniques. Examples of site-specific or targeted local delivery techniques include various implantable depot sources of the IL-7R antagonist or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of an IL-7R antagonist may be used for administration. In some embodiments, the IL-7R antagonist may be administered neat. In some embodiments, IL-7R antagonist and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

An IL-7R antagonist can be administered using any suitable method, including by injection (e.g., intraperitoneally, intravenously, subcutaneously, intramuscularly, etc.). IL-7R antibodies can also be administered via inhalation, as described herein. Generally, for administration of IL-7R antibodies, an initial candidate dosage can be about 2 mg/kg. For the purpose of the present invention, a typical daily dosage might range from about any of 3 µg/kg to 30 µg/kg to 300 µg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to reduce blood glucose levels. An exemplary dosing regimen comprises administering an initial dose of about 2 mg/kg, followed by a weekly maintenance dose of about 1 mg/kg of the IL-7R antibody, or followed by a maintenance dose of about 1 mg/kg every other week. However, other dosage regimens may be useful, depending on the pattern of pharmacokinetic decay that the practitioner wishes to achieve. For example, in some embodiments, dosing from one to four times a week is contemplated. In other embodiments dosing once a month or once every other month or every three months is contemplated. The progress of this therapy is easily monitored by conventional techniques and assays. The dosing regimen (including the IL-7R antagonist(s) used) can vary over time.

For the purpose of the present invention, the appropriate dosage of an IL-7R antagonist will depend on the IL-7R antagonist (or compositions thereof) employed, the type and severity of symptoms to be treated, whether the agent is administered for preventive or therapeutic purposes, previous therapy, the patient's clinical history and response to the agent, the patient's clearance rate for the administered agent, and the discretion of the attending physician. Typically the clinician will administer an IL-7R antagonist until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., high blood glucose levels, joint pain, etc. Alternatively, sustained continuous release formulations of antagonist IL-7R antibodies may be appropriate. Various formulations and devices for achieving sustained release are known in the art.

In one embodiment, dosages for an IL-7R antagonist may be determined empirically in individuals who have been given one or more administration(s) of an IL-7R antagonist. Individuals are given incremental dosages of an IL-7R antagonist. To assess efficacy, an indicator of the disease can be followed.

Administration of an IL-7R antagonist in accordance with the method in the present invention can be continuous or intermittent, depending, for example, upon the recipient's physiological condition, whether the purpose of the administration is therapeutic or prophylactic, and other factors known to skilled practitioners. The administration of an IL-7R antagonist may be essentially continuous over a preselected period of time or may be in a series of spaced doses.

In some embodiments, more than one IL-7R antagonist may be present. At least one, at least two, at least three, at least four, at least five different, or more IL-7R antagonists can be present. Generally, those IL-7R antagonists may have complementary activities that do not adversely affect each other. For example, one or more of the following IL-7R antagonists may be used: an antagonist IL-7R antibody, an anti-sense molecule directed to an IL-7R (including an anti-sense molecule directed to a nucleic acid encoding IL-7R), an IL-7R inhibitory compound, and an IL-7R structural analog. An IL-7R antagonist can also be used in conjunction with other agents that serve to enhance and/or complement the effectiveness of the agents.

Therapeutic formulations of the IL-7R antagonist used in accordance with the present invention are prepared for storage by mixing an antibody having the desired degree of purity with optional pharmaceutically acceptable carriers, excipients or stabilizers (Remington, The Science and Practice of Pharmacy 20th Ed. Mack Publishing, 2000), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the IL-7R antagonist are prepared by methods known in the art, such as described in Epstein, et al., Proc. Natl. Acad. Sci. USA 82:3688, 1985; Hwang, et al., Proc. Natl. Acad. Sci. USA 77:4030, 1980; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing, 2000.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The formulations to be used for in vivo administration must be sterile. This is readily accomplished by, for example, filtration through sterile filtration membranes. Therapeutic IL-7R antagonist compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Infralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing an IL-7R antagonist with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

IL-7R Antagonists

The methods of the invention use an IL-7R antagonist, which refers to any protein, peptide or nucleic acid molecule that blocks, suppresses or reduces (including significantly reduces) IL-7R biological activity, including downstream pathways mediated by IL-7R signaling, such as elicitation of a cellular response to IL-7R. Examples of IL-7R antagonists include, without limitation, antagonist IL-7R antibodies, IL-7R siRNA, IL-7R shRNA, and IL-7R antisense oligonucleotides.

An IL-7R antagonist should exhibit any one or more of the following characteristics: (a) bind to IL-7R; (b) block IL-7R interaction with IL-7; (c) block or decrease IL-7-mediated STAT5 phosphorylation; (d) decrease blood glucose levels in vivo; (e) increase glucose tolerance in vivo; (f) reduce disease severity in experimental autoimmune encephalomyelitis (EAE); (g) block or decrease PI3K phosphorylation; (h) block or decrease AKT phosphorylation; and (i) block IL-7R interaction with other yet to be identified factors.

In some embodiments, the IL-7R antagonist is an antagonist IL-7R antibody. For purposes of this invention, the antagonist IL-7R antibody preferably reacts with IL-7Rα in a manner that inhibits IL-7R signaling function and IL-7 interaction. In some embodiments, the antagonist IL-7R antibody specifically recognizes primate IL-7R. In some embodiments, the antagonist IL-7R antibody binds primate and rodent IL-7R.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the antagonist IL-7R antibody is a monoclonal antibody. The antagonist IL-7R antibody can also be humanized. In other embodiments, the antibody is human.

In some embodiments, the antibody comprises a modified constant region, such as, for example without limitation, a constant region that has increased potential for provoking an immune response. For example, the constant region may be modified to have increased affinity to an Fc gamma receptor such as, e.g., FcγRI or FcγRIIA.

In some embodiments, the antibody comprises a modified constant region, such as a constant region that is immunologically inert, that is, having a reduced potential for provoking an immune response. In some embodiments, the constant region is modified as described in Eur. J. Immunol., 1999, 29:2613-2624; PCT Application No. PCT/GB99/01441; and/or UK Patent Application No. 9809951.8. The Fc can be human IgG1, human IgG2 or human IgG4. The Fc can be human IgG2 containing the mutation A330P331 to S330S331 (IgG2Δa), in which the amino acid residues are numbered with reference to the wild type IgG2 sequence. Eur. J. Immunol., 1999, 29:2613-2624. In some embodiments, the antibody comprises a constant region of $IgG_4$ comprising the following mutations (Armour et al., 2003, Molecular Immunology 40 585-593): E233F234L235 to P233V234A235 (IgG4Δc), in which the numbering is with reference to wild type IgG4. In yet another embodiment, the Fc is human IgG4 E233F234L235 to P233V234A235 with deletion G236 (IgG4Δb). In another embodiment the Fc is any human IgG4 Fc (IgG4, IgG4Δb or IgG4Δc) containing hinge stabilizing mutation S228 to P228 (Aalberse et al., 2002, Immunology 105, 9-19). In another embodiment, the Fc can be aglycosylated Fc.

In some embodiments, the constant region is aglycosylated by mutating the oligosaccharide attachment residue (such as Asn297) and/or flanking residues that are part of the glycosylation recognition sequence in the constant region. In some embodiments, the constant region is aglycosylated for N-linked glycosylation enzymatically. The constant region may be aglycosylated for N-linked glycosylation enzymatically or by expression in a glycosylation deficient host cell.

The binding affinity ($K_D$) of an antagonist IL-7R antibody to IL-7R (such as human IL-7R) can be about 0.002 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, about 50 pM, about 20 pM, about 10 pM, about 5 pM, or about 2 pM.

One way of determining binding affinity of antibodies to IL-7R is by measuring binding affinity of monofunctional Fab fragments of the antibody. To obtain monofunctional Fab fragments, an antibody (for example, IgG) can be cleaved with papain or expressed recombinantly. The affinity of an IL-7R Fab fragment of an antibody can be determined by surface plasmon resonance (Biacore™3000™ surface plasmon resonance (SPR) system, Biacore™, INC, Piscataway N.J.) equipped with pre-immobilized streptavidin sensor chips (SA) using HBS-EP running buffer (0.01M HEPES, pH 7.4, 0.15 NaCl, 3 mM EDTA, 0.005% v/v Surfactant P20). Biotinylated human IL-7R (or any other IL-7R) can be diluted into HBS-EP buffer to a concentration of less than 0.5 µg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound Fab while keeping the activity of IL-7R on the chip for over 200 injections. Typically, serial dilutions (spanning concentrations of 0.1-10× estimated $K_D$) of purified Fab samples are injected for 1 min at 100 µL/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any IL-7R, including human IL-7R, IL-7R of another mammal (such as mouse IL-7R, rat IL-7R, primate IL-7R), as well as different forms of IL-7R. Binding affinity of an antibody is generally measured at 25° C., but can also be measured at 37° C.

The antagonist IL-7R antibodies may be made by any method known in the art, including the method as provided in Example 1. For the production of hybridoma cell lines, the route and schedule of immunization of the host animal are generally in keeping with established and conventional techniques for antibody stimulation and production, as further described herein. General techniques for production of human and mouse antibodies are known in the art and/or are described herein.

It is contemplated that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., 1975, Nature 256:495-497 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the IL-7R monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for IL-7R, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a human IL-7Rα, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the antagonist IL-7R antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112; U.S. Pat. No. 7,314,622.

In an alternative, the polynucleotide sequence may be used for genetic manipulation to "humanize" the antibody or to improve the affinity, or other characteristics of the antibody. For example, the constant region may be engineered to more nearly resemble human constant regions to avoid immune response if the antibody is used in clinical trials and treatments in humans. It may be desirable to genetically manipulate the antibody sequence to obtain greater affinity to IL-7R and greater efficacy in inhibiting IL-7R. It will be apparent to one of skill in the art that one or more polynucleotide changes can be made to the antagonist IL-7R antibody and still maintain its binding ability to IL-7R.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated CDRs fused to human constant regions. See, for example, Winter et al. Nature 349:293-299, 1991, Lobuglio et al. Proc. Nat. Acad. Sci. USA 86:4220-4224, 1989, Shaw et al. J. Immunol. 138:4534-4538, 1987, and Brown et al. Cancer Res. 47:3577-3583, 1987. Other references describe rodent CDRs grafted into a human supporting framework region (FR) prior to fusion with an appropriate human antibody constant region. See, for example, Riechmann et al. Nature 332:323-327, 1988, Verhoeyen et al. Science 239: 1534-1536, 1988, and Jones et al. Nature 321:522-525, 1986. Another reference describes rodent CDRs supported by recombinantly engineered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., Nucl. Acids Res. 19:2471-2476, 1991, and in U.S. Pat. Nos. 6,180, 377; 6,054,297; 5,997,867; 5,866,692; 6,210,671; and 6,350, 861; and in PCT Publication No. WO 01/27160.

It is apparent that although the above discussion pertains to humanized antibodies, the general principles discussed are applicable to customizing antibodies for use, for example, in dogs, cats, primate, equines and bovines. It is further apparent that one or more aspects of humanizing an antibody described herein may be combined, e.g., CDR grafting, framework mutation and CDR mutation.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565, 332; 5,580,717; 5,733,743; and 6,265,150; and Winter et al., Annu. Rev. Immunol. 12:433-455, 1994. Alternatively, the phage display technology (McCafferty et al., Nature 348: 552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S, and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for IL-7R.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant regions in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of an IL-7R monoclonal antibody herein.

Antagonist IL-7R antibodies can be identified or characterized using methods known in the art, whereby reduction, amelioration, or neutralization of IL-7R biological activity is detected and/or measured. In some embodiments, an antagonist IL-7R antibody is identified by incubating a candidate agent with IL-7R and monitoring binding and/or attendant reduction or neutralization of a biological activity of IL-7R. The binding assay may be performed with purified IL-7R polypeptide(s), or with cells naturally expressing, or transfected to express, IL-7R polypeptide(s). In one embodiment, the binding assay is a competitive binding assay, where the ability of a candidate antibody to compete with a known IL-7R antagonist for IL-7R binding is evaluated. The assay may be performed in various formats, including the ELISA format. In other embodiments, an antagonist IL-7R antibody is identified by incubating a candidate agent with IL-7R and monitoring binding and attendant inhibition of STATS phorphorylation.

Following initial identification, the activity of a candidate antagonist IL-7R antibody can be further confirmed and refined by bioassays, known to test the targeted biological activities. Alternatively, bioassays can be used to screen candidates directly. Some of the methods for identifying and characterizing antagonist IL-7R antibodies are described in detail in the Examples.

Antagonist IL-7R antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antagonist IL-7R antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an antagonist IL-7R antibody. In another example, the epitope to which the antagonist IL-7R antibody binds can be determined in a systematic screening by using overlapping peptides derived from the IL-7R sequence and determining binding by the antagonist IL-7R antibody. According to the gene fragment expression assays, the open reading frame encoding IL-7R is fragmented either randomly or by specific genetic constructions and the reactivity of the expressed fragments of IL-7R with the antibody to be tested is determined. The gene fragments may, for example, be produced by PCR and then transcribed and translated into protein in vitro, in the presence of radioactive amino acids. The binding of the antibody to the radioactively labeled IL-7R fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant IL-7R in which various fragments of the IL-7R polypeptide have been replaced (swapped) with sequences from IL-7R from another species, or a closely related, but antigenically distinct protein (such as another member of the proprotein convertase family). By assessing binding of the antibody to the mutant IL-7R, the importance of the particular IL-7R fragment to antibody binding can be assessed.

Yet another method which can be used to characterize an antagonist IL-7R antibody is to use competition assays with other antibodies known to bind to the same antigen, i.e., various fragments on IL-7R, to determine if the antagonist IL-7R antibody binds to the same epitope as other antibodies. Competition assays are well known to those of skill in the art.

An expression vector can be used to direct expression of an antagonist IL-7R antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266: 338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell. Biol., 1994, 14:2411, and in Woffendin, Proc. Natl. Acad. Sci., 1994, 91:1581.

In some embodiments, the invention encompasses compositions, including pharmaceutical compositions, comprising antibodies described herein or made by the methods and having the characteristics described herein. As used herein, compositions comprise one or more antibodies that antagonize the interaction of IL-7R with IL-7, and/or one or more polynucleotides comprising sequences encoding one or more these antibodies. These compositions may further comprise suitable excipients, such as pharmaceutically acceptable excipients including buffers, which are well known in the art.

The antagonist IL-7R antibodies of the invention are characterized by any (one or more) of the following characteristics: (a) bind to IL-7R; (b) block IL-7R interaction with IL-7; (c) block or decrease IL-7-mediated STAT5 phosphorylation; (d) decrease blood glucose levels in vivo; (e) improve glucose tolerance in vivo; and (f) reduce disease severity in EAE. Preferably, antagonist IL-7R antibodies have two or more of these features. More preferably, the antibodies have three or more of the features. More preferably, the antibodies have four or more of the features. More preferably, the antibodies have five or more of the features. Most preferably, the antibodies have all six characteristics.

Accordingly, the invention provides any of the following, or compositions (including pharmaceutical compositions) comprising any of the following: (a) an antibody having a partial light chain sequence of NFMLTQPHSVSGSPGK-TVTISCTRSSGSIDSSYVQWYQQRPG NSPTTVIYED-DQRPSG VPDRFSGSIDSSSNSASLTISGLVT-EDEADYYCQSYDSSHLVFGGGTKLTVLC (SEQ ID NO: 1), NFMLTQPHSVSESPGKTVTISCTGSS-GRIASSYVQWYQQRPGSAPTTVIYEDNQRPSG VPDRFSGSIDSSSNSASLTISGLKT-EDEADYYCQSYASSSLWVFGGGTQLTVLS (SEQ ID NO: 3), NFMLTQPHSVSGSPGKTVTISCTRSSG-SIDSSYVQWYQQRPGNSPTTVIYEDDQRPSG VPDRF-SGSIDSSSNSASLTISGLVTEDEADYYC-MQYDSSHLVFGGGTKLTVLC (SEQ ID NO: 5), NFMLTQPHSVSGSPGKTVTISCTRSSG-SIDSSYVQWYQQRPG NSPTTVIYEDDQRPSG VPDRF-SGSIDSSSNSASLTISGLVTEDEADYYC-QSYDFHHLVFGGGTKLTVLC (SEQ ID NO: 7), NFMLTQPHSVSGSPGKTVTISCTRSSG-SIDSSYVQWYQQRPG NSPTTVIYEDDQRPSG VPDRF-SGSIDSSSNSASLTISGLVTEDEADYYC-QSYDFHHLVFGGGTKLTVLC (SEQ ID NO: 9), NFMLTQPHSVSGSPGKTVTISCTRSSG-
SIDSSYVQWYQQRPG NSPTTVIYEDDQRPSG VPDRF-
SGSIDSSSNSASLTISGLVTEDEADYYC-
MQYDFHHLVFGGGTKLTVLC (SEQ ID NO: 11),
NFMLTQPHSVSESPGKTVTISCTRSSG-
SIDSSYVQWYQQRPGSSPTTVIYEDDQRPSG VPDRF-
SGSIDSSSNSASLTISGLKTEDEADYYC-
MQYDFHHLVFGGGTKLTVL (SEQ ID NO: 44), or
NFMLTQPHSVSESPGKTVTISCTRSSG-
SIDSSYVQWYQQRPGSSPTTVIYEDDQRPSG VPDRF-
SGSIDSSSNSASLTISGLKTEDEADYYC-
QSYDFHHLVFGGGTKLTVL (SEQ ID NO: 41); and (b) an antibody having a partial heavy chain sequence of QVNL-RESGGGLVKPGGSLRLSCAASGFTFDDS-
VMHWVRQAPGKGLEWLSLVGWDG SATYYADS-
VKGRFTISRDNTKNLLYLQMNSLRAEDTAVYYCAR-
QGDYVFDYWGQGTL VTVSS (SEQ ID NO: 2),
QVTLKESGGGLVQPGGSLRLSCAASG-
FTFSNYGMHWVRQAPGKGLEWVSAISGSGG STYY-
ADSVKGRFTISRDNSKNTVYLQMNSLRD-
EDTAVYYCARDISGGGMDVWGQGTT VTVSS (SEQ ID NO: 4), QVNLRESGGGLVKPGGSLRLSCAASGFT-
FDDSVMHWVRQAPGKGLEWLSLVGWDG FFTYY-
ADSVKGRFTISRDNTKNLLYLQMNSL-
RAEDTAVYYCARQGDYVFNNWGQGTL VTVSS (SEQ ID NO: 6), QVNLRESGGGLVKPGGSLRLSCAASGFT-
FDDSVMHWVRQAPGKGLEWLSLVGWDG FFTYY-
ADSVKGRFTISRDNTKNLLYLQMNSL-
RAEDTAVYYCARQGDYMGDYWGQGTL VTVSS (SEQ ID NO: 8), QVNLRESGGGLVKPGGSLRLSCAASGFT-
FDDSVMHWVRQAPGKGLEWLSLVGWDG FFTYY-
ADSVKGRFTISRDNTKNLLYLQMNSL-
RAEDTAVYYCARQGDYMGNNWGQGTL VTVSS (SEQ ID NO: 10), QVNLRESGGGLVKPGGSLRLSCAASGFT-
FDDSVMHWVRQAPGKGLEWLSLVGWDG FFTYY-
ADSVKGRFTISRDNTKNLLYLQMNSL-
RAEDTAVYYCARQGDYMGNNWGQGTL VTVSS (SEQ ID NO: 12), or EVQLVESGGGLVKPGGSLRLSCAASG-
FTFDDSVMHWVRQAPGKGLEWVSLVGWDG FFTYY-
ADSVKGRFTISRDNAKNSLYLQMNSL-
RAEDTAVYYCARQGDYMGNNWGQGTL VTVSS (SEQ ID NO: 40).

TABLE 1

| mAb | Light Chain | Heavy Chain |
| --- | --- | --- |
| P3A9 | NFMLTQPHSVSGSPGKTVTIS CTRSSGSIDSSYVQWYQQRPG NSPTTVIYEDDQRPSGVPDRF SGSIDSSSNSASLTISGLVTE DEADYYCQSYDSSHLVFGGGT KLTVLC (SEQ ID NO: 1) | QVNLRESGGGLVKPGGSLRL SCAASGFTFDDSVMHWVRQA PGKGLEWLSLVGWDGSATYY ADSVKGRFTISRDNTKNLLY LQMNSLRAEDTAVYYCARQG DYVFDYWGQGTLVTVSS (SEQ ID NO: 2) |
| P4B3 | NFMLTQPHSVSESPGKTVTIS CTGSSGRIASSYVQWYQQRPG SAPTTVIYEDNQRPSGVPDRF SGSIDSSSNSASLTISGLKTE DEADYYCQSYASSSLWVFGGG TQLTVLS (SEQ ID NO: 3) | QVTLKESGGGLVQPGGSLRL SCAASGFTFSNYGMHWVRQA PGKGLEWVSAISGSGGSTYY ADSVKGRFTISRDNSKNTVY LQMNSLRDEDTAVYYCARDI SGGGMDVWGQGTTVTVSS (SEQ ID NO: 4) |
| P2D2 | NFMLTQPHSVSGSPGKTVTIS CTRSSGSIDSSYVQWYQQRPG NSPTTVIYEDDQRPSGVPDRF SGSIDSSSNSASLTISGLVTE DEADYYCMQYDSSHLVFGGGT KLTVLC (SEQ ID NO: 5) | QVNLRESGGGLVKPGGSLRL SCAASGFTFDDSVMHWVRQA PGKGLEWLSLVGWDGFFTYY ADSVKGRFTISRDNTKNLLY LQMNSLRAEDTAVYYCARQG DYVFNNWGQGTLVTVSS (SEQ ID NO: 6) |
| P2E11 | NFMLTQPHSVSGSPGKTVTIS CTRSSGSIDSSYVQWYQQRPG NSPTTVIYEDDQRPSGVPDRF SGSIDSSSNSASLTISGLVTE DEADYYCQSYDFHHLVFGGGT KLTVLC (SEQ ID NO: 7) | QVNLRESGGGLVKPGGSLRL SCAASGFTFDDSVMHWVRQA PGKGLEWLSLVGWDGFFTYY ADSVKGRFTISRDNTKNLLY LQMNSLRAEDTAVYYCARQG DYMGDYWGQGTLVTVSS (SEQ ID NO: 8) |
| HAL 403a | NFMLTQPHSVSGSPGKTVTIS CTRSSGSIDSSYVQWYQQRPG NSPTTVIYEDDQRPSGVPDRF SGSIDSSSNSASLTISGLVTE DEADYYCQSYDFHHLVFGGGT KLTVLC (SEQ ID NO: 9) | QVNLRESGGGLVKPGGSLRL SCAASGFTFDDSVMHWVRQA PGKGLEWLSLVGWDGFFTYY ADSVKGRFTISRDNTKNLLY LQMNSLRAEDTAVYYCARQG DYMGNNWGQGTLVTVSS (SEQ ID NO: 10) |
| HAL 403b | NFMLTQPHSVSGSPGKTVTIS CTRSSGSIDSSYVQWYQQRPG NSPTTVIYEDDQRPSGVPDRF SGSIDSSSNSASLTISGLVTE DEADYYCMQYDFHHLVFGGGT KLTVLC (SEQ ID NO: 11) | QVNLRESGGGLVKPGGSLRL SCAASGFTFDDSVMHWVRQA PGKGLEWLSLVGWDGFFTYY ADSVKGRFTISRDNTKNLLY LQMNSLRAEDTAVYYCARQG DYMGNNWGQGTLVTVSS (SEQ ID NO: 12) |
| C1GM | NFMLTQPHSVSESPGKTVTIS CTRSSGSIDSSYVQWYQQRPG SSPTTVIYEDDQRPSGVPDRF SGSIDSSSNSASLTISGLKTE DEADYYCQSYDFHHLVFGGGT KLTVL (SEQ ID NO: 41) | EVQLVESGGGLVKPGGSLRL SCAASGFTFDDSVMHWVRQA PGKGLEWVSLVGWDGFFTYY ADSVKGRFTISRDNAKNSLY LQMNSLRAEDTAVYYCARQG DYMGNNWGQGTLVTVSS (SEQ ID NO: 40) |
| C2M3 | NFMLTQPHSVSESPGKTVTIS CTRSSGSIDSSYVQWYQQRPG SSPTTVIYEDDQRPSGVPDRF SGSIDSSSNSASLTISGLKTE DEADYYCMQYDFHHLVFGGGT KLTVL (SEQ ID NO: 44) | EVQLVESGGGLVKPGGSLRL SCAASGFTFDDSVMHWVRQA PGKGLEWVSLVGWDGFFTYY ADSVKGRFTISRDNAKNSLY LQMNSLRAEDTAVYYCARQG DYMGNNWGQGTLVTVSS (SEQ ID NO: 40) |

In Table 1, the underlined sequences are CDR sequences according to Kabat and in bold according to Chothia.

The invention also provides CDR portions of antibodies to IL-7R (including Chothia, Kabat CDRs, and CDR contact regions). Determination of CDR regions is well within the skill of the art. It is understood that in some embodiments, CDRs can be a combination of the Kabat and Chothia CDR (also termed "combined CRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof. Table 2 provides examples of CDR sequences provided herein.

TABLE 2

| | Heavy Chain | | |
| --- | --- | --- | --- |
| mAb | CDRH1 | CDRH2 | CDRH3 |
| P3A9 | DSVMH (SEQ ID NO: 19) | LVGWDGSATYYADSVKG (SEQ ID NO: 21) | QGDYVFDY (SEQ ID NO: 24) |

TABLE 2-continued

| mAb | | | |
|---|---|---|---|
| P4B3 | NYGMH (SEQ ID NO: 20) | AISGSGGSTYYADSVKG (SEQ ID NO: 22) | DISGGGMDV (SEQ ID NO: 25) |
| P2D2 | DSVMH (SEQ ID NO: 19) | LVGWDGFFTYYADSVKG (SEQ ID NO: 23) | QGDYVFNN (SEQ ID NO: 26) |
| P2E11 | DSVMH (SEQ ID NO: 19) | LVGWDGFFTYYADSVKG (SEQ ID NO: 23) | QGDYMGDY (SEQ ID NO: 27) |
| HAL 403a | DSVMH (SEQ ID NO: 19) | LVGWDGFFTYYADSVKG (SEQ ID NO: 23) | QGDYMGNN (SEQ ID NO: 28) |
| C1GM | DSVMH (SEQ ID NO: 19) (Kabat); GFTFDDS (SEQ ID NO: 46) (Chothia); GFTFDDSVMH (SEQ ID NO: 47) (extended) | LVGWDGFFTYYADSVKG (SEQ ID NO: 23) (Kabat); GWDGFF (SEQ ID NO: 48) (Chothia); | QGDYMGNN (SEQ ID NO: 49); |
| C2M3 | DSVMH (SEQ ID NO: 19) | LVGWDGFFTYYADSVKG (SEQ ID NO: 23) | QGDYMGNN (SEQ ID NO: 49) |
| HAL 403b | DSVMH (SEQ ID NO: 19) | LVGWDGFFTYYADSVKG (SEQ ID NO: 23) | QGDYMGNN (SEQ ID NO: 28) |
| Heavy Chain consensus | $X_1X_2$VMH, wherein $X_1$ is D or N; $X_2$ is S or Y (SEQ ID NO: 50) | $X_1X_2X_3X_4X_5GX_6X_7$TYYADSVKG, wherein $X_1$ is L or A; $X_2$ is V or I; $X_3$ is G or S; $X_4$ is G or I; $X_5$ is D or S; $X_6$ is F, G or S; $X_7$ is F, A or S (SEQ ID NO: 51) | $X_1X_2X_3X_4X_5X_6X_7X_8$, wherein $X_1$ is Q or D; $X_2$ is G or S; $X_3$ is D or S; $X_4$ is Y or G; $X_5$ is M, V or G; $X_6$ is G or F; $X_7$ is N, D or M; $X_8$ is N, Y or D (SEQ ID NO: 52) |

| Light Chain | | | |
|---|---|---|---|
| mAb | CDRL1 | CDRL2 | CDRL3 |
| P3A9 | TRSSGSIDSSYVQ (SEQ ID NO: 29) | EDDQRPS (SEQ ID NO: 31) | QSYDSSHLV (SEQ ID NO: 33) |
| P4B3 | TGSSGRIASSYVQ (SEQ ID NO: 30) | EDNQRPS (SEQ ID NO: 32) | QSYASSSLWV (SEQ ID NO: 34) |
| P2D2 | TRSSGSIDSSYVQ (SEQ ID NO: 29) | EDDQRPS (SEQ ID NO: 31) | MQYDSSHLV (SEQ ID NO: 35) |
| P2E11 | TRSSGSIDSSYVQ (SEQ ID NO: 29) | EDDQRPS (SEQ ID NO: 31) | QSYDFHHLV (SEQ ID NO: 36) |
| HAL 403a | TRSSGSIDSSYVQ (SEQ ID NO: 29) | EDDQRPS (SEQ ID NO: 31) | QSYDFHHLV (SEQ ID NO: 36) |
| C1GM | TRSSGSIDSSYVQ (SEQ ID NO: 29) | EDDQRPS (SEQ ID NO: 31) | QSYDFHHLV (SEQ ID NO: 36) |
| C2M3 | TRSSGSIDSSYVQ (SEQ ID NO: 29) | EDDQRPS (SEQ ID NO: 31) | MQYDFHHLV (SEQ ID NO: 37) |
| HAL 403b | TRSSGSIDSSYVQ (SEQ ID NO: 29) | EDDQRPS (SEQ ID NO: 31) | MQYDFHHLV (SEQ ID NO: 37) |
| Light Chain consensus | T$X_1$SSG$X_2$I$X_3$SSYVQ wherein $X_1$ is R or G; $X_2$ is S or R; $X_3$ is D or A (SEQ ID NO: 53) | ED$X_1$QRPS wherein $X_1$ is D or N (SEQ ID NO: 54) | $X_1X_2$Y$X_3X_4X_5X_6$L$X_7$ wherein $X_1$ is Q or M; $X_2$ is S or Q; $X_3$ is D or A; $X_4$ is F or S; $X_5$ is H or S; $X_6$ is H or S; $X_7$ is V or W (SEQ ID NO: 55) |

CDR contact regions are regions of an antibody that imbue specificity to the antibody for an antigen. In general, CDR contact regions include the residue positions in the CDRs and Vernier zones which are constrained in order to maintain proper loop structure for the antibody to bind a specific antigen. See, e.g., Makabe et al., 2007, "Thermodynamic Consequences of Mutations in Vernier Zone Residues of a Humanized Anti-human Epidermal Growth Factor Receptor Murine Antibody," Journal of Biological Chemistry, 283:1156-1166. Determination of CDR contact regions is well within the skill of the art. In some embodiments, an antagonist IL-7R antibody comprises one or more CDR contact regions comprising an amino acid sequence selected from the group consisting of FTFDDSVM (SEQ ID NO: 56), GWDGFF (SEQ ID NO: 57), ARX$_1$X$_2$X$_3$X$_4$ wherein X$_1$, X$_2$, X$_3$, and X$_4$ can be any amino acid, (SEQ ID NO: 58), SGSIDSSY (SEQ ID NO: 59), EDDQRPSGV (SEQ ID NO: 60), and FHHL (SEQ ID NO: 61).

For any given embodiment containing more than one CDR, the CDRs may be any of Kabat, Chothia, extended, AbM, and/or contact.

The binding affinity ($K_D$) of an antagonist IL-7R antibody to IL-7R can be about 0.002 to about 200 nM. In some embodiments, the binding affinity is any of about 200 nM, 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, or about 50 pM.

The invention also provides methods of making any of these antibodies. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In another alternative, the antibodies can be made recombinantly using procedures that are well known in the art. In one embodiment, a polynucleotide comprises a sequence encoding the heavy chain and/or the light chain variable regions of antibody P3A9, P4B3, P2D2, P2E11, HAL403a, HAL403b, C1GM, or C2M3. The sequence encoding the antibody of interest may be maintained in a vector in a host cell and the host cell can then be expanded and frozen for future use. Vectors (including expression vectors) and host cells are further described herein.

The invention also encompasses scFv of antibodies of this invention. Single chain variable region fragments are made by linking light and/or heavy chain variable regions by using a short linking peptide (Bird et al., 1988, Science 242:423-426). An example of a linking peptide is (GGGGS)$_3$ (SEQ ID NO: 13), which bridges approximately 3.5 nm between the carboxy terminus of one variable region and the amino terminus of the other variable region. Linkers of other sequences have been designed and used (Bird et al., 1988, supra). Linkers should be short, flexible polypeptides and preferably comprised of less than about 20 amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

Other forms of single chain antibodies, such as diabodies are also encompassed. Diabodies are bivalent, bispecific antibodies in which heavy chain variable (VH) and light chain variable (VL) domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad. Sci. USA 90:6444-6448; Poljak, R. J., et al., 1994, Structure 2:1121-1123).

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121: 210). Traditionally, the recombinant production of bispecific antibodies was based on the coexpression of two immunoglobulin heavy chain-light chain pairs, with the two heavy chains having different specificities (Millstein and Cuello, 1983, Nature 305, 537-539).

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Humanized antibodies can be made using any methods know in the art. For example, four general steps may be used to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

In the recombinant humanized antibodies, the Fcγ portion can be modified to avoid interaction with Fcγ receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, for example, U.S. Pat. Nos. 5,997,867 and 5,866,692.

The invention encompasses modifications to the antibodies and polypeptides of the invention variants shown in Table 1, including functionally equivalent antibodies which do not significantly affect their properties and variants which have enhanced or decreased activity and/or affinity. For example, the amino acid sequence may be mutated to obtain an antibody with the desired binding affinity to IL-7R. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 3 under the heading of "conservative substitutions." If such substitutions result in a change in biological activity, then more substantial changes, denominated "exemplary substitutions" in Table 3, or as further described below in reference to amino acid classes, may be introduced and the products screened.

TABLE 3

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)—N-acetylglucosaminyltransferase III (GnTIII), a glycosyltransferase catalyzing formation of bisecting GlcNAc, was reported to have improved ADCC activity (Umana et al., 1999, Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments of the invention, the antibody comprises a modified constant region, such as a constant region that has increased affinity to a human Fc gamma receptor, is immunologically inert or partially inert, e.g., does not trigger complement mediated lysis, does not stimulate antibody-dependent cell mediated cytotoxicity (ADCC), or does not activate microglia; or has reduced activities (compared to the unmodified antibody) in any one or more of the following: triggering complement mediated lysis, stimulating antibody-dependent cell mediated cytotoxicity (ADCC), or activating microglia. Different modifications of the constant region may be used to achieve optimal level and/or combination of effector functions. See, for example, Morgan et al., Immunology 86:319-324, 1995; Lund et al., J. Immunology 157:4963-9 157:4963-4969, 1996; Idusogie et al., J. Immunology 164: 4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 1999, 29:2613-2624; PCT Application No. PCT/GB99/01441; and/or UK Patent Application No. 9809951.8. In other embodiments, the antibody comprises a human heavy chain IgG2 constant region comprising the following mutations: A330P331 to S330S331 (amino acid numbering with reference to the wild type IgG2 sequence). Eur. J. Immunol., 1999, 29:2613-2624. In still other embodiments, the constant region is aglycosylated for N-linked glycosylation. In some embodiments, the constant region is aglycosylated for N-linked glycosylation by mutating the glycosylated amino acid residue or flanking residues that are part of the N-glycosylation recognition sequence in the constant region. For example, N-glycosylation site N297 may be mutated to A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using Biacore™ surface plasmon resonance analysis, which detects differences in binding affinity of about 2-fold or greater. Biacore™ is particularly useful when the starting antibody already binds with a relatively high affinity, for example a $K_D$ of about 10 nM or lower. Screening using Biacore™ surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., 1993, Gene 137(1):109-18.

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore™ surface plasmon resonance analysis, and selection using any method known in the art for selection, including phage display, yeast display, and ribosome display.

The invention also encompasses fusion proteins comprising one or more fragments or regions from the antibodies of this invention. In one embodiment, a fusion polypeptide is provided that comprises at least 10 contiguous amino acids of the variable light chain region shown in SEQ ID NOs: 1, 3, 5, 7, 9, 11, 41 or 44 and/or at least 10 amino acids of the variable heavy chain region shown in SEQ ID NOs: 2, 4, 6, 8, 10, 12 or 40. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises a light chain variable region and/or a heavy chain variable region, as shown in any of the sequence pairs selected from among SEQ ID NOs: 1 and 2, 3 and 4, 5 and 6, 7 and 8, 9 and 10, 11 and 12, 41 and 40, and 44 and 40. In another embodiment, the fusion polypeptide comprises one or more CDR(s). In still other embodiments, the fusion polypeptide comprises CDR H3 (VH CDR3) and/or CDR L3 (VL CDR3). For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6H is tag. Tags are well known in the art.

A fusion polypeptide can be created by methods known in the art, for example, synthetically or recombinantly. Typically, the fusion proteins of this invention are made by preparing an expressing a polynucleotide encoding them using recombinant methods described herein, although they may also be prepared by other means known in the art, including, for example, chemical synthesis.

This invention also provides compositions comprising antibodies conjugated (for example, linked) to an agent that facilitate coupling to a solid support (such as biotin or avidin). For simplicity, reference will be made generally to antibodies with the understanding that these methods apply to any of the IL-7R binding and/or antagonist embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

An antibody or polypeptide of this invention may be linked to a labeling agent such as a fluorescent molecule, a radioactive molecule or any others labels known in the art. Labels are known in the art which generally provide (either directly or indirectly) a signal.

The invention also provides compositions (including pharmaceutical compositions) and kits comprising, as this disclosure makes clear, any or all of the antibodies and/or polypeptides described herein.

The invention also provides isolated polynucleotides encoding the antibodies of the invention, and vectors and host cells comprising the polynucleotide.

Accordingly, the invention provides polynucleotides (or compositions, including pharmaceutical compositions), comprising polynucleotides encoding any of the following: the antibodies C1GM, C2M3, P3A9, P4B3, P2D2, P2E11, HAL403a and HAL403b, or any fragment or part thereof having the ability to antagonize IL-7R.

In another aspect, the invention provides polynucleotides encoding any of the antibodies (including antibody fragments) and polypeptides described herein, such as antibodies and polypeptides having impaired effector function. Polynucleotides can be made and expressed by procedures known in the art.

In another aspect, the invention provides compositions (such as a pharmaceutical compositions) comprising any of the polynucleotides of the invention. In some embodiments, the composition comprises an expression vector comprising a polynucleotide encoding the antibody as described herein. In other embodiment, the composition comprises an expression vector comprising a polynucleotide encoding any of the antibodies described herein. In still other embodiments, the composition comprises either or both of the polynucleotides shown in SEQ ID NO: 38 and SEQ ID NO: 39 below:

```
C1GM heavy chain variable region
                                          (SEQ ID NO: 38)
GAGGTCCAGTTAGTGGAGTCTGGGGGAGGCCTGGTCAAGCCGGGGG
GGTCCCTGAGACTCTCCTGTGCAGCCTCTGGATTCACCTTTGATGA
TTCTGTCATGCACTGGGTCCGTCAAGCTCCGGGGAAGGGTCTGGAG
TGGGTTTCTCTTGTTGGTTGGGATGGTTTTTTTACATACTATGCAG
ACTCAGTGAAGGGCCGATTCACCATCTCCAGAGACAACGCGAAGAA
```

```
-continued
CTCTCTGTATCTGCAAATGAACAGCCTGAGAGCCGAGGACACGGCT
GTGTATTACTGTGCGAGACAAGGGGATTACATGGGGAACAACTGGG
GCCAGGGAACCCTGGTCACCGTCTCCTCA C2GM light chain variable region
                                          (SEQ ID NO: 39)
AATTTTATGCTGACTCAGCCCCACTCTGTGTCGGAATCTCCGGGAA
AGACGGTGACCATCTCCTGCACCCGCAGCAGTGGCAGCATTGACAG
TTCCTATGTGCAGTGGTACCAGCAGCGCCCGGGCAGCTCCCCCACC
ACTGTGATCTATGAGGATGACCAAAGACCCTCTGGGGTCCCTGATC
GGTTCTCTGGCTCCATCGACAGCTCCTCCAACTCTGCCTCCCTCAC
CATCTCTGGACTGAAAACTGAGGACGAGGCTGACTACTACTGTCAG
TCTTATGATTTTCATCATCTGGTGTTCGGCGGAGGGACCAAGCTGA
CCGTCCTA.
```

In still other embodiments, the composition comprises either or both of the polynucleotides shown in SEQ ID NO: 14 and SEQ ID NO: 15 below:

```
HAL403a heavy chain variable region
                                          (SEQ ID NO: 14)
CAGGTCAACTTAAGGGAGTCTGGGGGAGGCCTGGTCAAGCCGGGGG
GGTCCCTGAGACTCTCCTGTGCAGCCTCTGGATTCACCTTTGATGA
TTCTGTCATGCACTGGGTCCGTCAAGCTCCGGGGAAGGGTCTGGAG
TGGCTCTCTCTTGTTGGTTGGGATGGTTTTTTTACATACTATGCAG
ACTCAGTGAAGGGCCGATTCACCATCTCCAGAGACAACACCAAGAA
CTTACTGTATCTGCAAATGAACAGCCTGAGAGCCGAGGACACGGCT
GTGTATTACTGTGCGAGACAAGGGGATTACATGGGGAACAACTGGG
GCCAGGGAACCCTGGTCACCGTCTCCTCA HAL403a light chain variable region
                                          (SEQ ID NO: 15)
AATTTTATGCTGACTCAGCCCCACTCTGTGTCGGGGTCTCCGGAA
AGACGGTGACCATCTCCTGCACCCGCAGCAGTGGCAGCATTGACAG
TTCCTATGTGCAGTGGTACCAGCAGCGCCCGGGCAATTCCCCCACC
ACTGTGATCTATGAGGATGACCAAAGACCCTCTGGGGTCCCTGATC
GGTTCTCTGGCTCCATCGACAGCTCCTCCAACTCTGCCTCCCTCAC
CATCTCTGGACTGGTGACTGAGGACGAGGCTGACTACTACTGTCAG
TCTTATGATTTTCATCATCTGGTGTTCGGCGGAGGGACCAAGCTGA
CCGTCCTATGT.
```

Expression vectors, and administration of polynucleotide compositions are further described herein.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector.

Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as E. coli or B. subtillis) and yeast (such as S. cerevisae, S. pombe; or K. lactis). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to IL-7R or an IL-7R domain is effected by an immunoassay or FACS. A cell overexpressing the antibody or protein of interest can be identified.

Compositions

The compositions used in the methods of the invention comprise an effective amount of an antagonist IL-7R antibody, an antagonist IL-7R antibody derived polypeptide, or other IL-7R antagonists described herein. Examples of such compositions, as well as how to formulate, are also described in an earlier section and below. In some embodiments, the composition comprises one or more IL-7R antagonist antibodies. In other embodiments, the antagonist IL-7R antibody recognizes human IL-7Rα. In other embodiments, the antagonist IL-7R antibody is a human antibody. In other embodiments, the antagonist IL-7R antibody is a humanized antibody. In some embodiments, the antagonist IL-7R antibody comprises a constant region that is capable of triggering a desired immune response, such as antibody-mediated lysis or ADCC. In other embodiments, the antagonist IL-7R antibody comprises a constant region that does not trigger an unwanted or undesirable immune response, such as antibody-mediated lysis or ADCC. In other embodiments, the antagonist IL-7R antibody comprises one or more CDR(s) of the antibody (such as one, two, three, four, five, or, in some embodiments, all six CDRs).

It is understood that the compositions can comprise more than one antagonist IL-7R antibody (e.g., a mixture of antagonist IL-7R antibodies that recognize different epitopes of IL-7R). Other exemplary compositions comprise more than one antagonist IL-7R antibody that recognize the same epitope(s), or different species of antagonist IL-7R antibodies that bind to different epitopes of IL-7R.

The composition used in the present invention can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The antagonist IL-7R antibody and compositions thereof can also be used in conjunction with other agents that serve to enhance and/or complement the effectiveness of the agents.

D. Kits

The invention also provides kits for use in the instant methods. Kits of the invention include one or more containers comprising an IL-7R antagonist (such as, for example, a human antibody) described herein and instructions for use in accordance with any of the methods of the invention described herein. Generally, these instructions comprise a description of administration of the IL-7R antagonist for the above described therapeutic treatments.

In some embodiments, the IL-7R antagonist is an antagonist IL-7R antibody. In some embodiments, the antibody is a human antibody. In some embodiments, the antibody is a humanized antibody. In some embodiments, the antibody is a monoclonal antibody. The instructions relating to the use of an antagonist IL-7R antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an antagonist IL-7R antibody. The container may further comprise a second pharmaceutically active agent.

Kits may optionally provide additional components such as buffers and interpretive information. Normally, the kit comprises a container and a label or package insert(s) on or associated with the container.

Mutations and Modifications

To express the IL-7R antibodies of the present invention, DNA fragments encoding VH and VL regions can first be obtained using any of the methods described above. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical.

The antibodies may also be modified, e.g. in the variable domains of the heavy and/or light chains, e.g., to alter a binding property of the antibody. For example, a mutation may be made in one or more of the CDR regions to increase or decrease the $K_D$ of the antibody for IL-7R, to increase or decrease $k_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant region to increase the half-life of an IL-7R antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

In a process known as "germlining", certain amino acids in the VH and VL sequences can be mutated to match those found naturally in germline VH and $V_L$ sequences. In particular, the amino acid sequences of the framework regions in the $V_H$ and VL sequences can be mutated to match the germline sequences to reduce the risk of immunogenicity when the antibody is administered. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., 1992, J. Mol. Biol. 227:776-798; and Cox et al., 1994, Eur. J. Immunol. 24:827-836.

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of an IL-7R antibody of the invention can be cleaved. In various embodiments of the invention, the heavy and light chains of the IL-7R antibodies may optionally include a signal sequence.

Once DNA fragments encoding the VH and VL segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG2 constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the $V_H$-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker, e.g., encoding the amino acid sequence (Gly$_4$-Ser)$_3$, (SEQ ID NO: 16) such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. The single chain antibody may be monovalent, if only a single VH and VL are used, bivalent, if two VH and VL are used, or polyvalent, if more than two VH and VL are used. Bispecific or polyvalent antibodies may be generated that bind specifically to IL-7R and to another molecule.

In another embodiment, a fusion antibody or immunoadhesin may be made that comprises all or a portion of an IL-7R antibody of the invention linked to another polypeptide. In another embodiment, only the variable domains of the IL-7R antibody are linked to the polypeptide. In another embodiment, the VH domain of an IL-7R antibody is linked to a first polypeptide, while the VL domain of an IL-7R antibody is linked to a second polypeptide that associates with the first polypeptide in a manner such that the VH and VL domains can interact with one another to form an antigen binding site. In another preferred embodiment, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In other embodiments, other modified antibodies may be prepared using IL-7R antibody encoding nucleic acid molecules. For instance, "Kappa bodies" (Ill et al., 1997, Protein Eng. 10:949-57), "Minibodies" (Martin et al., 1994, EMBO J. 13:5303-9), "Diabodies" (Holliger et al., 1993, Proc. Natl. Acad. Sci. USA 90:6444-6448), or "Janusins" (Traunecker et al., 1991, EMBO J. 10:3655-3659 and Traunecker et al., 1992, Int. J. Cancer (Suppl.) 7:51-52) may be prepared using standard molecular biological techniques following the teachings of the specification.

Bispecific antibodies or antigen-binding fragments can be produced by a variety of methods including fusion of hybridomas or linking of Fab' fragments. See, e.g., Songsivilai & Lachmann, 1990, Clin. Exp. Immunol. 79:315-321, Kostelny et al., 1992, J. Immunol. 148:1547-1553. In addition, bispecific antibodies may be formed as "diabodies" or "Janusins." In some embodiments, the bispecific antibody binds to two different epitopes of IL-7R. In some embodiments, the modified antibodies described above are prepared using one or more of the variable domains or CDR regions from a human IL-7R antibody provided herein.

Generation of Antigen-Specific Antibodies

Monoclonal antibodies raised against recombinant mouse IL-7Rα/CD127/Fc chimera (R&D Systems Cat. No. 747-MR), and human antibodies obtained by biopanning a human naïve antibody library with recombinant IL-7Rα were evaluated for their ability to bind mouse and human IL-7R. Antibodies were further screened for their ability to block IL-7-mediated STAT5 phosphorylation in human peripheral blood mononuclear cells (PBMCs) and/or monkey PBMCs. This manner of antibody preparation yielded antagonist antibodies that show blocking of IL-7-mediated STAT5 phosphorylation, as shown in Example 1.

Representative materials of the present invention were deposited in the American Type Culture Collection (ATCC) on Feb. 9, 2011. Vector C1GM-VH having ATCC Accession No. PTA-11679 is a polynucleotide encoding the C1GM heavy chain variable region, and vector C1GM-VL having ATCC Accession No. PTA-11678 is a polynucleotide encoding the C1GM light chain variable region. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 8860G 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1

Generating and Screening Antagonist IL-7R Antibodies

This example illustrates the generation and screening of antagonist IL-7R antibodies.

General Procedures for Immunization of Animals for Generating Monoclonal Antibodies:

A 2-month old female Sprague Dawley rat was immunized with 50 ug recombinant mouse IL-7Rα/CD127/Fc chimera, which includes mouse IL-7Rα (Glu21-Asp239), hCD33 signal peptide (Met 1-Ala 16), and human IgG (Pro100-Lys330) (R&D Systems Cat. No. 747-MR). The antigen was prepared for immunization by mixing 50 ug antigen in 100 ul PBS with 100 ul Sigma Adjuvant System (Cat. No. S6322). The antigen mixture was vortexed and injected into the hind footpads and peritoneum on days 0, 2, 5 and 7. On day 9, 50 ug of antigen without adjuvant was injected intravenously in a total volume of 150 ul in physiological saline. On day 13, the spleen cells were prepared as a single cell suspension and fused with P3×63Ag8.653 mouse myeloma cells following a standard fusion protocol using 40% PEG 1500 (Boeringer Mannheim Biochemicals #783641). The fused cells were resuspended in medium containing 18% FBS, 2 mM L-glutamine, pen/strep, hypoxanthine, aminopterin and thymidine (HAT) (Sigma H0262) and 10% hybridoma fusion and cloning supplement (HFCS) (Cat. No. 11 363 735 001, Sigma), then plated out in 54 96-well plates at 200 ul/well. At day 7 after fusion, 150 ul of the medium was aspirated from each well, and the wells were re-fed with 200 ul of fresh medium. At day 11-13, supernatant from each well was tested for antibody to IL-7R and human Fc using ELISA (described below).

ELISA Screening of Antibodies:

Supernatant media from growing hybridoma clones were screened separately for their ability to bind the recombinant mouse (rm) IL-7R. The assays were performed with 96-well plates coated overnight with 50 µl of a 1 µg/ml solution of the antigen. Fifty-five coated plates were washed 4 times with PBS with 0.05% Tween and then 50 ul PBS with 0.5% BSA was added to each well. 5 ul from each well of the hybridoma plates were added to the assay plates, and the plates were incubated at room temperature for 2 hrs to allow binding. Excess reagents were washed from the wells between each step with PBS containing 0.05% Tween-20. 50 ul horseradish peroxidase (HRP) conjugated goat-anti mouse, F(ab')2, Fc specific (Jackson #115-036-008) was added to bind to the mouse antibodies bound to the antigen. For detection, 50 ul ABTS, 2,2'-Azino-bis(3-ethyl benzothiazoline-6-sulfonic acid) diammonium salt was added as substrate. The plates were read after 30 mins at 405 nm using a Molecular Devices THERMOmax™ instrument. Hybridoma clones that secreted antibodies that were capable of binding to mouse IL-7R were selected for further analysis. These positive hybridoma supernatants were then collected from the hybridoma plates and tested in ELISA assays against human Fc, goat anti rat IgM, and recombinant human (rh) IL-7R. Purified antibodies were then prepared for the antibodies that bound to rm IL-7R and antibodies that bound to both rm IL-7R and rh IL-7R.

General Procedures for Generating Fully Human Monoclonal Antibodies Using Phage Display:

Anti-human IL-7Rα human antibodies were isolated from a phage display human naïve scFv antibody library (Glanville G. et al., 2009, Proc Natl Acad Sci USA, 106(48):20216-20221) by a series of four rounds of bio-panning against human IL-7Rα (R&D Systems®). For each round of panning, 1 ml IL-7Rα (10 ug/ml in PBS) was coated on an immunotube at 4° C. overnight. The IL-7Rα coated immunotube was washed three times with PBST. $10^{13}$ phage (1 ml) were added to the immunotube and incubated at room temperature for 1 hour to allow binding. After binding, the immunotube was washed eight times with PBST. Bound phage were eluted and used to infect freshly grown TG1 cells. After the fourth round of panning, the positive binders were screened against both human IL-7Rα and mouse IL-7R by ELISA. The antibodies binding to both human and mouse IL-7R were further studied for their affinities and blocking function, and antibodies were selected for affinity maturation.

In Vitro Functional Assay:

Hybridoma clones secreting human or mouse IL-7R binding antibodies were expanded and supernatants were harvested. Total IgGs were purified from approximately 10 ml of the supernatant using protein A beads, dialyzed into PBS buffer, and the final volume reduced to yield solutions with 0.7-1 mg/ml of antibodies. Purified antibodies were then used to test their ability to block IL-7-mediated STAT5 phosphorylation in human PBMCs. For PBMC preparation, whole blood cells were collected through Ficoll gradient. Cells were maintained at 37° C. in 5% $CO_2$ in conical tubes (to prevent monocyte/macrophage adherence) for 1-2 h before stimulation with IL-2.

For the functional screening, human PBMCs were preincubated for 5 minutes with test antibodies (10 µg/ml) prior to addition of IL-7. A non-reactive isotype-matched antibody was used as a negative control (isotype control). Cells were stimulated with human IL-7 (0.1 ng/ml, R&D Systems®) for 15 minutes. To stop the IL-7 stimulation, formaldehyde was added directly to the culture medium to a final concentration of 1.6%. Cells were fixed for 15 min at room temperature. Methanol was then added directly to a final concentration of 80%, and samples were stored at 4° C. for 30 minutes to 1 hour before being immunostained. Cells were stained with anti-phospho-STAT5 (p-STAT) antibodies (BD Pharmingen, Y694 clone 47) and anti-CD4 antibodies (BD Pharmingen, RPA-T4). Using flow cytometry (LSRII, BD™ Biosciences), CD4+ gated cells were analyzed for p-STAT5 staining. Isotype control was set as 100% of p-STAT.

Figure 1:
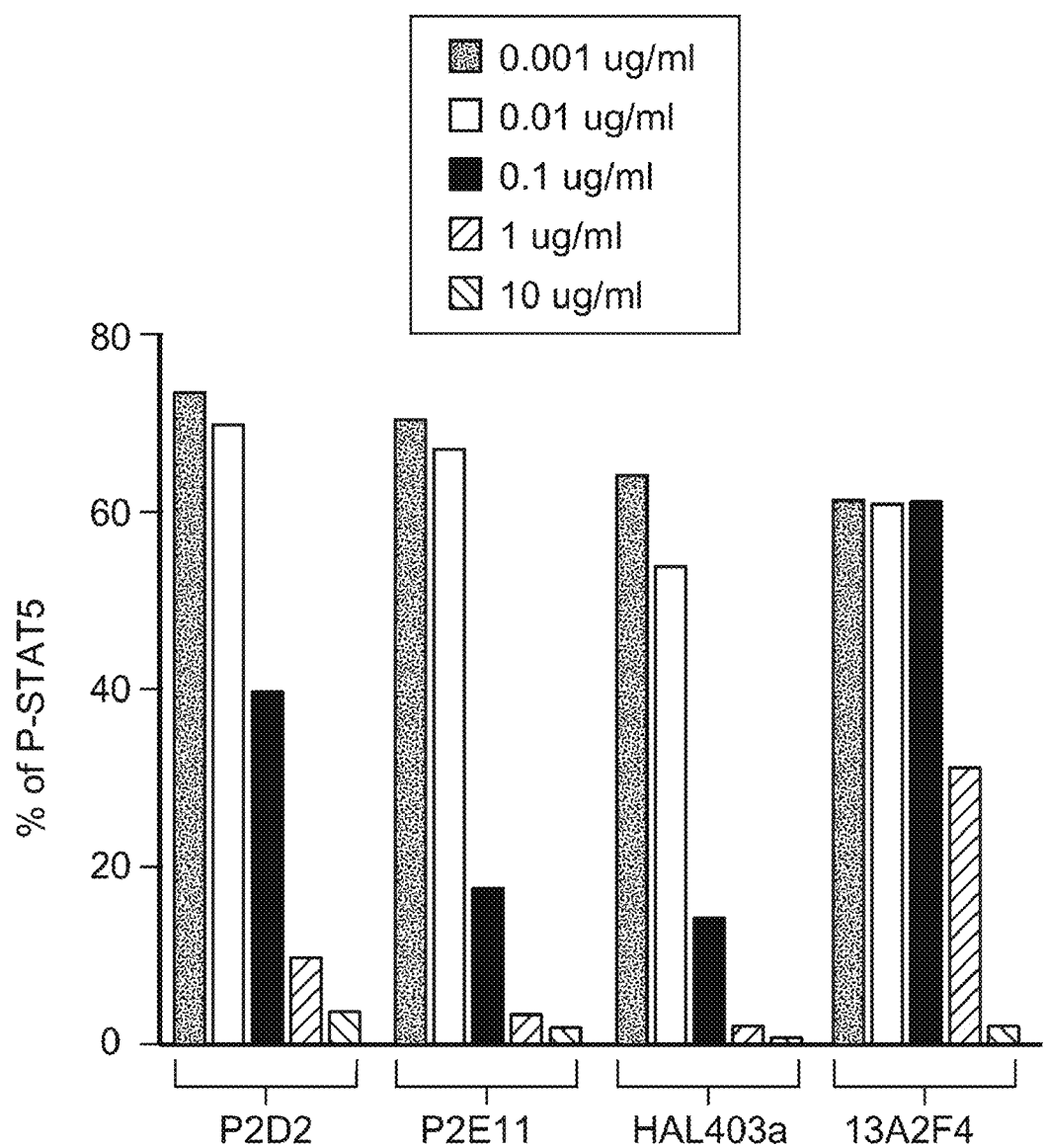
FIG. 1 depicts the dose-dependent effect of antagonist IL-7R monoclonal antibodies P2D2, P2E11 and HAL403a on IL-7-mediated STAT5 phosphorylation in human peripheral blood mononuclear cell (PBMCs). The x-axis indicates the percentage of CD4+ cells expressing phospho-STAT5 (p-STAT).

FIG. 1 illustrates the effect of antagonist IL-7R fully human monoclonal antibodies P2D2 and P2E11, and HAL403a on IL-7-mediated STAT5 phosphorylation in human PBMCs. A mouse anti-human IL-7R monoclonal antibody, 13A2F4, was used as a positive control, and a nonreactive isotype-matched antibody was used as a negative control (isotype control). Human PBMCs were preincubated for 5 minutes with each of the test antibodies or 13A2F4 at the following concentrations: 0.001, 0.01, 0.1, 1, and 10 µg/ml. The isotype control antibody was used at the highest concentration, 10 µg/ml. Cells were stimulated with human IL-7 (0.1 ng/ml) for 15 minutes, then fixed and immunostained as described above.

As measured by p-STAT5 staining, human antibodies P2D2, P2E11, HAL403a C1GM, C1GM-2 and C2M3 block human IL-7 mediated signaling in a dose-dependent manner (FIG. 1 and data not shown). The isotype control was set as 100% p-STAT5 staining. At 10 µg/ml antibody HAL403a blocked STAT5 phosphorylation very effectively (FIG. 1). C1GM, C1GM-2 and C2M3 blocked STAT5 phosphorylation comparable to HAL403a (data not shown).

The amino acid sequence of antagonist IL-7R antibody C1GM heavy chain (SEQ ID NO: 42) is shown below.

```
                                            (SEQ ID NO: 42)
EVQLVESGGGLVKPGGSLRLSCAASGFTFDDSVMHWVRQAPGKGLE

WVSLVGWDGFFTYYADSVKGRFTISRDNAKNSLYLQMNSLRAEDTA

VYYCARQGDYMGNNWGQGTLVTVSSASTKGPSVFPLAPSSKSTSGG

TAALGCLVKDYFPEPVTVSWNSGALTSGVHTFPAVLQSSGLYSLSS

VVTVPSSSLGTQTYICNVNHKPSNTKVDKKVAPELLGGPSVFLFPP

KPKDTLMISRTPEVTCVVVDVSHEDPEVKFNWYVDGVEVHNAKTKP

REEQYNSTYRVVSVLTVLHQDWLNGKEYKCKVSNKALPAPIEKTIS

KAKGQPREPQVYTLPPSREEMTKNQVSLTCLVKGFYPSDIAVEWES

NGQPENNYKTTPPVLDSDGSFFLYSKLTVDKSRWQQGNVFSCSVMH

EALHNHYTQKSLSLSPGK
```

The amino acid sequence of antagonist IL-7R antibody C1GM light chain (SEQ ID NO: 43) is shown below.

(SEQ ID NO: 43)
NFMLTQPHSVSESPGKTVTISCTRSSGSIDSSYVQWYQQRPGSSPT

TVIYEDDQRPSGVPDRFSGSIDSSSNSASLTISGLKTEDEADYYCQ

SYDFHHLVFGGGTKLTVLQPKAAPSVTLFPPSSEELQANKATLVCL

ISDFYPGAVTVAWKADSSPVKAGVETTTPSKQSNNKYAASSYLSLT

PEQWKSHRSYSCQVTHEGSTVEKTVAPTECS

The amino acid sequence of antagonist IL-7R antibody C1GM-2 heavy chain (SEQ ID NO: 45) is shown below.

(SEQ ID NO: 45)
EVQLVESGGGLVKPGGSLRLSCAASGFTFDDSVMHWVRQAPGKGLE

WVSLVGWDGFFTYYADSVKGRFTISRDNAKNSLYLQMNSLRAEDTA

VYYCARQGDYMGNNWGQGTLVTVSSASTKGPSVFPLAPCSRSTSES

TAALGCLVKDYFPEPVTVSWNSGALTSGVHTFPAVLQSSGLYSLSS

VVTVPSSNFGTQTYTCNVDHKPSNTKVDKTVAPPVAGPSVFLFPPK

PKDTLMISRTPEVTCVVVDVSHEDPEVQFNWYVDGVEVHNAKTKPR

EEQFNSTFRVVSVLTVVHQDWLNGKEYKCKVSNKGLPSSIEKTISK

TKGQPREPQVYTLPPSREEMTKNQVSLTCLVKGFYPSDIAVEWESN

GQPENNYKTTPPMLDSDGSFFLYSKLTVDKSRWQQGNVFSCSVMHE

ALHNHYTQKSLSLSPGK

The amino acid sequence of antagonist IL-7R antibody C1GM-2 light chain (SEQ ID NO: 43) is shown below.

(SEQ ID NO: 43)
NFMLTQPHSVSESPGKTVTISCTRSSGSIDSSYVQWYQQRPGSSPT

TVIYEDDQRPSGVPDRFSGSIDSSSNSASLTISGLKTEDEADYYCQ

SYDFHHLVFGGGTKLTVLQPKAAPSVTLFPPSSEELQANKATLVC

LISDFYPGAVTVAWKADSSPVKAGVETTTPSKQSNNKYAASSYLSL

TPEQWKSHRSYSCQVTHEGSTVEKTVAPTECS

The amino acid sequence of antagonist IL-7R antibody HAL403a heavy chain (SEQ ID NO: 17) is shown below.

(SEQ ID NO: 17)
QVNLRESGGGLVKPGGSLRLSCAASGFTFDDSVMHWVRQAPGKGL

EWLSLVGWDGFFTYYADSVKGRFTISRDNTKNLLYLQMNSLRAED

TAVYYCARQGDYMGNNWGQGTLVTVSSASTKGPSVFPLAPCSRST

SESTAALGCLVKDYFPEPVTVSWNSGALTSGVHTFPAVLQSSGLY

SLSSVVTVPSSNFGTQTYTCNVDHKPSNTKVDKTVAPPVAGPSVF

LFPPKPKDTLMISRTPEVTCVVVDVSHEDPEVQFNWYVDGVEVHN

AKTKPREEQFNSTFRVVSVLTVVHQDWLNGKEYKCKVSNKGLPSS

IEKTISKTKGQPREPQVYTLPPSREEMTKNQVSLTCLVKGFYPSD

IAVEWESNGQPENNYKTTPPMLDSDGSFFLYSKLTVDKSRWQQGN

VFSCSVMHEALHNHYTQKSLSLSPGK

The amino acid sequence of antagonist IL-7R antibody HAL403a light chain (SEQ ID NO: 18) is shown below.

(SEQ ID NO: 18)
NFMLTQPHSVSGSPGKTVTISCTRSSGSIDSSYVQWYQQRPGNSP

TTVIYEDDQRPSGVPDRFSGSIDSSSNSASLTISGLVTEDEADY

YCQSYDFHHLVFGGGTKLTVLTVAAPSVFIFPPSDEQLKSGTASV

VCLLNNFYPREAKVQWKVDNALQSGNSQESVTEQDSKDSTYSLSS

TLTLSKADYEKHKVYACEVTHQGLSSPVTKSFNRGEC

Example 2

Determining Antibody Binding Affinity

This example illustrates the determination of antibody binding affinity for antagonist IL-7R antibodies.

The affinities of antagonist IL-7R antibodies to human IL-7R were measured on a surface plasmon resonance Biacore™ 2000 or 3000 biosensor equipped with a research-grade CM5 sensor chip (Biacore™ AB, Uppsala, Sweden—now GE Healthcare). Goat polyclonal anti-human F(ab')2 fragments (Fc specific) were amine-coupled at saturating levels onto all four flow cells using a standard N-hydroxysuccinimide/ethyldimethylaminopropyl carbodiimide (NHS/EDC) chemistry in HBS-P running buffer (from Biacore™). The buffer was switched to HBS-P containing 1 mg/mL BSA. Human IL-7R-hFc antigen (R&D systems, Minneapolis, USA) was diluted to about 30 µg/mL and captured for 3 min at 5 µL/min to give levels of about 500-1000 RU per flow cell, leaving one blank to serve as a reference channel. Fab, hIgG1, or hIgG2ΔA formats of the antibodies were injected in duplicates as a 5-membered 3-fold series starting at 2 µM and a 5-membered 4-fold series starting at 0.4 µM for 3 min at 20-50 µL/min. Dissociation was monitored for 5 min. The capture chip was regenerated after the last injection of each titration with two 30 sec pulses of 75 mM phosphoric acid or 10 mM Glycine-HCl pH 1.7. Buffer cycles provided blanks for double-referencing the binding response data, which were then fit globally to a simple reversible binding model using Biaevaluation software v.4.1 to deduce the kinetic association and dissociation rate constants, respectively $k_a$ and $k_d$. Affinities were deduced from their ratio ($K_D=k_d/k_a$). The results in Table 4 show that these antibodies have picomolar or nanomolar affinities for human IL-7R.

TABLE 4

| mAb | $K_{on}$ for IL-7R (1/Ms) | $K_{off}$ for IL-7R (1/S) | $K_D$ for IL-7R (nM) |
|---|---|---|---|
| P3A9* | 5.60E+04 | 1.14E-02 | 204 |
| P4B3* | 1.56E+04 | 3.51E-03 | 225 |
| P2D2* | 7.17E+04 | 8.82E-04 | 12 |
| P2E11* | 1.55E+05 | 4.97E-04 | 3 |
| HAL403a* | 5.07E+06 | 2.86E-04 | 0.06 |
| HAL403b* | 1.39E+06 | 8.08E-05 | 0.06 |
| C1GM* | 4.85E+06 | 1.71E-04 | 0.04 |
| C1GM** | 1.42E+06 | 4.05E-04 | 0.286 |
| C1GM-2*** | 1.51E+06 | 4.07E-04 | 0.270 |
| C2M3** | 1.41E+06 | 3.07E-04 | 0.218 |
| C2M3*** | 1.55E+06 | 3.02E-04 | 0.195 |

*Fab;
**hIgG1;
***hIgG2ΔA

Example 4

Antagonist IL-7R Antibodies Reduce Disease Incidence in Non-Obese Diabetic (NOD) Animals, a Mouse Model for Type 1 Diabetes This example illustrates the effect of antagonist IL-7R antibodies in a mouse model for type 1 diabetes.

To study the in vivo effect of antagonist IL-7R antibodies on the diabetogenic process, a rat anti-mouse antagonist IL-7R antibody, 28G9 (Rinat), was tested in NOD mice. NOD mice exhibit a susceptibility to spontaneous development of autoimmune insulin dependent diabetes mellitus (IDDM, type 1 diabetes) (Kikutani et al., 1992, Adv. Immunol. 51: 285-322). 28G9 blocks IL-7-mediated STAT5 phosphorylation in mouse splenocytes and cross-competes with antagonist IL-7R human antibodies C1GM, C2M3, HAL403a, HAL403b, P3A9, P4B3, P2D2 and P2E11 in Biacore™.

6-8 week old NOD female mice (The Jackson Laboratory) were injected intraperitoneally (i.p.) weekly starting at 9 weeks old (t=0) with either 3 or 10 mg/kg body weight of 28G9. PBS or non-reactive isotype matched rat monoclonal antibody (isotype) were used as negative controls. The isotype antibody was administered at 10 mg/kg body weight. Mice were monitored two times per week for body weight and blood glucose. Diabetes was considered established when blood glucose level was at or over positive readings, i.e., over 250 mg/dL for two consecutive monitorings. The onset of diabetes was dated from the first of the sequential measurements.

Figure 2:
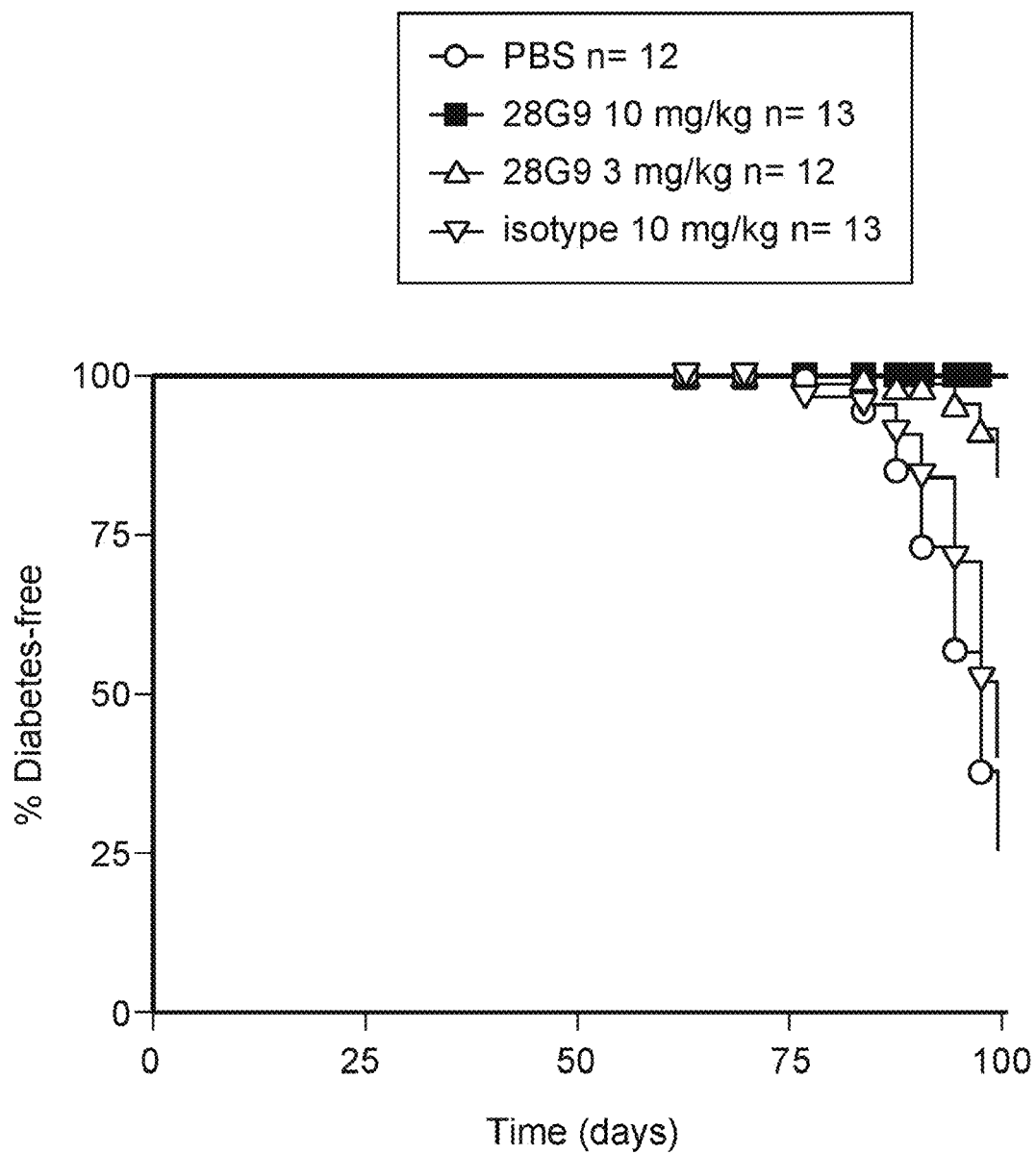
FIG. 2 depicts the effect of antagonist IL-7R monoclonal antibody 28G9 on development of diabetes in non-obese diabetic (NOD) mice.
Figure 3A:
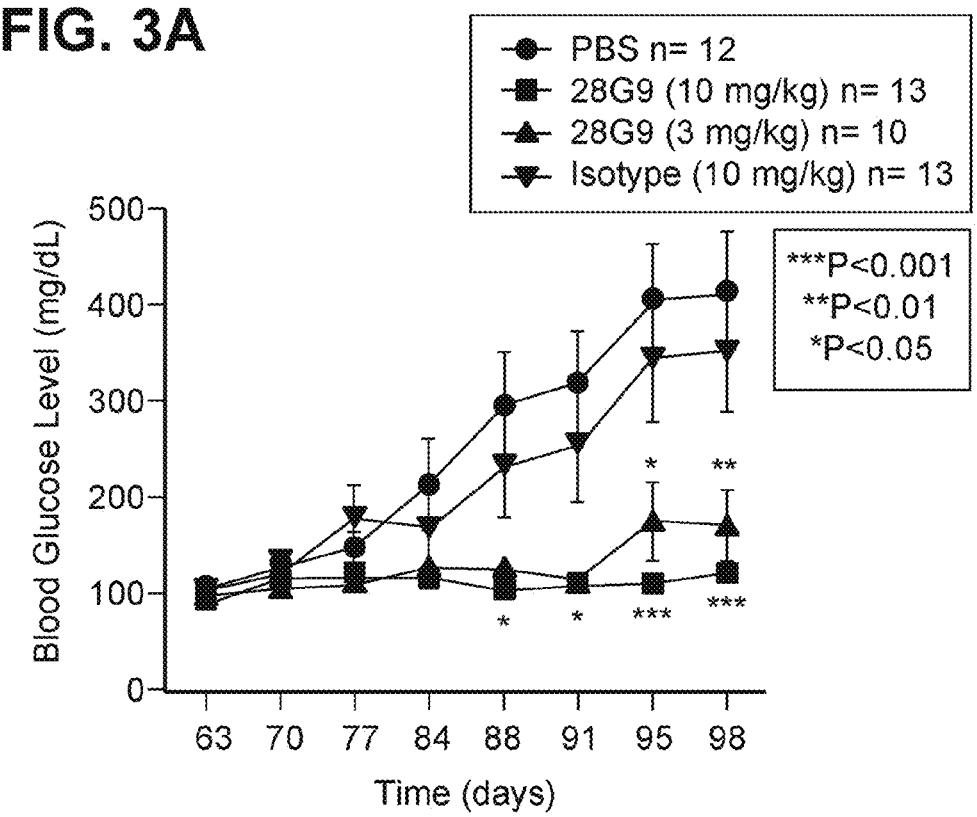
FIG. 3 depicts the effect of antagonist IL-7R monoclonal antibody 28G9 on (A) blood glucose levels (mg/dL) and (B) body weight (g) in NOD mice.
Figure 3B:
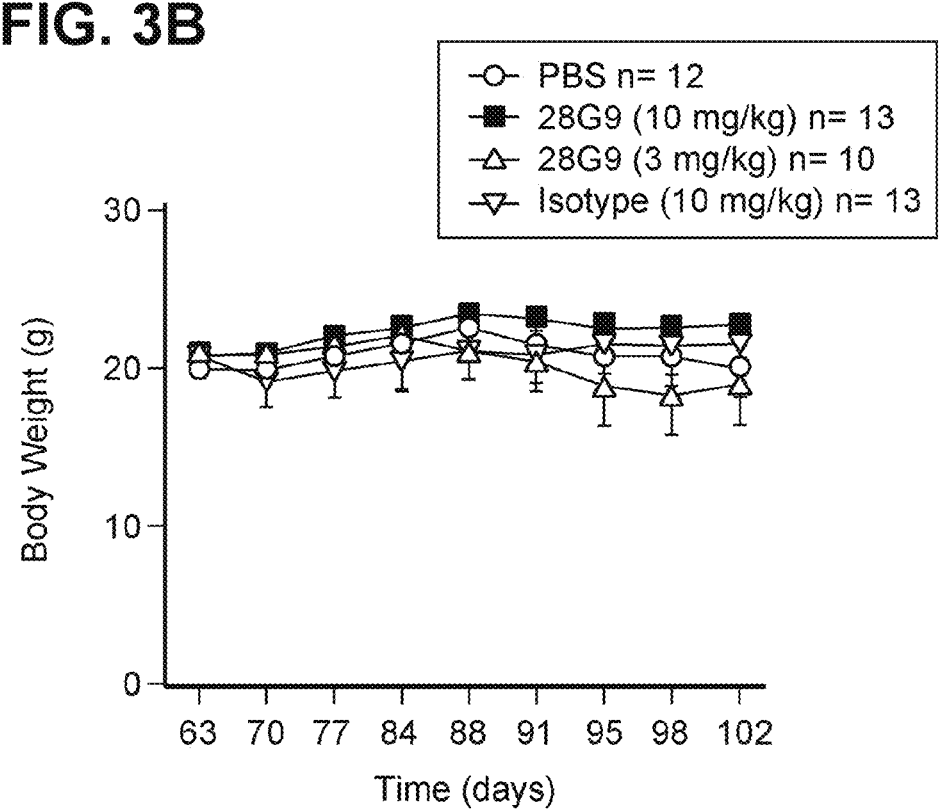

As shown in FIG. 2, none of the mice treated with 28G9 at 10 mg/kg developed diabetes even at 18 weeks of age. In contrast, 75-80% of the PBS and isotype-treated mice developed diabetes (FIG. 2). Although not all mice treated with 28G9 at 3 mg/kg were diabetes-free at the end of the study, a significantly reduced diabetes incidence compared to the PBS and isotype controls was observed, demonstrating the inhibitory effect of 28G9 on diabetes development was dose-dependent (FIG. 2). Treatment with 28G9 at 10 mg/kg significantly reduced blood glucose level compared to isotype or PBS controls (FIG. 3A). Mouse development during antagonist IL-7R antibody treatment was monitored by tracking body weight and mortality. As shown in FIG. 3B, multiple dosing of 3 or 10 mg/kg 28G9 had no significant effect on mouse growth, and no mortality was found at 10 mg/kg. Thus, antagonist IL-7R antibodies reduce blood glucose levels and inhibit diabetes progression in NOD animals. These results demonstrate that antagonist IL-7R antibodies are effective in preventing and slowing the progression of type 1 diabetes.

Figure 4A:
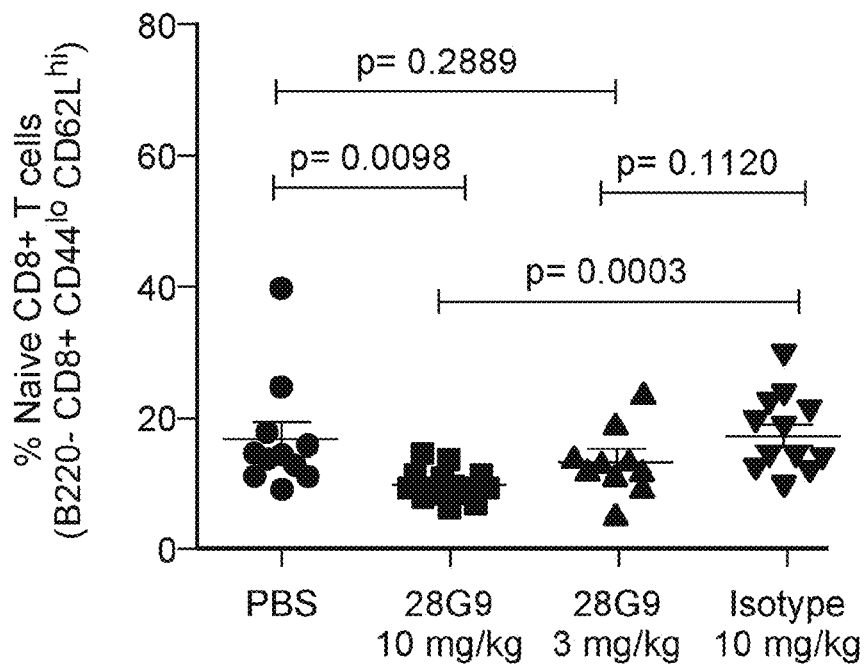
FIG. 4 depicts the effect of antagonist IL-7R monoclonal antibody 28G9 on (A) naïve CD8+ T cell and (B) memory CD8+ T cell populations in NOD mice. For the x-axis, the total CD8+ T cell population was set as 100%.
Figure 4B:
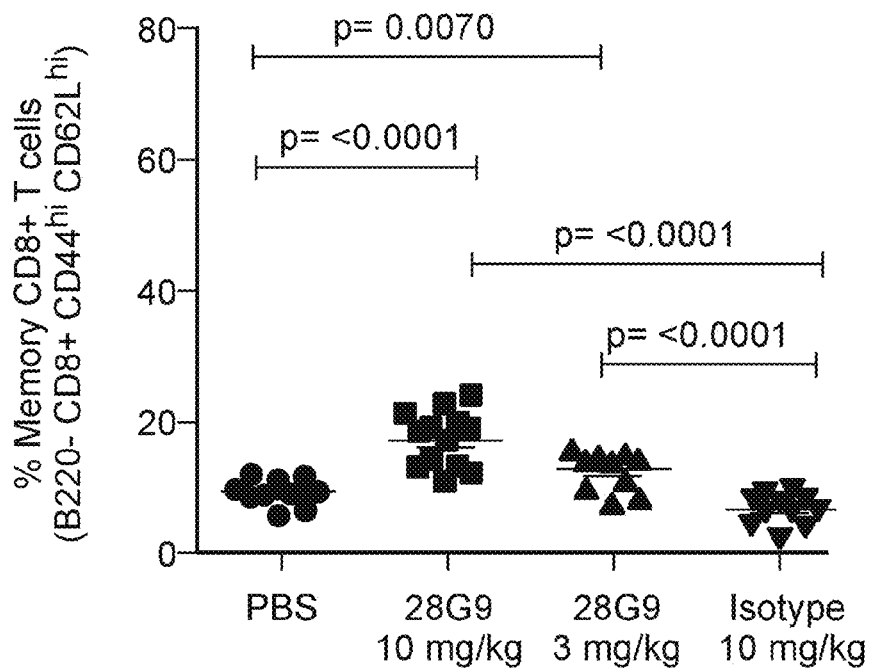

To investigate the effect of antagonist IL-7R antibodies on peripheral T cell regulation, CD4+ and CD8+ T cells were immunostained for the activation markers CD44 and CD62L and analyzed by flow cytometry. CD4+ and CD8+ T cells were isolated from the peripheral blood of PBS-treated, 28G9-treated, or isotype-treated mice. In comparison to the isotype control, the percentage of naive CD8+ T cells (B220-CD8+CD44$^{lo}$CD6212$^{hi}$) in mice treated with 28G9 at 10 mg/kg was significantly lower, and the percentage of memory CD8+ T cells (B220-CD8+CD44$^{hi}$CD62L$^{hi}$) were significantly higher (FIGS. 4A and 4B). In contrast, naïve CD4+ T cells (B220-CD4+CD44$^{lo}$CD6212$^{hi}$) were not significantly depleted in antagonist IL-7R antibody treated mice compared to isotype control (FIG. 5). These results indicate that antagonist IL-7R antibodies reduce blood glucose levels through naïve CD8+ T cell depletion.

Example 5

Antagonist IL-7R Antibodies Delay Onset of Autoimmune Disease

This example illustrates the effect of antagonist IL-7R antibodies in a mouse model for multiple sclerosis, experimental autoimmune encephalomyelitis (EAE).

The STAT5 activation assay was used to identify antagonist IL-7R antibodies. Spleens from B6 or BALB/c were homogenized in PBS and lysed in ACK lysis buffer (Invitrogen) for 2 min and then filtered through 100-μm pore size mesh, pelleted, and resuspended at 5×10$^6$ cells/ml in room temperature to 37° C. RPMI 1640 containing 10% FBS, penicillin (100 U/ml), streptomycin (100 μg/ml), and L-glutamine. Cells were maintained at 37° C. in 5% $CO_2$ in conical tubes (to prevent monocyte/macrophage adherence) for 1-2 h before stimulation. Cells were preincubated with test antibody for 5 minutes prior to stimulation with IL-7. Cells were treated for 15 min with murine IL-7 (mIL-7, 0.1 ng/ml). Formaldehyde was added directly to the culture medium to a final concentration of 1.6%, and cells were fixed for 15 min at room temperature. Methanol was then added directly to a final concentration of 80%, and samples were stored at 4° C. for 30 min to 1 h before immunostaining. The following antibodies were used for immunostaining: CD11b-FITC (M1/70), B220-Cy5.5PerCP, TCRβ-FITC, p-STAT5 (Y694, clone 47)-Alexa 647 (BD™ Pharmingen). TCRβ+ and CD11b+ cells were stained for phospho-STAT5. IL-7-stimulated STAT5 phosphorylation was observed by gating with TCRβ in flow cytometry. A number of antibodies that blocked STAT5 phosphorylation were identified, including monoclonal antibodies 28B6 and 28G9.

Active EAE was induced in 6- to 8-week-old female B6 mice by subcutaneous immunization with 100 pg of MOG$_{35-55}$ peptide (MEVGWYRSPFSRVVHLYRNGK (SEQ ID NO: 15)) emulsified in CFA containing 1 mg/ml of heat-killed *Mycobacterium tuberculosis* H37RA (Difco) on day 0 (see, Steinman and Zamvil, 2006). Additionally, mice received 400 ng of pertussis toxin (Calbiochem) i.v. in 0.1 ml of PBS on days 0 and 2. Starting on day 7 after MOG immunization, animals were treated twice weekly with antagonist IL-7R antibody 28B6 (10 mg/kg), antagonist IL-7R antibody 28G9 (10 mg/kg), or non-reactive isotype-matched antibody (10 mg/kg). Compared to isotype control, treatment with either 28G9 or 28B6 significantly reduced EAE activity as early as day 15 post immunization (FIG. 6). This result demonstrates that antagonist IL-7R antibodies are effective in slowing the progression of EAE.

Figure 7:
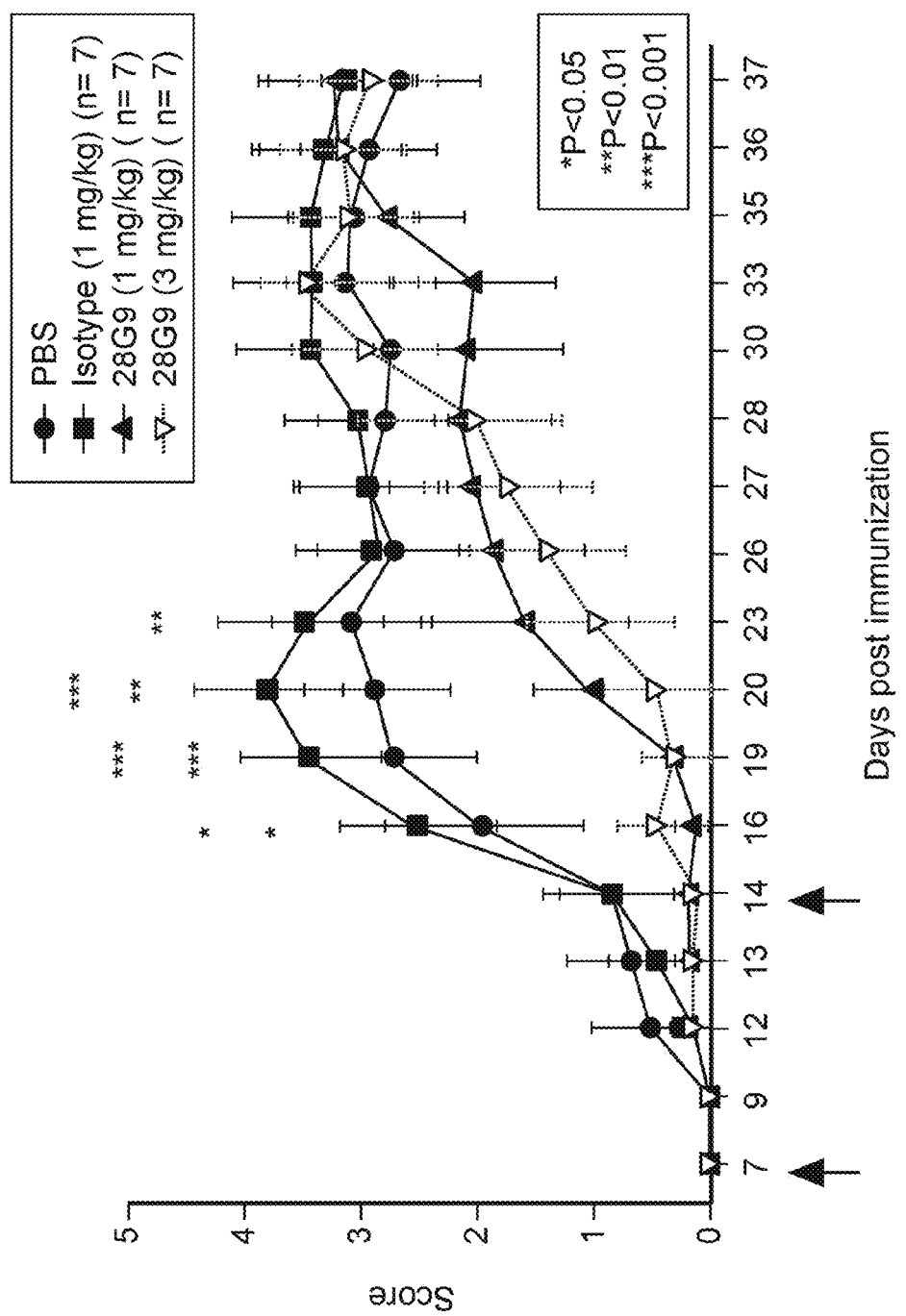
FIG. 7 depicts the dose-dependent effect of antagonist IL-7R monoclonal antibody 28G9 on clinical severity of EAE animals.
Figure 8:
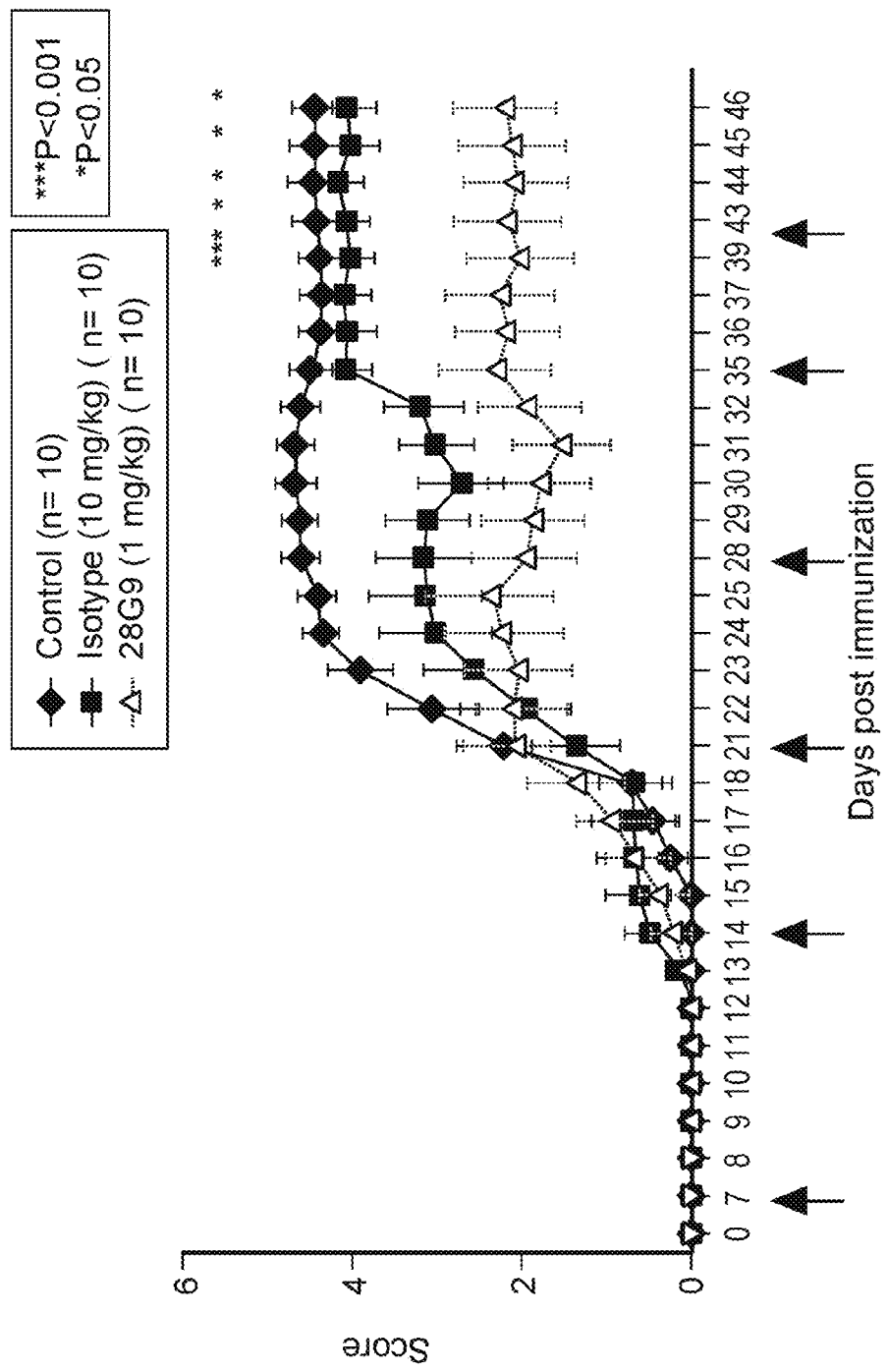
FIG. 8 depicts the effect of antagonist IL-7R monoclonal antibody 28G9 on clinical severity of EAE animals.

To test whether the antagonist IL-7R antibodies are efficacious in a dose-dependent manner, MOG immunized EAE animals were treated with either 1 or 3 mg/kg of 28G9 at day 7 and day 14 post immunization. A non-reactive isotype-matched antibody (1 mg/kg) was used as a negative control. In comparison to the isotype control, 28G9 treatment at both dosage levels reduced EAE severity at disease peak (FIG. 7). This inhibitory effect of the antagonist IL-7R antibody lasted for about a week. This result demonstrates that antagonist IL-7R antibodies conferred protection at both 1 and 3 mg/kg. In a separate study, MOG immunized EAE animals were treated weekly with 1, 3 or 10 mg/kg of 28G9 starting at day 7. Mice treated with 28G9 at 1 mg/kg showed significant efficacy with no mortality (FIG. 8). These results demonstrate that 1 mg/kg of antagonist IL-7R antibody treatment is effective in slowing the progression of EAE and is well-tolerated.

Figure 9:
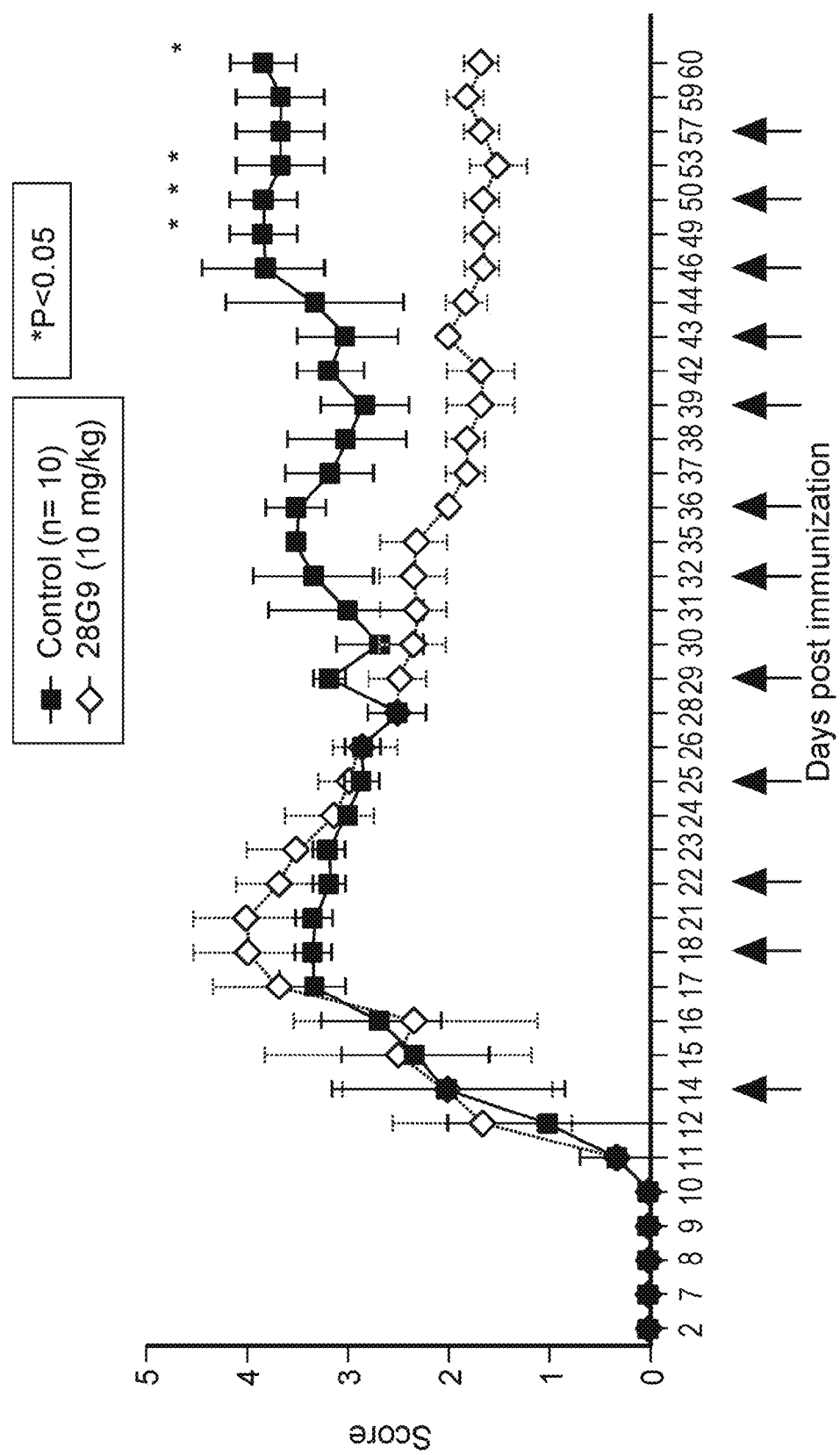
FIG. 9 depicts the effect of antagonist IL-7R monoclonal antibody 28G9 in animals with established EAE.

To investigate antagonist IL-7R antibody efficacy in established disease, MOG immunized EAE animals were treated twice weekly with 28G9 at 10 mg/kg starting day 14 after immunization. A non-reactive isotype-matched antibody (10 mg/kg) was used as a negative control. Compared to the control, treatment with antagonist IL-7R antibody significantly reduced EAE severity (FIG. 9). No mortality with the antagonist IL-7R antibody observed. This result demonstrates that antagonist IL-7R antibodies are effective to ameliorate established, ongoing EAE.

To further determine whether antagonist IL-7R antibodies can reduce EAE at late intervention at lower dose, MOG immunized EAE animals were treated once weekly with 28G9 at 3 mg/kg starting day 14 after immunization. A non-reactive isotype-matched antibody (3 mg/kg) was used as a negative control. Compared to the control, a highly significant reduction of disease severity was observed with antagonist IL-7R antibody treatment (FIG. 10). This result demonstrates that antagonist IL-7R antibody treatment is effective to reduce disease activity even at late intervention and lower dose.

Example 6

Immunological Changes After Antagonist IL-7R Antibody Therapy in Autoimmune Disease This example illustrates immunological changes in EAE mice after antagonist IL-7R antibody treatment.

To gain insight into the mechanisms by which antagonist IL-7R antibody acts to ameliorate EAE in the mouse model, lymphocyte populations from treated and control animals were analyzed by immunostaining and flow cytometry. For the immunological studies in this example, MOG immunized EAE animals were treated weekly with antagonist IL-7R antibody 28G9 (10 mg/kg), 28B6 (10 mg/kg) or vehicle (non-reactive isotype-matched antibody, 10 mg/kg). In selected studies, a group of MOG immunized EAE animals were treated weekly with 28B6 (10 mg/kg). Animals were sacrificed on day 21 after immunization, and central lymphoid organs were collected. Lymphocytes were prepared from the organs and stained as described below. Immunostained lymphocytes were analyzed by flow cytometry.

T cell populations in the BM, spleen, blood and thymus from EAE animals treated with antagonist IL-7R antibodies were significantly reduced compared to vehicle controls. As shown in FIG. 11, both CD4 T cell (FIG. 11A) and CD8 T cell (FIG. 11B) populations from BM, spleen, blood and lymph nodes were significantly reduced in antagonist IL-7R antibody treated EAE animals. This is consistent with the role of IL-7R in both CD4 and CD8 T cell development. However, B cell populations were not significantly reduced in all of peripheral lymphoid organs. This result differs from the mouse genetic data from the IL-7R knockout, which lacks both T and B cells.

Because IL-7R signaling is critical for naïve T cell survival and for memory T cell proliferation, the effect of antagonist IL-7R antibodies in the regulation of peripheral T cells was analyzed by immunostaining using activation markers CD44 and CD62L. $CD44^{lo}CD62L^{hi}$ represents naïve T cells, $CD44^{hi}CD62L^{lo}$ represents activated T cells and $CD44^{hi}CD62L^{hi}$ represent memory T cells. Compared to vehicle (nonreactive isotype-matched antibody) treated animals, antagonist IL-7R antibody treated mice had significantly depleted naïve T cell and activated T cell populations (FIGS. 12A and 12C). However, memory T cell populations were not significantly depleted (FIG. 12B). This selective depletion of naïve and activated T cell populations may provide benefit in that naïve T cell depletion can block nascent autoAg-specific T cell activation, in turn preventing EAE. Memory T cells are not depleted, and thus, anti-infection immunity is preserved.

A reduction of NK cells in antagonist IL-7R antibody treated EAE animals was not observed. A slight increase in the percent of NK cells was observed, presumably due to the decreased percent of CD4 and CD8 T cells. This data is consistent with the observation that IL-7/IL-7R signaling regulates T cell, but not for NK cell, development.

To determine the effect of antagonist IL-7R antibody treatment on $T_{reg}$ cell population in EAE animals, lymphocytes were stained for Foxp3 to identify $T_{reg}$ cells and MOG-MHC class II (I-Ab) tetramer to detect MOG-specific T cells. The population of MOG-specific CD4+ $T_{eff}$ cells detected in lymph nodes from 28G9 treated EAE animals was similar to that of control (nonreactive isotype-matched antibody-treated) animals (FIG. 13, left graph). However, an increase in $T_{reg}$ cell population was observed with 28G9 treatment (FIG. 13, right graph). These results demonstrate that treatment of EAE animals with antagonist IL-7R antibody results in an increase of $T_{reg}$ cell population. Advantageously, antagonist IL-7R antibody treatment may not develop other inflammatory disease, a side effect observed with IL-2Rα antibody therapy.

Lymphocyte Preparation and Immunofluorescent Staining

For the above studies, single-cell leukocyte suspensions from spleens, peripheral lymph nodes (paired axillary, bronchial and inguinal), thymus and bilateral femurs bone marrow (BM) were generated by gentle dissection. Mononuclear cells from the central nervous system (CNS) were isolated after cardiac perfusion with PBS. Briefly, CNS tissues were digested with collagenase D (2.5 mg/ml; Roche Diagnostics) and DNaseI (1 mg/ml; Roche Diagnostics) at 37° C. for 45 minutes. Mononuclear cells were isolated by passing the tissue through 70-µm cell strainers (BD Biosciences), followed by Percoll gradient (70%/37%) centrifugation. Lymphocytes were collected from the 37%/70% interface and washed. The following antibodies were used for immunostaining: FITC-, PE- or PE-Cy5-conjugated CD3 (17A2), CD4 (H129.19), CD8 (53-6.7), CD62L (MEL14), CD44 (IM7), B220 (H1.2F3), IgM (II/41), DX5 (CD49b) (all from BD Biosciences). For intracellular cytokine staining, lymphocytes were stimulated in vitro with phorbol 12-myristate 13-acetate (20 ng/ml; Sigma-Aldrich) and ionomycin (1 µg/ml; Sigma-Aldrich) in the presence of GolgiStop™ (monensin) (5 ug/ml) for 5 hours before staining. $MOG_{38-49}$/IAb tetramer and control tetramer (CLIP/IAb) were constructed and supplied by the NIH Tetramer Core Facility. Background staining was assessed using nonreactive, isotype-matched control mAbs. For 2- or 3-color immunofluorescence analysis, single-cell suspensions ($10^6$ cells) were stained at 4° C. using predetermined optimal concentrations of mAb for 20 minutes. For tetramer staining, lymphocytes were stained for 3 hours at 37° C.

Example 7

Antagonist IL-7R Antibodies Ameliorate Glucose Intolerance in Diet-Induced Obesity (DIO) Animals This example illustrates the effect of antagonist IL-7R antibodies in a mouse model for type 2 diabetes.

To study the in vivo effect of antagonist IL-7R antibodies on pre-established adipose inflammation in DIO mice, C57BL/6 male mice (The Jackson Laboratory) were fed a high fat diet (HFD, D12492, 60 Kcal % fat, Research Diets) beginning at six weeks old. After ten weeks of high fat diet, the 16-week-old obese mice were randomly assigned to groups for i.p. administration of antagonist IL-7R antibody 28G9 (10 mg/kg), PBS, or nonreactive isotype-matched control antibody (10 mg/kg). Four days after antibody treatment, the mice were subject to a glucose tolerance test (i.p. 1 g/kg, after 16 hr fasting) to assess glucose intolerance. Table 5 shows the average body weight and glucose levels for each of the treated groups (PBS-, isotype- or 28G9-treated mice). The animals in each group had similar body weight.

TABLE 5

| Treatment | Body weight (g) | Glucose (mg/dL) non-fasting/fasting |
|---|---|---|
| PBS | 44.4 | 232/152.6 |
| isotype | 42.3 | 233/183.6 |
| 28G9 | 41.4 | 229/122.2 |

The results of the glucose tolerance test are depicted in FIG. 14. Glucose intolerance induced by high fat diet was ameliorated by antagonist IL-7R antibody treatment. In the glucose tolerance test, DIO mice treated with 28G9 had significantly lower blood glucose levels compared to mice treated with isotype or PBS (FIG. 14). This result demonstrates that antagonist IL-7R antibodies are efficacious in an animal model for type 2 diabetes.

Example 8

Antagonist IL-7R Antibodies Reduce Disease Severity in a Mouse Model for Rheumatoid Arthritis This example illustrates the effect of antagonist IL-7R antibodies in a mouse model for rheumatoid arthritis (RA).

Collagen induced arthritis (CIA) is a widely used animal model sharing many pathological and histological similarities with RA. To study the in vivo effect of antagonist IL-7R antibodies on CIA, 6-8 week old male B10.RIII mice (stock #000457, The Jackson Laboratory) were immunized with 150 ug of Type II collagen (Elastin Products) emulsified in Freund's complete adjuvant containing 4 mg/ml heat-killed *Mycobacterium tuberculosis* H37RA (Difco) on day 0 and day 15. Mice were injected i.p. with 1, 3 or 10 mg/kg of antagonist IL-7R antibody 28G9 or nonreactive isotype-matched control antibodies on day −1, day 1, day 8, day 15 and day 22.

Clinical signs of CIA were assessed daily with a 0 to 5 point scoring system: 0, normal; 1, hind or fore paw joint affected or minimal diffuse erythema and swelling; 2, hind or fore paw joints affected or mild diffuse erythema and swelling; 3, hind or fore paw joints affected or moderate diffuse erythema and swelling; 4, Marked diffuse erythema and swelling; 5, diffuse erythema and severe swelling entire paw, unable to flex digits. Treatment with 28G9 at 3 mg/kg significantly reduced the severity of CIA in CII-immunized mice as compared to isotype control (FIG. 15). Treatment with 28G9 at 1 mg/kg did not show significant reduction. This result demonstrates that antagonist IL-7R antibodies are effective in slowing disease progession in an animal model for rheumatoid arthritis.

Example 9

Antagonist IL-7R Antibodies Reduce Disease Severity in a Mouse Model for Established EAE This example illustrates efficicacy of antagonist IL-7R antibodies in a mouse model for established EAE.

EAE was induced in SJL/J mice by immunization with 200 µg of PLP(p139-151) dissolved in complete Freund's adjuvant containing 4 mg/ml of heat-killed *Mycobacterium tuberculosis* H37Ra (Difco Laboratories). Mice were examined daily for bodyweight measurements and clinical signs of EAE and scored as follows: 0, no paralysis; 1, loss of tail tone; 2, hindlimb weakness; 3, hindlimb paralysis; 4, hindlimb and forelimb paralysis; 5, moribund or dead.

Mice having a EAE clinical score of 2-3 were treated with 28G9 (10 mg/kg, i.p.), SB/14 (10 mg/kg, i.p.) or control IgG (10 mg/kg, i.p.) once a week for 2 weeks (on days 0, 7 and 14). 28G9 is rat IgG1 antibody and SB/14 (BD Biosciences) is a rat IgG2a antibody. Clinical scores were monitored daily until day 61.

By day 7, mice treated with 28G9 had clinical scores lower than 2 (N=7). The mice treated with 28G9 maintained clinical scores of about 2 until the end of the study (day 61). In comparison, the control IgG-treated animals had clinical scores between 3 and 4 throughout the study. No reduction of disease severity was observed with SB/14 treatment compared to the control.

A highly significant reduction of disease severity was observed in 28G9 antagonist IL-7R antibody treated animals. These results demonstrate that antagonist IL-7R antibodies are effective in reducing disease severity in established autoimmune disease.

Example 10

Antagonist IL-7R Antibodies Reduce Blood Glucose Levels in Animals with Newly Onset Diabetes This example illustrates the efficacy of antagonist IL-7R antibodies in reversing newly onset diabetes in a mouse model for type 1 diabetes.

A panel of antagonist IL-7R antibodies were tested in a mouse model for type 1 diabetes. 28G9 is a rat IgG1 monoclonal antibody, 28G9-mIgG2a is an antibody having the 28G9 variable regions with mouse IgG2a constant region, and agly-28G9 is an aglycosylated antibody having the 28G9 variable regions with mouse IgG2a N297A. For construction and expression of 28G9-mIgG2a, the VH and Vk gene of rat monoclonal antibody 28G9 were amplified by PCR, cloned into pARC mouse IgG2a and pARC mouse kappa mammalian expression vectors, and cotransfected into 293F cells by Lipofectamin™ (Invitrogen™). After 5 days of post-transfection, the culture media was harvested and the 28G9 mouse IgG2a was purified by using Mabselect™ (GE) resin. For construction and expression of agly-28G9, the VH of rat 28G9 was cloned into an engineered pARC mouse IgG2a vector in which Asn-297 of the CH2 domain was replaced by Ala (pARC mouse IgG2a-N297A). An aglycosylated m28G9 (agly-28G9) was obtained by cotransfection of 293F cells with pARC mouse IgG2a-N297A and pARC-28G9 mouse kappa vector.

Spontaneous new onset diabetic NOD mice (i.e., two consecutive blood glucose concentrations over 250 mg/dl) were treated i.p. weekly with 28G9-mIgG2a (10 mg/kg, i.p.), 28G9 (10 mg/kg, i.p.), agly-28G9 (10 mg/kg, i.p.) or control IgG (10 mg/kg, i.p.). Blood glucose levels were monitored daily for 140 days after disease onset. In mice treated with 28G9-mIgG2a, 100% remission was observed. In the 28G9-mIgG2a treated NOD mice, blood glucose levels were maintained below 250 mg/dl with weekly 28G9-mIgG2a injections. 28G9 also showed some efficacy in reducing blood glucose levels compared to control IgG. Agly-28G9-treated and control IgG-treated mice had blood glucose levels of greater than 250 mg/dl throughout the study. These results demonstrate that 28G9-mIgG2a antagonist IL-7R antibody is highly effective in reducing blood glucose levels in mice with established type 1 diabetes.

In a separate study, spontaneous new onset diabetic NOD mice were treated weekly, beginning at disease onset, with 28G9-mIgG2a (10 mg/kg i.p.) for the number of doses indicated in Table 6. Blood glucose levels were monitored daily.

TABLE 6

| Mouse | Age at disease onset (days) | Total # of doses | Days diabetes-free |
|---|---|---|---|
| 1 | 140 | 3 | 117 |
| 2 | 190 | 2 | 89 |
| 3 | 210 | 3 | 145 |

The results shown in Table 6 indicate that two doses of antagonist IL-7R antibody were sufficient to maintain blood glucose levels lower than 250 mg/dL for up to 89 days. Three doses of antagonist IL-7R antibody were sufficient to maintain blood glucose levels lower than 250 mg/dL for at least 117 days. In this study, blood glucose levels maintained at lower than 250 mg/dL were observed for up to five months post-antagonist IL-7R antibody treatment.

The results of the studies described above demonstrate that antagonist IL-7R antibody 28G9-mIgG2a was highly effective in reducing blood glucose levels in animals with newly onset diabetes. Furthermore, mice treated with just two or three doses of antagonist IL-7R antibodies maintained blood glucose levels lower than 250 mg/dL for several months after antibody was administered.

Example 11

Antagonist IL-7R Antibodies Reduce Disease Severity in Mouse Models for Graft-Versus-Host Disease (GVHD)

This example illustrates the effect of antagonist IL-7R antibodies in mouse models for acute and chronic graft-versus-host disease (GVHD).

Acute GVHD

For the mouse model of acute GVHD, $10 \times 10^6$ human PBMC (freshly isolated) were injected into non-irradiated NOD.SCID IL2Rγ-/- mice (The Jackson Laboratory, 8-12 weeks old). 14 days after injection, the mice are treated with 10 mg/kg antagonist antagonist IL-7R fully human IgG1 antibody HAL403b (n=10) or isotype control (n=10) once weekly. Clinical signs of GVHD and body weight are monitored twice a week. Forty days post-treatment, 100% of antagonist IL-7R antibody-treated animals remained alive, in contrast to only 50% of isotype control-treated animals survived. This result indicates that antagonist IL-7R antibodies are effective in reducing mortality rate in an animal model for acute GVHD.

Chronic GVHD

For the chronic GVHD mouse model, human cord blood cells containing a small (1-5%) percentage of CD3+ T cells are transplanted into newborn irradiated NOD.SCID IL2Rγ-/- mice. Briefly, human CD34+ cord blood (AllCells, LLC, Emeryville, Calif.) was depleted of CD3+ T cells using human CD3 selection beads (Miltenyi Biotec GmBH, Germany, CAT #130-050-101) For the transplantation, about 300,000 to 400,000 CD34+ cells containing about 1-5% CD3+ T cells (in a volume of 50 µl) are intracardially injected per newborn irradiated NOD.SCID IL2Rγ-/- mouse (The Jackson Laboratory). cGVHD develops 16-20 weeks post-transplantation.

Beginning at 24 weeks of age, mice with cGVHD are injected with 10 mg/kg antagonist IL-7R fully human IgG1 antibody HAL403b (n=4) or PBS (n=4) once weekly until sacrifice.

Mice are sacrificed at about 28-32 weeks old, after about 4 to 8 weeks of antagonist IL-7R antibody or PBS treatment. Mice treated with antagonist IL-7R fully human IgG1 antibody had significantly less hair loss than mice injected with PBS. Histologic analysis showed kidneys of PBS-treated mice were generally more severely affected than kidneys of antagonist IL-7R antibody-treated mice. For example, kidneys of control (PBS-treated) mice had markedly thickened capillary loops with increased amounts of eosinophilic material. In contrast, kidneys of mice treated with antagonist IL-7R antibody had mildly thickened capillary loops with increased amount of eosinophilic material. In addition, kidneys of mice treated with antagonist IL-7R antibody had fewer dilated tubules compared to kidneys of mice treated with isotype control, which showed many dilated tubules. Lung histology revealed substantially reduced bronchial associated lymphoid tissue (BALT) in lungs of mice treated with antagonist IL-7R antibody compared to lungs of control mice, which had some BALT present. Severe lymphoid atrophy was observed in spleen of mice treated with antagonist IL-7R antibody, compared to the mild to moderate change in spleen of mice treated with PBS.

These results indicate that antagonist IL-7R antibodies are effective in reducing disease severity in an animal model for chronic GVHD.

Example 12

Antagonist IL-7R Antibodies Reduce Disease Severity in a Mouse Model for Lupus

This example illustrates the effect of antagonist IL-7R antibodies in a mouse model for lupus.

For the mouse model of lupus, MRL/MpJ-Fas$^{lpr}$/J mice (The Jackson Laboratory) were used. Commonly referred to as lpr mutants, these mice are homozygous for the lymphoproliferation spontaneous mutation (Fas$^{lpr}$) and show systemic autoimmunity, massive lymphadenopathy associated with proliferation of aberrant T cells, arthritis, and immune complex glomerulonephrosis. As such, the MRL/MpJ-Fas$^{lpr}$/J mice are useful as a model for systemic lupus erythematosus.

Beginning at the time of disease onset, mice were dosed i.p. weekly with 1, 3, or 10 mg/kg 28G9-mIgG2a antagonist IL-7R antibody (see Example 10), 1 mg/kg agly-28G9 antagonist IL-7R antibody, an isotype control IgG (negative control) or cyclophosphamide (positive control). For each treatment group, ten mice were used (n=10). Disease severity was monitored by measuring proteinuria levels, activity levels, and assessing the righting reflex. In assessing the righting reflex, mice that failed to right themselves within 30 seconds were sacrificed. Suvival rate is summarized in Table 7 below.

TABLE 7

| Treatment | Survival rate at 8 weeks after disease onset | Survival rate at 12 weeks after disease onset |
|---|---|---|
| 1 mg/kg 28G9-mIgG2a | 60% | 50% |
| 3 mg/kg 28G9-mIgG2a | 80% | 70% |

TABLE 7-continued

| Treatment | Survival rate at 8 weeks after disease onset | Survival rate at 12 weeks after disease onset |
|---|---|---|
| 10 mg/kg 28G9-mIgG2a | 90% | 80% |
| 1 mg/kg agly-28G9 | 100% | 100% |
| isotype control IgG (negative control) | 60% | 60% |
| cyclophosphamide (positive control) | 80% | 80% |

As shown in Table 7, mice treated with 1 mg/kg agly-28G9, 3 mg/kg 28G9-mIgG2a or 10 mg/kg 28G9-mIgG2a had an increased survival rate compared to mice treated with isotype control IgG. These results indicate that antagonist IL-7R antibodies are effective in reducing disease severity in an animal model for lupus.

Example 13

Epitope Mapping/Binding of Antagonist IL-7R Antibodies

This example illustrates structure-guided mutagenesis to map antibody binding epitopes.

Based on the crystal structure of the IL-7/IL-7Rα complex and the likely involvement of certain residues in IL-7 binding (McElroy et al., 2009, Structure, 17(1):54-65, twenty-three IL-7Rα surface-residue mutants (N29D, V58S, E59R, R66N, K77S, L80S, I82S, K84S, K100S, T105A, N131S, Q136K, K138S, Y139F, K141S, M144A, D190S, H191N, Y192A, Y192F, K194S, K194A and F196S) were chosen for mutation to map the antibody binding epitopes. The numbering for the mutants (i.e., N29D, V58S, E59R, etc.) follows the convention of post-processed protein wherein the first 20 amino acids are not counted.

A panel of IL-7Rα single point mutants (his-tagged) were prepared as follows. The twenty-three IL-7Rα single point mutants described above were generated from the previously described wild-type DNA construct (McElroy et al., 2009, supra) using standard DNA techniques. The mutant proteins were expressed using transient transfection in HEK293T cells and secreted into the cell media. The mutant proteins were purified by Ni$^{2+}$ column chromatography. Protein concentrations were measured by spectrophotometry (Nanoprop™).

Interaction analysis of IL-7Rα was performed at 25° C. using a surface-plasmon resonance-based ProteOn™ XPR36 biosensor equipped with a GLM sensor chip (Bio-Rad, Hercules, Calif., USA). HBST running buffer (10 mM Hepes pH7.4, 150 mM NaCl, 0.05% v/v Tween-20) was used throughout. Full-length IL-7R antibodies (HAL403a or HAL403b) were amine-coupled onto separate "vertical" channels of the chip via standard EDC/sulfo-NHS-mediated chemistry to levels of about 2000-5000 RU. The panel of IL-7Rα mutants (including wild-type IL-7Rα) was screened in the "horizontal" direction at 100 nM using association and dissociation phases of 3 and 10 mins respectively at 30 uL/min. Surfaces were regenerated with 2/1 v/v Pierce immunopure elution buffer (pH2.8)/4M NaCl. Most injections were duplicated to confirm that the assay was reproducible.

Table 8 summarizes the impact of the single point mutations in the IL-7Rα mutants on antibody binding compared to wild-type IL-7Rα.

TABLE 8

| IL-7Rα mutant | Impact on antibody (HAL403a or HAL403b) binding |
|---|---|
| I82S | Highly impaired |
| K84S, K100S, T105A, Y192A | Impaired |
| D190S, H191N, K194S | Slightly impaired |
| N29D, V58S, E59R, R66N, K77S, L80S, N131S, Q136K, K138S, Y139F, K141S, M144A, Y192F, K194A, F196S, (wild-type) | None |

The IL-7Rα mutants displaying weakened antibody binding compared to wild-type IL-7Rα were identified as having a point mutation at a residue involved in mAb binding. The binding residues of IL-7Rα to antibody HAL403a in descending order of mutant effects were identified as follows: I82 (high impact on binding), K84 (medium impact), K100 (medium impact), T105 (medium impact), Y192 (medium impact), D190 (small impact), H191 (small impact), and K194 (small impact). The binding residues of IL-7Rα to antibody HAL403b in descending order of mutant effects were identified as follows: I82 (high impact on binding), K84 (medium impact), K100 (medium impact), T105 (medium impact), Y192 (medium impact), D190 (small impact), H191 (small impact), and K194 (small impact).

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is claimed:

1. An isolated antibody which specifically binds to interleukin-7 receptor alpha (IL-7Rα), wherein the antibody comprises:
   a heavy chain variable region (VH) comprising CDR1, CDR2, and CDR3 of SEQ ID NO: 40; and
   light chain variable region (VL) comprising CDR1, CDR2, and CDR3 of SEQ ID NO: 41.

2. The isolated antibody of claim 1, wherein the VH region comprises a VH CDR1 having the amino acid sequence shown in SEQ ID NO: 19, 46 or 47; a VH CDR2 having the amino acid sequence shown in SEQ ID NO: 23 or 48; and a VH CDR3 having the amino acid sequence shown in SEQ ID NO: 49.

3. The isolated antibody of claim 2, wherein the VL region comprises a VL CDR1 having the amino acid sequence shown in SEQ ID NO: 29, a VL CDR2 having the amino acid sequence shown in SEQ ID NO: 31, and a VL CDR3 having the amino acid sequence shown in SEQ ID NO: 36.

4. The antibody of claim 1, wherein the VH region comprises the amino acid sequence shown in SEQ ID NO: 40 and the VL region comprises the amino acid sequence shown in SEQ ID NO: 41.

5. The antibody of claim 4, wherein said antibody comprises a light chain having the amino acid sequence shown in SEQ ID NO: 43 and a heavy chain having the amino acid sequence shown in SEQ ID NO: 42, with or without the C-terminal lysine of SEQ ID NO: 42.

6. The isolated antibody of claim 1, wherein each CDR is defined in accordance with the Kabat definition, the Chothia definition, the combination of the Kabat definition and the Chothia definition, the AbM definition, or the contact definition of CDR.

7. The antibody of any claim 1, wherein the antibody further comprises a constant region.

8. The antibody of claim 7, wherein the antibody is of the human IgG1 or IgG2Δa subclass.

9. A pharmaceutical composition comprising the antibody of claim 1.

10. A cell line that recombinantly produces the antibody of claim 1.

* * * * *